(12) United States Patent
Gardinier et al.

(10) Patent No.: US 12,228,553 B2
(45) Date of Patent: Feb. 18, 2025

(54) ULTRASMALL NANOPARTICLES AND METHODS OF MAKING, USING AND ANALYZING SAME

(71) Applicant: Cornell University, Ithaca, NY (US)

(72) Inventors: Thomas C. Gardinier, Raritan, NJ (US); Ferdinand F. E. Kohle, Tubingen (DE); Joshua A. Hinckley, Ithaca, NY (US); Ulrich B. Wiesner, Ithaca, NY (US)

(73) Assignee: Cornell University, Ithaca, NY (US)

( * ) Notice: Subject to any disclaimer, the term of this patent is extended or adjusted under 35 U.S.C. 154(b) by 986 days.

(21) Appl. No.: 17/052,155

(22) PCT Filed: May 2, 2019

(86) PCT No.: PCT/US2019/030492
§ 371 (c)(1),
(2) Date: Oct. 30, 2020

(87) PCT Pub. No.: WO2019/213456
PCT Pub. Date: Nov. 7, 2019

(65) Prior Publication Data
US 2021/0048414 A1 Feb. 18, 2021

Related U.S. Application Data

(60) Provisional application No. 62/666,076, filed on May 2, 2018.

(51) Int. Cl.
*G01N 30/02* (2006.01)
*G01N 21/64* (2006.01)
(Continued)

(52) U.S. Cl.
CPC ............ *G01N 30/02* (2013.01); *G01N 21/64* (2013.01); *B82Y 30/00* (2013.01); *B82Y 35/00* (2013.01);
(Continued)

(58) Field of Classification Search
CPC .................... A61K 47/6923; A61K 49/0067; B82Y 30/00; B82Y 35/00; B82Y 40/00;
(Continued)

(56) References Cited

U.S. PATENT DOCUMENTS

| 4,263,268 A | 4/1981 | Knox et al. |
| 10,039,847 B2 | 8/2018 | Bradbury et al. |

(Continued)

FOREIGN PATENT DOCUMENTS

| CN | 109453393 A | 3/2019 |
| KR | 20170005204 A | 1/2017 |

(Continued)

OTHER PUBLICATIONS

Alvarado, S. J., Qualitative HPLC Analysis of Peptide Functionalized Fluorescent Silica-Nanoparticles for Applications in Nanomedicine, Thesis, Cornell University, Jan. 2017, 61 pages.

(Continued)

*Primary Examiner* — Andre J Allen
(74) *Attorney, Agent, or Firm* — Hodgson Russ LLP

(57) ABSTRACT

The present disclosure provides methods of analyzing and/or purifying inorganic nanoparticles that may be functionalized with one or more dye group. Analyzing and/or purifying the inorganic nanoparticles includes utilizing liquid chromatography, such as, for example, high performance liquid chromatography (HPLC). Methods of the present disclosure may be used to determine the location of one or more dye groups on and/or in the inorganic nanoparticles. The present dis- (Continued)

closure also provides methods of making inorganic nanoparticles and compositions of inorganic nanoparticles.

17 Claims, 43 Drawing Sheets

(51) Int. Cl.
*B82Y 30/00* (2011.01)
*B82Y 35/00* (2011.01)
*B82Y 40/00* (2011.01)

(52) U.S. Cl.
CPC ...... *B82Y 40/00* (2013.01); *G01N 2021/6439* (2013.01); *G01N 2030/027* (2013.01)

(58) Field of Classification Search
CPC ..... G01N 2021/6439; G01N 2030/027; G01N 21/64; G01N 30/02
See application file for complete search history.

(56) References Cited

U.S. PATENT DOCUMENTS

| | | | |
|---|---|---|---|
| 11,291,737 B2 | 4/2022 | Wiesner et al. | |
| 11,419,952 B2 | 8/2022 | Ma et al. | |
| 2010/0190726 A1 | 7/2010 | Katz et al. | |
| 2013/0045161 A1 | 2/2013 | Sigalov | |
| 2018/0133346 A1 | 5/2018 | Wiesner et al. | |
| 2021/0048414 A1 | 2/2021 | Gardinier et al. | |
| 2024/0149245 A1 * | 5/2024 | Turker | B01J 20/16 |

FOREIGN PATENT DOCUMENTS

| | | | | |
|---|---|---|---|---|
| WO | WO-2004074504 A2 * | 9/2004 | ............. | A61P 35/00 |
| WO | WO-2005052591 A1 * | 6/2005 | ....... | G01N 33/48721 |
| WO | WO-2011088627 A1 * | 7/2011 | ............. | B82Y 30/00 |
| WO | WO-2012128162 A1 * | 9/2012 | ......... | A61K 49/0093 |
| WO | 2016/179260 A1 | 11/2016 | | |
| WO | WO-2018213851 A1 * | 11/2018 | ............. | A61K 47/02 |
| WO | WO-2021092065 A1 * | 5/2021 | ......... | A61K 49/0093 |
| WO | WO-2022234721 A1 * | 11/2022 | | |

OTHER PUBLICATIONS

Benezra, M,. et al., Multimodal silica nanoparticles are effective cancer-targeted probes in a model of human melanoma, The Journal of Clinical Investigation, Jun. 13, 2011, vol. 121, No. 7, pp. 2768-2780.

Ma, K., et al., Elucidating the Mechanism of Silica Nanoparticle PEGylation Processes Using Fluorescence Correlation Spectroscopies, Chemistry of Materials, Feb. 8, 2016, vol. 28, No. 5, pp. 1537-1545.

Ricco, R., et al., Ultra-small dye-doped silica nanoparticles via modified sol-gel technique, Journal of Nanoparticle Research, Apr. 25, 2018, vol. 20, No. 117, pp. 1-9.

Larson, D.R., et al., Silica Nanoparticle Architecture Determines Radiative Properties of Encapsulated Fluorophores, Chemistry of Materials, Mar. 15, 2008, vol. 20. No. 8, pp. 2677-2684.

Chen, F., et al., Renally Clearable PSMA Inhibitors Conjugated Ultrasmall Silica Nanoparticles Enhance the Specific Detection of Prostate Cancer In Vivo, The Journal of Nuclear Medicine, May 1, 2018, vol. 59, No. 1, p. 467 (3 pages).

Alsolmy, E., et al., A Comparative Study of Fluorescein Isothiocyanate-Encapsulated Silica Nanoparticles Prepared in Seven Different Routes for Developing Fingerprints on Non-Porous Surfaces, Journal of Fluorescence, Jul. 21, 2018, vol. 28, Abstract, 2 pages.

Fujii, T., et al., Absorption and fluorescence spectra of rhodamine B molecules encapsulated in silica gel networks and their thermal stability, Journal of Photochemistry and Photobiology A: Chemistry, Nov. 1, 1990, vol. 54, No. 2, pp. 231-237.

* cited by examiner

G

H

I

Sulfo-Cy5.5-NHS-ester

Cy5.5-NHS-ester

Sulfo-Cy5-NHS-ester

Cy5-NHS-ester

Sulfo-Cy3 acid

Cy3 NHS-ester

ATTO647N

ATTO620

ATTO465

ATTO495

ATTO520

ATTORho6G

ATTORho3B

ATTORho11

ATTORho12

ATTOThio12

ATTORho101

ATTORho13

ATTO610

ATTORho14

ATTOMB2

ATTO488

Alexa Fluor 532 NHS ester

Alexa Fluor 430

ATTO532

ATTO594

ATTO390

ATTO425

ATTO565

ATTO590

ATTO647

ATTO655

ATTO680

ATTO700

ULTRASMALL NANOPARTICLES AND METHODS OF MAKING, USING AND ANALYZING SAME

CROSS REFERENCE TO RELATED APPLICATIONS

This application claims priority to U.S. Provisional Application No. 62/666,076, filed on May 2, 2018, the disclosure of which is hereby incorporated by reference.

STATEMENT REGARDING FEDERALLY SPONSORED RESEARCH OR DEVELOPMENT

This invention was made with government support under Grant Number CA199081 awarded by National Institutes of Health. The government has certain rights in the invention.

FIELD OF THE DISCLOSURE

The disclosure generally relates to analysis and purification of nanoparticles. More particularly, the disclosure relates to the analysis of nanoparticles by HPLC.

BACKGROUND OF THE DISCLOSURE

Silica nanoparticles (SNPs) have attracted interest for potential therapeutic/diagnostic applications due to their large surface-area, inertness and high bio-compatibility. However, most SNPs are >10 nm in size.

Particles >12 nm are not effectively cleared from the body in vivo and unfavorably distribute to the liver and other organs/tissues, potentially exposing these tissues to toxic elements (especially if these >10 nm SNPs are modified with drugs and/or radioactivity). Particles about 8 nm in diameter reside in the body for about a day, 10-11 nm about 3-5 days, but if greater than 12 nm do not clear or clear very slowly.

Currently, ultrasmall inorganic nanoparticles are of rapidly increasing interest as nanomedicines for cancer theranostics. Some organic based nanomedicines are already more competitive than conventional chemotherapy drugs due to multifunctionality and multivalency effects. Inorganic nanoparticles further diversify the building elements of nanomedicines and may provide advantages associated with their intrinsic physical properties and lower manufacturing costs. Safe translation of nanoparticles from the laboratory to the clinic requires overcoming a number of substantial scientific and regulatory hurdles. The most important criteria are favorable biodistribution and its time evolution (pharmacokinetics, PK) profiles. The size threshold for renal clearance is below 10 nm. Until today only a small number of inorganic nanoparticle platforms have been synthesized with sizes below 10 nm allowing for efficient renal clearance. Among those only <10 nm sized polyethylene glycol coated (PEGylated) fluorescent core-shell silica nanoparticles (SNPs) referred to as Cornell dots or simply C dots have been approved by the U.S. Food and Drug Administration (FDA) as an investigational new drug (IND) for first in-human clinical trials. Although the first clinical trial results with melanoma patients are encouraging, several synthesis challenges remain for such sub 10 nm sized fluorescent organic-inorganic hybrid SNPs.

First, all previous C dot-type SNP synthesis efforts followed a modified Stöber process in which alcohol was used as solvent. For materials for use in biological or clinical applications, however, water as a reaction medium would be preferred. It would greatly simplify synthesis and cleaning protocols leading to less volatile waste, thereby rendering particle production substantially faster and more cost effective. Furthermore, although the Stöber process is widely used to produce SNPs with diameters from tens of nm to microns, particle sizes of 10 nm and below are at the limit of size control of this synthesis process due to reaction kinetics limitations in alcohol.

Second, covalently covering silica particle surfaces with PEG can be tricky as the loss of surface charge during PEGylation may result in particle aggregation or at least broadening of the particle size distribution. This effect is more pronounced for ultrasmall particles due to the increase of particle surface energy, and thus limits the particle monodispersity and size control ability.

Third, as a result of the negative surface charge of silica above its isoelectric point at pH 2-3, covalent encapsulation efficiencies for silane-conjugated organic fluorescent dyes with negatively charged groups into SNPs are low as a result of electrostatic repulsion between silica and fluorophore. This is particularly true for near-infrared (NIR) emitting dyes most desirable for imaging applications in living tissue. NIR dyes have large delocalized $\pi$-electron systems and to be soluble in water typically require multiple negatively charged functional groups (e.g. sulfates) on their periphery. Low incorporation efficiencies are a problem for these dyes as their typical costs are of order $200-$300 per mg and re-use of typically employed silane-dye conjugates after the initial synthesis is problematic.

Finally, no inorganic elemental compositions other than silica have been reported for <10 nm sized fluorescent SNPs and core-shell SNPs. In particular, compositions are of interest leading to higher rigidity of the organic dye environments as increases in rigidity have directly been correlated with increases in per dye fluorescence yield as a result of decreases in non-radiative rates.

All these challenges suggest revisiting the original fluorescent core-shell SNP (C dot) synthesis in order to systematically develop a water based approach to <10 nm organic-inorganic hybrid dots with improved size control, previously unknown compositions, and enhanced performance characteristics.

In 2014, results were reported of a first human clinical trial with ultra-small poly(ethylene glycol) coated (PEGylated) sub-10 nm fluorescent core-shell silica nanoparticles referred to as Cornell dots (C dots). These first-generation particles were synthesized using a modified Stöber synthesis in alcohol. Shortly afterwards, an alternative synthesis approach was developed using water as the reaction medium and leading to improved physico-chemical particle properties, including higher brightness and better size control. In order to distinguish these second-generation particles synthesized in water from the first alcohol derived materials they were termed Cornell prime dots, or simply C' dots. Multiple human clinical trials with C' dots are ongoing, including a phase two trial with melanoma patients.

More recently, it has been shown that in in-vitro and in-vivo experiments C' dots induce a form of programmed cell death called ferroptosis in tumor cells under nutrient deprived conditions. This elevated the C' dot nanoparticle platform from original diagnostic applications to the ream of therapy. For therapeutic applications requiring orders of magnitude higher particle doses (micromolar as opposed to nanomolar amounts per injection), advances in physico-chemical particle characterization are highly desirable. For a number of C' dot applications to date cyanine5 dye (Cy5) has been incorporated into the particles as the fluorescent marker due to the near-infrared (NIR) absorbance at 650 nm and emission around 670 nm. These absorbance and emission characteristics surpass lower absorbing dyes due to the increased penetration depth of the low energy photons in biological tissue. Cy5 has downsides, however, such as comparatively low photo-stability and photo-isomerization that creates non-fluorescent species thus lowering dye brightness.

There is an ongoing and unmet need for methods to produce inorganic nanoparticles with desirable features.

SUMMARY OF THE DISCLOSURE

The present disclosure provides methods of analyzing and/or purifying inorganic nanoparticles (e.g., core or core-shell nanoparticles). The inorganic nanoparticles are also referred to herein as ultrasmall nanoparticles. The present disclosure also provides methods of making inorganic nanoparticles and compositions comprising inorganic nanoparticles.

In various examples, the present disclosure provides:
(1) The application of high performance liquid chromatography (HPLC) methods, which enabled the discovery of hitherto unknown surface-chemical heterogeneities in inorganic nanoparticles (e.g., fluorescent core-shell silica nanoparticles).
(2) The identification of design criteria to overcome the intrinsic nanoparticle heterogeneities observed.
(3) The discovery that fluorescent dye charge is a crucial parameter in the control of surface chemistry heterogeneity.
(4) The use of positively charged dyes, such as ATTO647N and MB2 in some embodiments to synthesize C' dots with highly homogeneous surface-chemical properties, displaying only a single peak in the HPLC analysis.
(5) These homogeneous C' dots exhibit profoundly higher stability against chemical degradation.
(6) These homogeneous C' dots exhibit profoundly higher photostability when compared to previously reported materials.

In certain examples, the present disclosure provides:
(1) Creation of an ultrasmall (sub-10 nm) nanoparticle with a completely homogeneous surface chemistry.
(2) Reduces dye sensitivity to solvent environment, normally hydrophobic dyes like ATTO647N cannot be reliably used in water-based applications.
(3) Uses for clinically relevant diagnostic imaging.
(4) Uses for improvement of bio-distribution of nanoparticle diagnostics and therapies (5) Uses for other nanoparticles in the process of clinical translation.
(6) Useful to analyze surface chemistry engineering for PEGylated materials which was until now not straight forward.

In an aspect, the present disclosure provides the analysis and/or purification of inorganic nanoparticles via liquid chromatography. The analysis and/or purification may be carried out using HPLC and/or GPC.

Inorganic nanoparticles comprising various dye groups may be suitable for analysis and/or purification. The dye groups may be located in various locations on and/or in (encapsulated by or partially encapsulated by) an inorganic nanoparticle. The dye groups may be disposed or partially disposed on the surface of an inorganic nanoparticle, encapsulated or partially encapsulated by the inorganic nanoparticle, or a combination thereof. A dye group disposed or partially disposed on the surface of an inorganic nanoparticle may refer to the dye group being part of a PEG group disposed or partially disposed on the surface of the inorganic nanoparticle.

Inorganic nanoparticles may be analyzed by high performance liquid chromatography (HPLC). HPLC may be used to determine the location of one or more dye group on and/or in (e.g., encapsulated by) an inorganic nanoparticle. Such a method may comprise subjecting a plurality of inorganic nanoparticles to HPLC analysis.

A composition comprising a plurality of inorganic nanoparticles may be purified using liquid chromatography. In an example, the liquid chromatography is GPC or preparative scale HPLC (e.g., preparative-scale RP-HPLC).

Methods of purification and/or analysis may generate eluent containing a purified, an analyzed, and/or a selected portion of inorganic nanoparticles. The purified, analyzed, and/or selected portion of inorganic nanoparticles may be referred to as fractions. The fractions may be combined to generate various compositions comprising desirable combinations of inorganic nanoparticles. For example, a fraction containing a plurality of inorganic nanoparticles, where individual inorganic nanoparticles encapsulate one or more anionic dye groups, may be combined with a fraction containing a plurality of inorganic nanoparticles, where individual inorganic nanoparticles have one anionic dye group disposed or partially disposed on the exterior surface of the individual inorganic nanoparticles.

In an aspect, the present disclosure provides a method of making inorganic nanoparticles (e.g., ultrasmall nanoparticles). The methods are based on use of aqueous reaction medium (e.g. water). The nanoparticles can be surface functionalized with polyethylene glycol groups (e.g., PEGylated) and/or various dye groups. A dye group disposed or partially disposed on the surface of an inorganic nanoparticle may refer to the dye group being part of a PEG group disposed or partially disposed on the surface of the inorganic nanoparticle.

In an aspect, the present disclosure provides compositions comprising inorganic nanoparticles of the present disclosure. The compositions can comprise one or more types (e.g., having different average size and/or one or more different compositional feature).

In an aspect, the present disclosure provides uses of the inorganic nanoparticles and compositions of the present disclosure. For example, inorganic nanoparticles or a composition comprising the inorganic nanoparticles are used in delivery and/or imaging methods.

This disclosure provides a method for imaging biological material such as cells, extracellular components, or tissues comprising contacting the biological material with inorganic nanoparticles comprising one or more positively charged dyes, or compositions comprising the nanoparticles; directing excitation electromagnetic (e/m) radiation, such as light, on to the tissues or cells thereby exciting the positively charged dye molecules; detecting e/m radiation emitted by the excited positively charged dye molecules; and capturing and processing the detected e/m radiation to provide one or more images of the biological material. One or more of these steps can be carried out in vitro or in vivo. For example, the cells or tissues can be present in an individual or can be present in culture. Exposure of cells or tissues to e/m radiation can be effected in vitro (e.g., under culture conditions) or can be effected in vivo. For directing e/m radiation at cells, extracellular materials, tissues, organs and the like within an individual or any portion of an individual's body that are not easily accessible, fiber optical instruments can be used.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
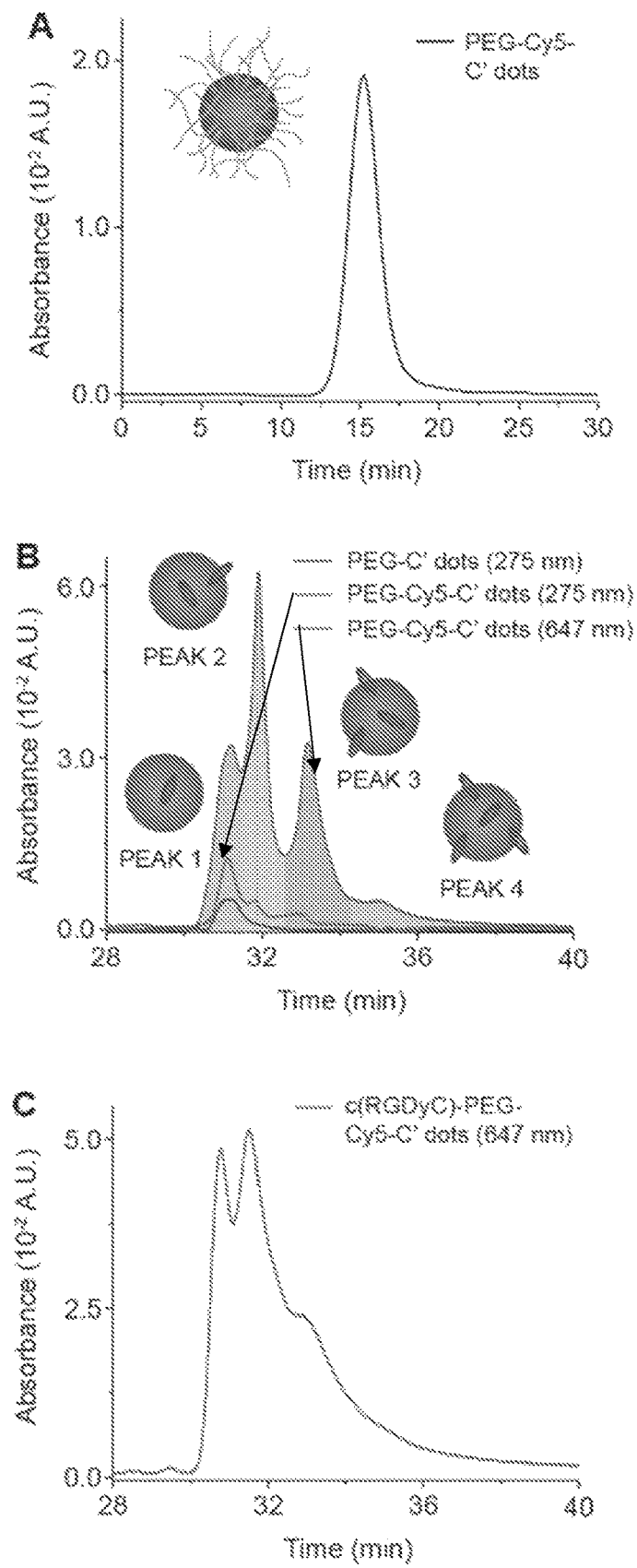
FIG. 1 shows nanoparticle heterogeneity and its analysis. (A) GPC chromatogram of purified PEG-Cy5-C' dots recorded at 275 nm with particle illustration (inset). (B) HPLC chromatograms of PEG-Cy5-C' dots recorded at 647 nm (main) as well as of PEG-C' dots (black) and PEG-Cy5-C' dots (red) recorded at 275 nm. Next to the main peaks are schematics of suggested particle structure. (C) HPLC chromatogram of c(RGDyC)-PEG-Cy5-C' dots recorded at 647 nm. (D) Schematic of a biotin functionalized PEG-Cy5-C' dots immobilized on a streptavidin coated glass slide for TIRFM, and (E) representative photobleaching time series carried out on immobilized PEG-Cy5-C' dots. (F) Four representative particle fluorescence intensity time traces from photobleaching experiments. Red arrows indicate dye bleaching events. (G) Dye distribution in PEG-Cy5-C' dot batch derived from photobleaching experiments. (H) (i) FCS correlation curves for free Cy5 dye and PEG-Cy5-C' dots under peaks 1-3 in (B) collected from successive HPLC runs. (ii) Correlation curves showing the individual contributions of cis-trans photoisomerization to respective FCS curves in (i). (I) Hydrodynamic diameter, (J) brightness per dye, (K) dyes per particle, and (L) photoisomerization percentage for free Cy5 dye as compared to PEG-Cy5-C' dots from HPLC fractionated peaks 1-3 in (B).
Figure 1:
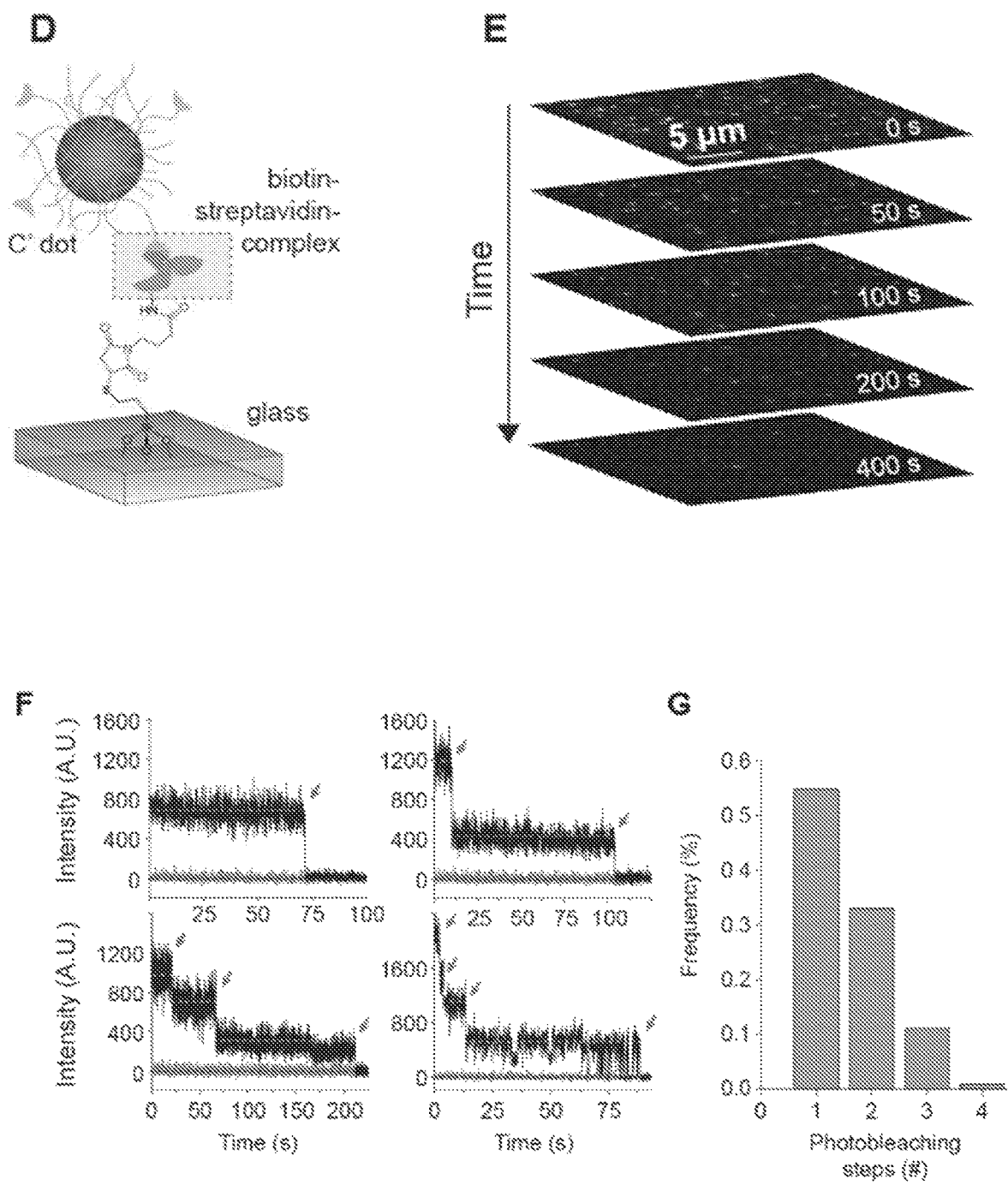
Figure 1:
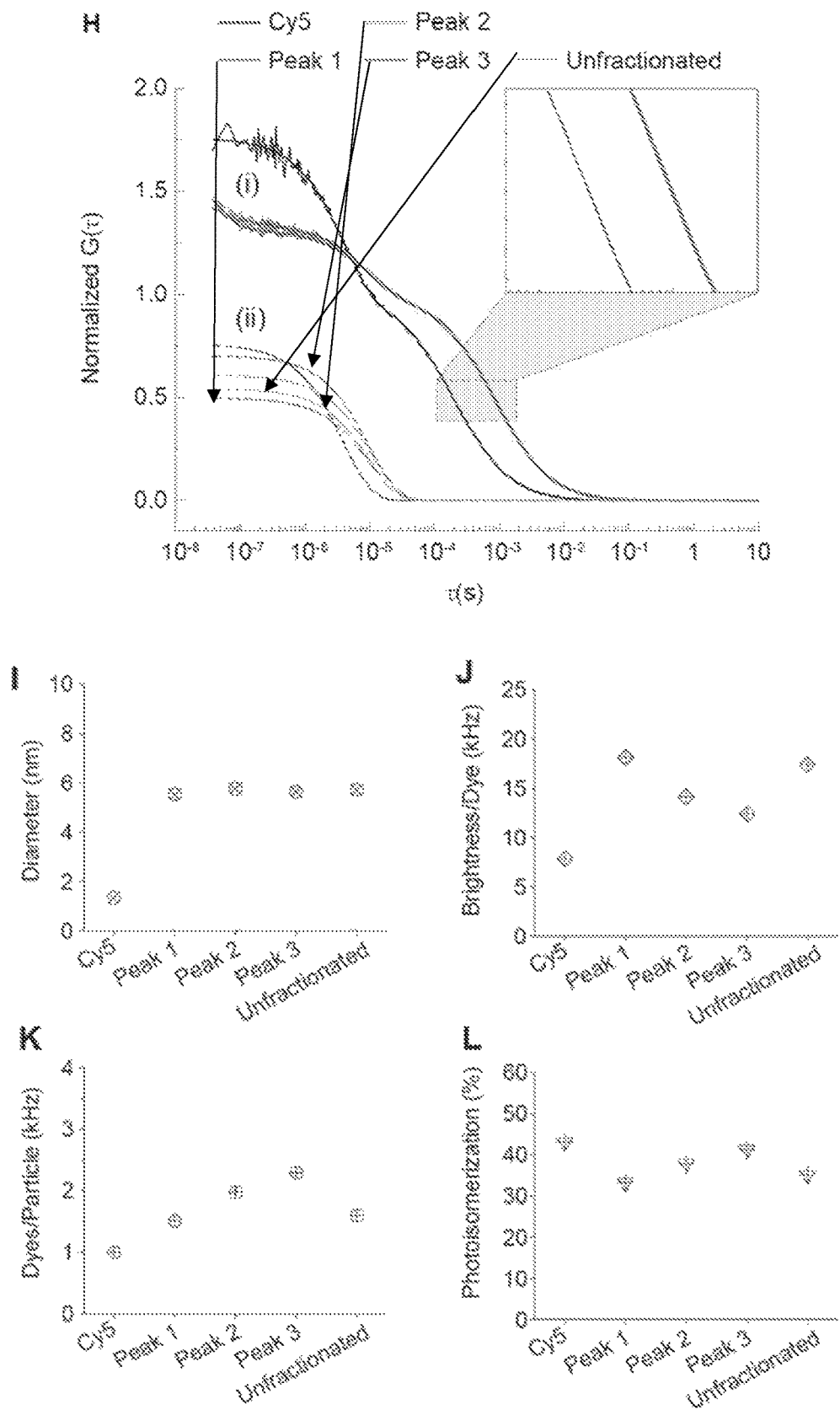

Although claimed subject matter will be described in terms of certain examples, other examples, including examples that do not provide all of the benefits and features set forth herein, are also within the scope of this disclosure. Various structural, logical, and process step changes may be made without departing from the scope of the disclosure.

The present disclosure provides methods of analyzing and/or purifying inorganic nanoparticles (e.g., core- or core-shell nanoparticles). The inorganic nanoparticles are also referred to herein as ultrasmall nanoparticles. The present disclosure also provides methods of making inorganic nanoparticles and compositions comprising inorganic nanoparticles.

All ranges provided herein include all values that fall within the ranges to the tenth decimal place, unless indicated otherwise.

In various examples, the present disclosure provides:
(1) The application of high performance liquid chromatography (HPLC) methods, which enabled the discovery of hitherto unknown surface-chemical heterogeneities in inorganic nanoparticles (e.g., fluorescent core-shell silica nanoparticles).
(2) The identification of design criteria to overcome the intrinsic nanoparticle heterogeneities observed.
(3) The discovery that fluorescent dye charge is a crucial parameter in the control of surface chemistry heterogeneity.
(4) The use of positively charged dyes, such as ATTO647N and MB2 in some embodiments to synthesize C' dots with highly homogeneous surface-chemical properties, displaying only a single peak in the HPLC analysis.
(5) These homogeneous C' dots exhibit profoundly higher stability against chemical degradation.
(6) These homogeneous C' dots exhibit profoundly higher photostability when compared to previously reported materials.

In certain examples, the present disclosure provides:
(1) Creation of an ultrasmall (sub-10 nm) nanoparticle with a completely homogeneous surface chemistry.
(2) Reduces dye sensitivity to solvent environment, normally hydrophobic dyes like ATTO647N cannot be reliably used in water-based applications.
(3) Uses for clinically relevant diagnostic imaging.
(4) Uses for improvement of bio-distribution of nanoparticle diagnostics and therapies
(5) Uses for other nanoparticles in the process of clinical translation.
(6) Useful to analyze surface chemistry engineering for PEGylated materials which was until now not straight forward.

In an aspect, the present disclosure provides the analysis and/or purification of inorganic nanoparticles via liquid chromatography. The analysis and/or purification may be carried out using HPLC and/or GPC.

Inorganic nanoparticles comprising various dye groups may be suitable for analysis and/or purification. The dye groups may be located in various locations on and/or in (encapsulated by or partially encapsulated by) an inorganic nanoparticle. The dye groups may be disposed or partially disposed on the surface of an inorganic nanoparticle, encapsulated or partially encapsulated by the inorganic nanoparticle, or a combination thereof. A dye group disposed or partially disposed on the surface of an inorganic nanoparticle may refer to the dye group being part of a PEG group disposed or partially disposed on the surface of the inorganic nanoparticle.

Inorganic nanoparticles may be analyzed by high performance liquid chromatography (HPLC). HPLC may be used to determine the location of one or more dye group on and/or in (e.g., encapsulated by) an inorganic nanoparticle. Such a method may comprise subjecting a plurality of inorganic nanoparticles to HPLC analysis.

A method of analyzing inorganic nanoparticles may comprise: (i) depositing an inorganic nanoparticle in an HPLC column comprising an input in fluid communication with a stationary phase in fluid communication with an output in fluid communication with a detector; (ii) passing a mobile phase through the HPLC column, such that the inorganic nanoparticle elutes from the column and enters the detector, such that the detector generates a signal, wherein the signal indicates the location of the one or more dye group on and/or in the nanoparticle and/or core-shell nanoparticle; and (iii) analyzing the signal to determine the location of the one or more dye group on and/or in the inorganic nanoparticle. The signal comprises a retention time that correlates to the location of one or more dye group on and/or in (e.g., encapsulated by or partially encapsulated by) an inorganic nanoparticle. A peak at a specific retention time may also correlate to the number of dye groups disposed and/or partially disposed on the exterior surface of an inorganic particle or whether dye groups are in (e.g., encapsulated by or partially encapsulated by) an inorganic nanoparticle. Methods of HPLC analysis of the present disclosure may be reproducible.

In an example, whenever eluent comprising inorganic nanoparticles passes through a detector, the detector generates a signal with an intensity greater than baseline. The relative time at which a signal occurs following the injection of a sample comprising a plurality of inorganic nanoparticles in the column determines the elution time of a portion of the plurality of inorganic nanoparticles. The elution time correlates to a portion of inorganic nanoparticles eluted from the column, with more hydrophobic particles being eluted at later times. Without intending to being bound by any particular theory, it is expected that an increasing number of hydrophobic dye group disposed on the surface of an inorganic nanoparticle increases the inorganic nanoparticle's elution time. As an illustrative example, a inorganic nanoparticle that has two hydrophobic dye groups disposed or partially disposed on the surface elutes later than an inorganic nanoparticle with only one dye disposed or partially disposed on the surface.

Various detectors are suitable for use in a method of analyzing an inorganic nanoparticle via HPLC. Examples of suitable detectors include, but are not limited to, a UV detector (e.g., a tunable UV detector), an evaporative light scattering detector, a charged aerosol detector, a fluorescence-based detector (e.g., a fluorimeter), a photodiode array detector, and the like, and combinations thereof.

Various HPLC columns are suitable for a method of analyzing an inorganic nanoparticle via HPLC. An HPLC column may be a reverse-phase HPLC column (RP-HPLC column). An RP-HPLC column may comprise a C4 stationary phase to a C8 stationary phase or other suitable moderately hydrophilic stationary phases (e.g., C4, C5, C6, C7, or C8 stationary phase). An RP-HPLC column may have various lengths. For example, a suitable RP-HPLC column is 100 to 300 mm long, including every integer mm value and range therebetween (e.g., 150-250 mm in length, such as, for example, 150 mm in length). An RP-HPLC column may have various pore sizes. For example, a suitable RP-HPLC column has a pore size of 200 to 400, including every integer Å value and range therebetween (e.g., 250 to 350, such as, for example, 300 Å). An RP-HPLC column may have various particle sizes. For example, a suitable RP-HPLC column has a particle size of 2 to 6 μm, including every 0.1 μm value and range therebetween (e.g., 3.5 to 5 μm). An RP-HPLC column may have various internal diameters. For example, an RP-HPLC may have an internal diameter of 4.6 mm. A mobile phase may be passed through an RP-HPLC column at various rates. For example, a mobile phase is passed through the column at a flow rate of 0.1 to 2.0 mL/min, including every 0.1 mL/min value and range therebetween (e.g., 0.5 to 1 mL/min). An RP-HPLC column may be maintained at various temperatures. For example, a suitable RP-HPLC column is maintained at 15 to 30° C., including every 0.1° C. value and range therebetween (e.g., 18 to 25° C.). In an example, the RP-HPLC column is not a C18 RP-HPLC column.

Various mobile phases are suitable for a method of analyzing an inorganic nanoparticle via HPLC. A mobile phase is an aqueous mobile phase, such as, for example, a water and acetonitrile mixture or a water and isopropanol and/or methanol mixture. A mobile phase may further comprise an acid, such as, for example, trifluoroacetic acid (TFA) or formic acid at a concentration of 0.01 to 1% by volume. Other suitable mobile phases are known in the art.

The mobile phase may be passed through the column in a step-like gradient. For example, a mobile phase comprising a polar portion and nonpolar portion, where polar portion exceeds the nonpolar portion (e.g., 90:10 water:acetonitrile) may be passed through an HPLC column at a flow rate of, for example, 1 mL/min. These conditions may be maintained for a period of time (e.g., 20 minutes) to allow equilibration of an analyte (e.g., an inorganic nanoparticle) with the stationary phase. After the period of time (e.g., 20 minutes) the flow rate may be decreased (e.g., to 0.5 mL/min) and the HPLC column may be allowed to equilibrate. The mobile phase composition may then be changed such that the nonpolar portion slightly exceeds the polar portion (e.g., 45:55 water:acetonitrile) in a step-like fashion and the baseline may be allowed to equilibrate again. Finally, a composition gradient of where the nonpolar portion is further increased may be used (e.g., 45:55 to 5:95 water:acetonitrile) for a period of time (e.g., 20 minutes), during which time the analyte (e.g., a selected portion of inorganic nanoparticles) elutes from the column.

A composition comprising a plurality of inorganic nanoparticles may be purified using liquid chromatography. In an example, the liquid chromatography is GPC or preparative scale HPLC (e.g., preparative-scale RP-HPLC).

Inorganic nanoparticles may be purified using gel permeation chromatography (GPC). GPC may be used to purify inorganic nanoparticles and/or determine separate batches of inorganic nanoparticles based on size.

A method of purifying inorganic nanoparticles may comprise: (i) depositing the plurality of inorganic nanoparticles in a chromatography column comprising an input in fluid communication with a stationary phase in fluid communication with an output in fluid communication with a detector; (ii) passing a mobile phase through the chromatography column, such that the plurality of inorganic nanoparticles elutes from the column; and (iii) collecting an eluent comprising the selected portion of the plurality inorganic nanoparticles.

The chromatography column may be a GPC column having a porous gel stationary phase. Other suitable stationary phases are known in the art. In an example, the mobile phase may be an aqueous mobile phase, such as, for example water, an aqueous solution of NaCl (e.g., a 0.9 wt % NaCl aqueous solution). Other suitable mobile phases are known in the art.

Inorganic nanoparticles may further be analyzed by fluorescence correlation spectroscopy (FCS) in combination with other methods, including, such as, for example, UV/VIS optical spectroscopy as well as single particle dye bleaching experiments. Analysis by FCS may be used to determine the hydrodynamic size of the nanoparticle and/or number of inorganic nanoparticles per solution volume (i.e., the inorganic nanoparticle concentration). FCS may be performed using a laser. Various lasers may be used based on the dye group(s) being analyzed. Suitable lasers include, but are not limited to, 488 nm solid state lasers (which may be suitable for RhG fluorophores), 543 HeNe lasers (which may be suitable for a TMR fluorophore), a 633 nm solid state laser (which may be suitable for Cy5 and Cy5.5 fluorophores), a 785 nm solid state laser (which may be suitable for dyes such as CW800 and Cy7.5). FCS may also be used in combination with UV/VIS optical spectroscopy as well as single-particle photobleaching experiments to determine the number of dyes per particle.

Various methods of purification and/or analysis may be combined and performed in any order. For example, a plurality of inorganic nanoparticles may first be purified by GPC, analyzed by FCS, and then analyzed by HPLC. In various examples, the purification and analysis may be performed using preparative scale HPLC, analytical scale HPLC, GPC, and the like, and combinations thereof.

Methods of purification and/or analysis may generate eluent containing a purified, an analyzed, and/or a selected portion of inorganic nanoparticles. The purified, analyzed, and/or selected portion of inorganic nanoparticles may be referred to as fractions. The fractions may be combined to generate various compositions comprising desirable combinations of inorganic nanoparticles. For example, a fraction containing a plurality of inorganic nanoparticles, where individual inorganic nanoparticles encapsulate one or more anionic dye groups, may be combined with a fraction containing a plurality of inorganic nanoparticles, where individual inorganic nanoparticles have one anionic dye group disposed or partially disposed on the exterior surface of the individual inorganic nanoparticles.

In an aspect, the present disclosure provides a method of making inorganic nanoparticles (e.g., ultrasmall nanoparticles). The methods are based on use of aqueous reaction medium (e.g. water). The nanoparticles can be surface functionalized with polyethylene glycol groups (e.g., PEGylated) and/or various dye groups. One or more dye group disposed or partially disposed on the surface of an inorganic nanoparticle may refer to the one or more dye group being disposed on PEG group(s) and/or part of PEG group(s) disposed on the inorganic nanoparticle.

The methods as described herein may be linearly scaled up (e.g., from 10 mL reaction to 1000 mL or greater) without any substantial change in product quality. This scalability may be important for large scale manufacture of the nanoparticles.

The methods may be carried out in an aqueous reaction medium (e.g., water). For example, the aqueous medium comprises water. Certain reactants may be added to the various reaction mixtures as solutions in a polar aprotic solvent (e.g., DMSO or DMF). In various examples, the aqueous medium does not contain organic solvents (e.g., alcohols such as $C_1$ to $C_6$ alcohols) other than polar aprotic solvents at 10% or greater, 20% or greater, or 30% or greater. In an example, the aqueous medium does not contain alcohols at 1% or greater, 2% or greater, 3% or greater, 4% or greater, or 5% or greater. In an example, the aqueous medium does not contain any detectable alcohols. For example, the reaction media of any of the steps of any of the methods disclosed herein consists essentially of water and, optionally, a polar aprotic solvent.

At various points in the methods the pH may be adjusted to a desired value or within a desired range. The pH of the reaction mixture can be increased by addition of a base. Examples of suitable bases include ammonium hydroxide and an ammonia in ethanol solution.

For example, a method of making inorganic nanoparticles functionalized with polyethylene glycol groups (i.e., PEGylated inorganic nanoparticles) and dye molecules comprises: a) forming a reaction mixture at room temperature (e.g., 15° C. to 25° C. depending on the location) comprising water, a silica core forming monomer (e.g., TMOS) (e.g., at a concentration of 11 mM to 270 mM), and one or more dye group precursor, wherein the pH of the reaction mixture (which can be adjusted using a base such as, for example, ammonium hydroxide) is 6 to 9 (which results in formation of core precursor nanoparticles having an average size (e.g., longest dimension) of, for example, 1 nm to 2 nm); b) either i) holding the reaction mixture at a time ($t^1$) and temperature ($T^1$) (e.g., ($t^1$) 0.5 days to 7 days at room temperature to 95° C. ($T^1$)), whereby nanoparticles (core nanoparticles) having an average size (e.g., longest dimension) of 2 to 15 nm are formed, or ii) cooling the reaction mixture to room temperature, if necessary, and adding a shell forming monomer (e.g., tetraethyl orthosilicates, other than TMOS, such as, for example, TEOS or TPOS) (the addition is carried out such that the shell forming monomer concentration is below the threshold for secondary nucleation) to the reaction mixture from a), whereby inorganic nanoparticles having an average size (e.g., longest dimension) of 2 to 50 nm (e.g., 2 to 15 nm) are formed; c) adjusting, if necessary, the pH of the reaction mixture to a pH of 6 to 10 comprising the inorganic nanoparticles from b) i) or b) ii), respectively; and d) optionally (PEGylating the inorganic nanoparticles by) adding at room temperature to the reaction mixture comprising the inorganic nanoparticles from b) i) or b) ii), respectively, a PEG-silane conjugate (comprising a PEG moiety covalently bound to a silane moiety) (e.g., at a concentration of 10 mM to 60 mM) (e.g., PEG-silane conjugate dissolved in a polar aprotic solvent such as, for example, DMSO or DMF) and holding the resulting reaction mixture at a time ($t^2$) and temperature ($T^2$) (e.g., ($t^2$) 0.5 minutes to 24 hours at room temperature ($T^2$)) (whereby at least a portion of the PEG-silane conjugate molecules are adsorbed on at least a portion of the surface of the core nanoparticles or core-shell nanoparticles from b)); e) heating the mixture from d) at a time ($t^3$) and temperature ($T^3$) (e.g., ($t^3$) 1 hour to 24 hours at 40° C. to 100° C. ($T^3$)), whereby the inorganic nanoparticles functionalized with one or more dye groups and surface functionalized with polyethylene glycol groups are formed; and f) purifying the reaction mixture containing the inorganic nanoparticles functionalized with one or more dye groups and surface functionalized with polyethylene glycol groups by liquid chromatography.

The inorganic nanoparticles may be subjected to post-synthesis processing steps. For example, after synthesis (e.g., after e) in the example above) the solution is cooled to room temperature and then transferred into a dialysis membrane tube (e.g., a dialysis membrane tube having a Molecular Weight Cut off 10,000, which are commercially available (e.g., from Pierce)). The solution in the dialysis tube is dialyzed in DI-water (volume of water is 200 times more than the reaction volume, e.g., 2000 mL water for a 10 mL reaction) and the water is changed every day for one to six days to wash away remaining reagents, e.g., ammonium hydroxide and free silane molecules. The particles are then filtered through a 200 nm syringe filter (fisher brand) to remove aggregates or dust. If desired, additional purification processes, including gel permeation chromatography and high-performance liquid chromatography, can be applied to the nanoparticles to further ensure the high purify of the synthesized particles (e.g., 1% or less unreacted reagents or aggregates). After any purification processes, the purified nanoparticles can be transferred back to deionized water if other solvent is used in the additional processes.

The cores can be silicon cores. The reaction mixture used in silicon core formation can comprise TMOS as the only silicon core forming monomer.

The cores can be aluminosilicate cores. The reaction mixture used in aluminosilicate core formation can comprise TMOS as the only silica core forming monomer and one or more alumina core forming monomer (e.g., an aluminum alkoxide such as, for example, aluminum-tri-sec-butoxide or a combination of aluminum alkoxides).

In the case of aluminosilicate core synthesis, the pH of the reaction mixture is adjusted to a pH of 1 to 2 prior to addition of the alumina core forming monomer. After aluminosilicate core formation, the pH of the solution is adjusted to a pH of 7 to 9 and, optionally, PEG with molecular weight between 100 and 1,000 g/mol, including all integer values and ranges therebetween, at concentration of 10 mM to 75 mM, including all integer mM values and ranges therebetween, is added to the reaction mixture prior to adjusting the pH of the reaction mixture to a pH of 7 to 9.

The reaction mixture used to form inorganic nanoparticles can also comprise a dye precursor (e.g., a positively charged dye precursor). In this case, the resulting core or core-shell nanoparticles have one or more dye molecules (e.g., positively charged dye molecules) encapsulated or incorporated therein. For example, core nanoparticle has 1, 2, 3, 4, 5, 6, or 7 positively charged dye molecules encapsulated therein. Mixtures of dye precursors can be used. The dye precursor (e.g., positively charged dye precursor) may be a dye (e.g., positively charged dye) conjugated to a silane. For example, a positively charged dye with maleimido functionality is conjugated to thiol-functionalized silane. In another example, a positively charged dye with NHS ester functionality is conjugated to amine-functionalized silane. Examples of suitable silanes and conjugation chemistries are known in the art. The dye can have an emission (e.g., fluorescence) wavelength of 400 nm (blue) to 900 nm (near-infrared). For example, the dye is a near infrared (NIR) dye. Examples of suitable dyes include, but are not limited to, rhodamine green (RHG), tetramethylrhodamine (TMR), Cyanine 5 (Cy5), Cyanine 5.5 (Cy5.5), Cyanine 7 (Cy7), ATTO425, ATTO647N, ATTO647, ATTO680, Dyomics DY800, Dyomics DY782 and IRDye 800CW, and the inorganic nanoparticles surface functionalized with polyethylene glycol groups may have one or more fluorescent positively charged dye molecules encapsulated therein. Examples of dyes include negatively charged dyes, such as, for example, sulfo-Cy5.5, sulfo-Cy5, sulfo-Cy3, Alexa Fluor 532, Alexa Fluor 430, ATTO430LS, ATTO488, ATTO490LS, ATTO532, ATTO594, and the like, and combinations thereof; net neutral dyes, such as, for example, tetramethylrhodamine (TMR), ATTO390, ATTO425, ATTO565, ATTO590, ATTO647, ATTO650, ATTO655, ATTO680, ATTO700, and the like, and combinations thereof; and positively charged dyes, such as, for example, Cy5.5, Cy5, Cy3, ATTO647N, methylene blue, ATTO663, ATTO620, ATTO665, ATTO465, ATTO495, ATTO520, ATTORho6G, ATTORho3B, ATTORho11, ATTORho12, ATTOThio12, ATTO580Q, ATTORho101, ATTORho13, ATTO610, ATTO612Q, ATTO647N, ATTORho14, ATTOOxa12, ATTO725, ATTO740, ATTOMB2, and the like, and combinations thereof. The dyes may have functional groups suitable for conjugation chemistry, such as, for example, carboxylic acids, NETS-esters, and the like, and may be referred to as such. In an illustrative example, Cy5-NETS-ester is the NETS ester of Cy5. The dye groups may be covalently bound to the silica matrix or aluminosilicate matrix of the inorganic nanoparticle and/or covalently bound to an exterior surface of the inorganic nanoparticle and/or are part of a PEG group.

A silica shell may be formed on core nanoparticles. The silica shell is formed after, for example, core formation is complete. Examples of silica shell forming precursors include tetraalkylorthosilicates such as, for example, TEOS and TPOS. Mixtures of silica shell forming precursors can be used. TMOS is not a silica shell forming precursor. The silica shell forming precursor can be added to the reaction mixture as a solution in a polar aprotic solvent. Examples, of suitable polar aprotic solvents include DMSO and DMF.

It is desirable to add the silica shell forming precursors in separate aliquots. For example, the shell forming monomer(s) is/are added in separate aliquots (e.g., 40 to 500 aliquots, including every integer aliquot value and range therebetween) The aliquots can include one or more shell forming precursor (e.g., TEOS and/or TPOS) and a polar aprotic solvent (e.g., DMSO). Each aliquot may have 1 to 20 micromoles of shell forming monomer, including every 0.1 micromole value and range therebetween. The interval between aliquot addition may be 1 to 60 minutes, including all integer second values and ranges therebetween. The pH of the reaction mixture can vary during the silica shell forming process. It is desirable to adjust the pH to maintain a pH of 7-8.

After inorganic nanoparticle formation, the inorganic nanoparticle can by reacted with one or more PEG-silane conjugates. Various PEG-silane conjugates can be added together or in various orders. This process is also referred to herein as PEGylation. The conversion percentage of PEG-silane is between 5% and 40% and the polyethylene glycol surface density is 1.3 to 2.1 polyethylene glycol molecules per $nm^2$. The conversion percentage of ligand-functionalized PEG-silane is 40% to 100% and the number of ligand-functionalized PEG-silane precursors reacted with each particle is 3 to 90.

PEGylation can be carried out at a variety of times and temperatures. For example, in the case of inorganic nanoparticles, PEGylation can be carried out by contacting the nanoparticles at room temperature for 0.5 minutes to 24 hours (e.g., overnight). For example, in the case of aluminosilicate nanoparticles (e.g., aluminosilicate core nanoparticles or inorganic nanoparticle) the temperature is 80° C. overnight.

The chain length of the PEG moiety of the PEG-silane (i.e., the molecular weight of the PEG moiety) can be tuned from 3 to 24 ethylene glycol monomers (e.g., 3 to 6, 3 to 9, 6 to 9, 8 to 12, or 8 to 24 ethylene glycol monomers). The PEG chain length of PEG-silane can be selected to tune the thickness of the PEG layer surrounding the particle and the pharmacokinetics (PK) and biodistributrion profiles of the PEGylated particles. The PEG chain length of ligand-functionalized PEG-silane can be used to tune the accessibility of the ligand groups on the surface of the PEG layer of the particles resulting in varying binding and targeting performance.

PEG-silane conjugates can comprise a ligand. The ligand is covalently bound to the PEG moiety of the PEG-silane conjugates. The ligand can be conjugated to a terminus of the PEG moiety opposite the terminus conjugated to the silane moiety. The PEG-silane conjugate can be formed using a heterobifunctional PEG compound (e.g., maleimido-functionalized heterobifunctional PEGs, NHS ester-functionalized heterobifunctional PEGs, amine-functionalized heterobifunctional PEGs, thiol-functionalized heterobifunctional PEGs, etc.). Examples of suitable ligands include, but are not limited to, peptides (natural or synthetic), cyclic peptides, ligands comprising a radio label (e.g., $^{124}$I, $^{131}$I, $^{225}$Ac, or $^{177}$Lu), antibodies, antibody fragments, DNA, RNA, simple sugars, oligosaccharides, drug molecules (e.g. small molecule inhibitors, toxic drugs), and ligands comprising a reactive group (e.g., a reactive group that can be conjugated to a molecule such a drug molecule, gefitinib, etc.).

For additional particle functionalization (e.g., to generate multifunctional nanoparticles) amine- and/or thiol-functionalized silane molecules may be inserted between PEG chains and onto the silica surface of inorganic nanoparticles (e.g., C' dots), to which additional functional ligands (e.g., sensor dye molecules, additional chelators for radiometals, or additional functional groups in order to add pharmaceutical compounds) can subsequently be attached. This post-PEGylation surface modification by insertion (PPSMI) approach only requires a few extra steps sandwiched between nanoparticle (e.g., C' dot) PEGylation and purification in a one-pot type water-based synthesis without diminishing high quality NP generation. The resulting nanoparticles (e.g., C' dots) with additional functionalities exhibit physicochemical properties like their size and PEG density close to clinically translated nanoparticles (e.g., C dots), opening a gate to the diversification of their clinical applications. Modification of a nanoparticle synthesis (e.g., a C' dot synthesis) enables, for example, large numbers of targeting peptides per particle, as well as a facile and versatile spectroscopic approach to quantitatively assess the specific numbers of the different surface ligands by deconvolution of absorption spectra into individual components.

For example, PEG-silane conjugate comprising a ligand is added in addition to PEG-silane (e.g., in d) in the example above). In this case, inorganic nanoparticles surface functionalized with polyethylene glycol groups and polyethylene groups comprising a ligand are formed. The conversion percentage of ligand-functionalized or reactive group-functionalized PEG-silane is 40% to 100% and the number of ligand-functionalized PEG-silane precursors reacted with each particle is 3 to 600.

For example, before or after (e.g., 20 seconds to 5 minutes before or after) the PEG-silane conjugate is added (e.g., in d) in the example above) a PEG-silane conjugate comprising a ligand (e.g., at concentration between 0.05 mM and 2.5 mM) is added at room temperature to the reaction mixture comprising the inorganic nanoparticles (e.g., from b) i) or b) ii), respectively, in the example above). The resulting reaction mixture is held at a time ($t^4$) and temperature ($T^4$) (e.g., ($t^4$) 0.5 minutes to 24 hours at room temperature ($T^4$)), where at least a portion of the PEG-silane conjugate molecules are adsorbed on at least a portion of the surface of the core nanoparticles or core-shell nanoparticles (e.g., from b) in the example above). Subsequently, the reaction mixture is heated at a time ($t^5$) and temperature ($T^5$) (e.g., ($t^5$) 1 hour to 24 hours at 40° C. to 100° C. ($T^5$)), where inorganic nanoparticles surface functionalized with polyethylene glycol groups comprising a ligand are formed. Optionally, subsequently adding at room temperature to the resulting reaction mixture comprising inorganic nanoparticles surface functionalized with polyethylene glycol groups comprising a ligand and a PEG-silane conjugate (the concentration of PEG-silane no ligand is between 10 mM and 75 mM) (e.g., PEG-silane conjugate dissolved in a polar aprotic solvent such as, for example, DMSO or DMF), holding the resulting reaction mixture at a time ($t^6$) and temperature ($T^6$) (e.g., ($t^6$) 0.5 minutes to 24 hours at room temperature ($T^6$)) (whereby at least a portion of the PEG-silane conjugate molecules are adsorbed on at least a portion of the surface of the inorganic nanoparticles surface functionalized with polyethylene glycol groups comprising a ligand, and heating the resulting mixture from at a time ($t^7$) and temperature ($T^7$) (e.g., ($t^7$) 1 hour to 24 hours at 40° C. to 100° C. ($T^7$)), whereby inorganic nanoparticles surface functionalized with polyethylene glycol groups comprising a ligand are formed.

In another example, at least a portion of or all of the PEG-silane has a reactive group on a terminus of the PEG moiety opposite the terminus conjugated to the silane moiety of the PEG-silane conjugate (is formed from a heterobifunctional PEG compound) and after formation of the inorganic nanoparticles surface functionalized with polyethylene glycol groups having a reactive group, and, optionally, polyethylene glycol groups. Optionally, polyethylene glycol groups are reacted with a second ligand (which can be the same or different than the ligand of the inorganic nanoparticles surface functionalized with polyethylene glycol groups and polyethylene glycol group comprising a ligand) functionalized with a second reactive group (which can be the same or different than the reactive group of the inorganic nanoparticles surface functionalized with polyethylene glycol groups and polyethylene glycol group comprising a ligand) thereby forming inorganic nanoparticles surface functionalized with polyethylene groups functionalized with a second ligand and, optionally, polyethylene glycol groups.

In another example, at least a portion of or all of the PEG-silane has a reactive group on a terminus of the PEG moiety opposite the terminus conjugated to the silane moiety of the PEG-silane conjugate (is formed from a heterobifunctional PEG compound) and after formation of the inorganic nanoparticles surface functionalized with polyethylene glycol groups and, optionally having a reactive group, and, optionally, polyethylene glycol groups, are reacted with a second ligand (which can be the same or different than the ligand of the inorganic nanoparticles surface functionalized with polyethylene glycol groups and polyethylene glycol group comprising a ligand) functionalized with a second reactive group (which can be the same or different than the reactive group of the inorganic nanoparticles surface functionalized with polyethylene glycol groups and polyethylene glycol group comprising a ligand) thereby forming inorganic nanoparticles surface functionalized with polyethylene groups functionalized with a second ligand and, optionally, polyethylene glycol groups, where at least a portion of the PEG-silane has a reactive group on a terminus of the PEG moiety opposite the terminus conjugated to the silane moiety of the PEG-silane conjugate (is formed from a heterobifunctional PEG compound) and after formation of the inorganic nanoparticles surface functionalized with polyethylene glycol groups having a reactive group, inorganic nanoparticles surface functionalized with polyethylene glycol groups having a reactive group and polyethylene glycol groups comprising a ligand, the reactive group are reacted with a second ligand functionalized with a reactive group (which can be the same or different than the ligand of the inorganic nanoparticles surface functionalized with polyethylene glycol groups and polyethylene glycol group comprising a ligand) thereby forming inorganic nanoparticles surface functionalized with polyethylene glycol groups and polyethylene groups functionalized with a second ligand or inorganic nanoparticles surface functionalized with polyethylene glycol groups comprising a ligand that is functionalized with the second ligand.

The inorganic nanoparticles with PEG groups functionalized with reactive groups can be further functionalized with one or more ligands. For example, a functionalized ligand can be reacted with a reactive group of a PEG group. Examples of suitable reaction chemistries and conditions for post-nanoparticle synthesis functionalization are known in the art.

The inorganic nanoparticles may have a narrow size distribution. In various examples, the nanoparticle size distribution (before or after PEGylation), not including extraneous materials such as, for example, unreacted reagents, dust particles/aggregates, is +/−5, 10, 15, or 20% of the average particle size (e.g., longest dimension). The particle size may be determined by methods known in the art. For example, the particle size is determined by TEM, GPS, or DLS. DLS contains systematic deviation and, therefore, the DLS size distribution may not correlate with the size distribution determined by TEM or GPS.

In an aspect, the present disclosure provides compositions comprising inorganic nanoparticles of the present disclosure. The compositions can comprise one or more types (e.g., having different average size and/or one or more different compositional feature).

For example, a composition comprises a plurality of inorganic nanoparticles (e.g., silica core nanoparticles, silica core-shell nanoparticles, aluminosilicate core nanoparticles, aluminosilicate core-shell nanoparticles). Any of the inorganic nanoparticles may be surface functionalized with one or more type of polyethylene glycol groups (e.g., polyethylene glycol groups, functionalized (e.g., functionalized with one or more ligand and/or a reactive group) polyethylene glycol groups, or a combination thereof). Any of the inorganic nanoparticles can have a dye group or combination of dye groups (e.g., a NIR dye, such as, for example, a positively charged NIR dye) encapsulated therein. The dye groups are covalently bound to the inorganic nanoparticles. The inorganic nanoparticles can be made by a method of the present disclosure. For example, location of the dye in and/or on the inorganic nanoparticles can be determined by the charge of the dye. The dye groups may be positively charged, negatively charged, or be net neutral.

Dye groups that are fully encapsulated in the inorganic nanoparticle remain encapsulated in inorganic nanoparticle such that no free dye leaches into the aqueous medium suspending the nanoparticles. Dye groups remain encapsulated for periods up to 6 months to 2 years (e.g., 6 months, 9 months, 12 months, 18 months, or 24 months). For example, an aqueous (e.g., water) composition comprising inorganic nanoparticles with positively charged dyes are stable for a period of up to 6 months to 2 years (e.g., 6 months, 9 months, 12 months, 18 months, or 24 months) and do not exhibit observable free dye in the aqueous medium (e.g., water) during this period. For example, the composition does not exhibit observable free dye by HPLC (e.g., an HPLC method described herein) in the aqueous medium (e.g., water) during this period.

The inorganic nanoparticles in a composition can have a variety of sizes. The inorganic nanoparticles can have a core size of 2 to 50 nm (e.g., 2 to 10 nm or 2 to 5 nm), including all 0.1 nm values and ranges therebetween. In various examples, the inorganic nanoparticles have a core size of 2, 2.5, 3, 3.5, 4, 4.5, 5, 5.5, 6, 6.5, 7, 7.5, 8, 8.5, 9, 9.5, 9.99, 10, 10.5, 11, 11.5, 12, 12.5, 13, 13.5, 14, 14.5, or 15 nm. In various examples, at least 90%, 95%, 96%, 97%, 98%, 99%, 99.5% 99.9%, or 100% of the inorganic nanoparticles have a size (e.g., longest dimension) of 2 to 50 nm (e.g., 2 to 10 nm or 2 to 5 nm). In various examples, at least 90%, 95%, 96%, 97%, 98%, 99%, 99.5% 99.9%, or 100% of the inorganic nanoparticles have a size (e.g., longest dimension) of 2 to 50 nm. For the exemplary size distributions, the composition may not be subjected to any particle-size discriminating (particle size selection/removal) processes (e.g., filtration, dialysis, chromatography (e.g., GPC), centrifugation, etc.). For example, the inorganic nanoparticles of the present disclosure are the only inorganic nanoparticles in the composition. In an example, an inorganic nanoparticle may have 0-4 shells (e.g., 0, 1, 2, 3, or 4).

The inorganic nanoparticles in a composition can have a variety of sizes. The inorganic nanoparticles can have a core size of 2 to 15 nm (e.g., 2 to 10 nm or 2 to 9.99 nm), including all 0.1 nm values and ranges therebetween. In various examples, the inorganic nanoparticles have a core size of 2, 2.5, 3, 3.5, 4, 4.5, 5, 5.5, 6, 6.5, 7, 7.5, 8, 8.5, 9, 9.5, 9.99, 10, 10.5, 11, 11.5, 12, 12.5, 13, 13.5, 14, 14.5, or 15 nm. In various examples, at least 90%, 95%, 96%, 97%, 98%, 99%, 99.5% 99.9%, or 100% of the inorganic nanoparticles have a size (e.g., longest dimension) of 2 to 15 nm (e.g., 2 to 10 nm or 2 to 9.99 nm). In various examples, at least 90%, 95%, 96%, 97%, 98%, 99%, 99.5% 99.9%, or 100% of the core-shell nanoparticles have a size (e.g., longest dimension) of 2 to 50 nm. For the exemplary size distributions, the composition may not be subjected to any particle-size discriminating (particle size selection/removal) processes (e.g., filtration, dialysis, chromatography (e.g., GPC), centrifugation, etc.). For example, the inorganic nanoparticles of the present disclosure are the only inorganic nanoparticles in the composition. In an example, an inorganic nanoparticle may have 0-4 shells (e.g., 0, 1, 2, 3, or 4).

The composition can comprise additional components. For example, the composition can also comprise a buffer suitable for administration to an individual (e.g., a mammal such as, for example, a human). The buffer may be a pharmaceutically-acceptable carrier.

The compositions, as synthesized and before any post-synthesis processing/treatment, can have inorganic nanoparticles, particles (2-15 nm, e.g., 2-10 nm, e.g., 2 to 10 nm or 2 to 5 nm), dust particles/aggregates (>20 nm), unreacted reagents (<2 nm).

A composition may comprise a plurality of inorganic nanoparticles, where the individual inorganic nanoparticles of the plurality of inorganic nanoparticles comprise 1-7 positively charged dye group(s), where: i) none of the positively charged dye groups are disposed or partially disposed on the surface of the inorganic nanoparticles; or ii) the majority (e.g., greater than 50%) of the inorganic nanoparticles have at least one (e.g., one, two, three, four, five, six, seven, or a combination thereof) positively charged dye group(s) disposed or partially disposed on the surface of the inorganic nanoparticles; or iii) all of the positively charged dye groups are disposed or partially disposed on the surface of the inorganic nanoparticles.

In an example, a composition comprising a plurality of inorganic nanoparticles, where the individual inorganic nanoparticles of the plurality of inorganic nanoparticles comprise 1-7 positively charged dye group(s) may consist essentially of individual inorganic nanoparticles having 0, 1, 2, 3, 4, 5, 6, or 7 dye groups disposed or partially disposed on the surface of the inorganic nanoparticles.

A composition may comprise a plurality of inorganic nanoparticles, where the individual inorganic nanoparticles of the plurality of inorganic nanoparticles comprise 1-7 net neutral dye group(s), where: i) none of the net neutral dye groups are disposed or partially disposed on the surface of the inorganic nanoparticles; or ii) the majority (e.g., greater than 50%) of the inorganic nanoparticles have at least one (e.g., one, two, three, four, five, six, seven, or a combination thereof) net neutral dye group(s) disposed or partially disposed on the surface of the inorganic nanoparticles; or iii) all of the net neutral dye groups are disposed or partially disposed on the surface of the inorganic nanoparticles.

In an example, a composition comprising a plurality of inorganic nanoparticles, where the individual inorganic nanoparticles of the plurality of inorganic nanoparticles comprise 1-7 net neutral dye group(s) may consist essentially of individual inorganic nanoparticles having 0, 1, 2, 3, 4, 5, 6, or 7 dye groups disposed or partially disposed on the surface of the inorganic nanoparticles.

A composition comprising a plurality of inorganic nanoparticles, where the individual inorganic nanoparticles of the plurality of inorganic nanoparticles comprise 1-7 negatively charged dye groups, where: i) none of the negatively charged dye groups are disposed or partially disposed on the surface of the inorganic nanoparticles; or ii) the majority (e.g., greater than 50%) of the inorganic nanoparticles have none of the negatively charged dye groups are disposed or partially disposed on the surface of the inorganic nanoparticles; or iii) the majority of the inorganic nanoparticles have 1, 2, 3, 4, 5, 6, or 7 of the negatively charged dye group(s) are disposed or partially disposed on the surface of the inorganic nanoparticles.

In an example, a composition comprising a plurality of inorganic nanoparticles, where the individual inorganic nanoparticles of the plurality of inorganic nanoparticles comprise 1-7 negatively charged dye group(s) may consist essentially of individual inorganic nanoparticles having 0, 1, 2, 3, 4, 5, 6, or 7 negatively charged dye groups disposed or partially disposed on the surface of the inorganic nanoparticles.

In an example, where one or more dye group is positively charged or has net neutral charge and the plurality of inorganic nanoparticles do not exhibit size-dependent surface inhomogeneity, where the size-dependent surface inhomogeneity is determined by HPLC.

In an aspect, the present disclosure provides uses of the inorganic nanoparticles and compositions of the present disclosure. For example, inorganic nanoparticles or a composition comprising the inorganic nanoparticles are used in delivery and/or imaging methods.

The ligands carried by the inorganic nanoparticles can include diagnostic and/or therapeutic agents (e.g., drugs). Examples of therapeutic agents include, but are not limited to, chemotherapeutic agents, antibiotics, antifungal agents, antiparasitic agents, antiviral agents, and combinations thereof. An affinity ligand may be also be conjugated to the nanoparticle to allow targeted delivery of the nanoparticles. For example, the inorganic nanoparticles may be conjugated to a ligand which is capable of binding to a cellular component (e.g., on the cell membrane or in the intracellular compartment) associated with a specific cell type. The targeted molecule can be a tumor marker or a molecule in a signaling pathway. The ligand can have specific binding affinity to certain cell types, such as, for example, tumor cells. In certain examples, the ligand may be used for guiding the nanoparticles to specific areas, such as, for example, liver, spleen, brain or the like. Imaging can be used to determine the location of the nanoparticles in an individual.

The inorganic nanoparticles or compositions comprising inorganic nanoparticles can be administered to individuals for example, in pharmaceutically-acceptable carriers, which facilitate transporting the inorganic nanoparticles from one organ or portion of the body to another organ or portion of the body. Examples of individuals include animals such as human and non-human animals. Examples of individuals also include mammals.

Pharmaceutically acceptable carriers are generally aqueous based. Some examples of materials which can be used in pharmaceutically-acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. (See REMINGTON'S PHARM. SCI., 15th Ed. (Mack Publ. Co., Easton (1975)).

Compositions comprising the present inorganic nanoparticles can be administered to an individual by any suitable route—either alone or as in combination with other agents. Administration can be accomplished by any means, such as, for example, by parenteral, mucosal, pulmonary, topical, catheter-based, or oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth. Transdermal delivery can include delivery via the use of dermal patches.

Following administration of a composition comprising the present inorganic nanoparticles, the path, location, and clearance of the inorganic nanoparticles can be monitored using one or more imaging techniques. Examples of suitable imaging techniques include Artemis Fluorescence Camera System.

This disclosure provides a method for imaging biological material such as cells, extracellular components, or tissues comprising contacting the biological material with inorganic nanoparticles comprising one or more positively charged dyes, or compositions comprising the nanoparticles; directing excitation electromagnetic (e/m) radiation, such as light, on to the tissues or cells thereby exciting the positively charged dye molecules; detecting e/m radiation emitted by the excited positively charged dye molecules; and capturing and processing the detected e/m radiation to provide one or more images of the biological material. One or more of these steps can be carried out in vitro or in vivo. For example, the cells or tissues can be present in an individual or can be present in culture. Exposure of cells or tissues to e/m radiation can be effected in vitro (e.g., under culture conditions) or can be effected in vivo. For directing e/m radiation at cells, extracellular materials, tissues, organs and the like within an individual or any portion of an individual's body that are not easily accessible, fiber optical instruments can be used.

For example, a method for imaging of a region within an individual comprises (a) administering to the individual inorganic nanoparticles or a composition of the present disclosure comprising one or more positively charged dye molecules; (b) directing excitation light into the subject, thereby exciting at least one of the one or more positively charged dye molecules; (c) detecting excited light, the detected light having been emitted by said positively charged dye molecules in the individuals as a result of excitation by the excitation light; and (d) processing signals corresponding to the detected light to provide one or more images (e.g. a real-time video stream) of the region within the subject.

Since the fluorescent particles are brighter than free dye, fluorescent particles can be used for tissue imaging, as well as to image the metastasis tumor. Additionally or alternatively, radioisotopes can be further attached to the ligand groups (e.g., tyrosine residue or chelator) of the ligand-functionalized particles or to the silica matrix of the PEGylated particles without specific ligand functionalization for photoinduced electron transfer imaging. If the radioisotopes are chosen to be therapeutic, such as $^{225}$Ac or $^{177}$Lu, this in turn would result in particles with additional radiotherapeutic properties.

For example, drug-linker conjugate, where the linker group can be specifically cleaved by enzyme or acid condition in tumor for drug release, can be covalently attached to the functional ligands on the particles for drug delivery. For example, drug-linker-thiol conjugates can be attached to maleimido-PEG-particles through thiol-maleimido conjugation reaction post the synthesis of maleimido-PEG-particles. Additionally, both drug-linker conjugate and cancer targeting peptides can be attached to the particle surface for drug delivery specifically to tumor.

The steps of the method described in the various embodiments and examples disclosed herein are sufficient to carry out the methods and produce the compositions of the present disclosure. Thus, in an embodiment, the method consists essentially of a combination of the steps of the methods disclosed herein. In another embodiment, the method consists of such steps.

In the following Statements, various examples of the methods and compositions of the present disclosure are described:

Statement 1. A method of determining the location of one or more dye on and/or in an inorganic nanoparticle comprising a polyethylene glycol layer, comprising subjecting the nanoparticle or core-shell nanoparticle to high performance liquid chromatography (HPLC) analysis.

Statement 2. A method according to Statement 1 for determining the location of one or more dye on and/or in a inorganic nanoparticle, comprising: depositing the inorganic nanoparticle in an HPLC column comprising an input in fluid communication with a stationary phase in fluid communication with an output in fluid communication with a detector; passing a mobile phase through the HPLC column, such that the inorganic nanoparticle elutes from the column and enters the detector, such that the detector generates a signal, where the signal indicates the location of the one or more dye on and/or in the nanoparticle and/or core-shell nanoparticle; and analyzing the signal to determine the location of the one or more dye on and/or in the inorganic nanoparticle.

Statement 3. A method according to Statement 2, where the signal comprises an elution time and the elution time correlates to the location of one or more dye on and/or in an inorganic nanoparticle.

Statement 4. A method according to Statement 2 or Statement 3, where the HPLC column is a reverse phase HPLC (RP-HPLC) column.

Statement 5. A method according to any one of the preceding Statements, where the stationary phase is a C4 to C8 functionalized silica.

Statement 6. A method according to any one of the preceding Statements, where the mobile phase comprises water.

Statement 7. A method according to Statement 6, where the mobile phase further comprises acetonitrile.

Statement 8. A method according to Statement 6, where the mobile phase further comprises methanol and/or isopropanol.

Statement 9. A method according to any one of the preceding Statements, further comprising utilizing gel permeation chromatography (GPC).

Statement 10. A method according to Statement 9, further comprising utilizing fluorescence correlation spectroscopy (FCS) to determine the number of dyes and/or inorganic nanoparticles.

Statement 11. A method for purifying a plurality of inorganic nanoparticles comprising subjecting the plurality of inorganic nanoparticles to liquid chromatography and selecting a portion of the plurality of inorganic nanoparticles.

Statement 12. A method according to Statement 11, further comprising identifying the selected portion of the plurality of inorganic nanoparticles.

Statement 13. A method according to Statement 11 or Statement 12, where the liquid chromatography comprises: depositing the plurality of inorganic nanoparticles in a chromatography column comprising an input in fluid communication with a stationary phase in fluid communication with an output in fluid communication with a detector; passing a mobile phase through the chromatography column, such that the plurality of inorganic nanoparticles elutes from the column; and collecting an eluent comprising the selected portion of the plurality inorganic nanoparticles.

Statement 14. A method according to any one of Statements 11-13, where the chromatography column is a GPC column.

Statement 15. A method according to any one of Statements 11-14, further comprising analyzing the selected portion of the plurality of nanoparticles or core-shell nanoparticles by FCS.

Statement 16. A method according to any one of Statements 11-15, further comprising analyzing the selected portion of the plurality of inorganic nanoparticles by HPLC.

Statement 17. A method according to any one of Statements 11-16, where analyzing the selected portion of the plurality of nanoparticles or core-shell nanoparticles by HPLC comprises collecting a fraction of the eluent comprising the selected portion of plurality of nanoparticles or core-shell nanoparticles.

Statement 18. A method according to Statement 17, where two or more fractions of the eluent comprising the selected portion of plurality of nanoparticles or core-shell nanoparticles are combined.

Statement 19. A method for synthesizing an inorganic nanoparticle comprising one or more dyes and surface functionalized with polyethylene glycol (PEG) groups, comprising a) forming a reaction mixture at room temperature comprising water, TMOS, and a dye precursor, where the pH of the reaction mixture is 6 to 9; b) either i) holding the reaction mixture at a time ($t^1$) and temperature ($T^1$), whereby inorganic nanoparticles having an average size of 2 to 15 nm are formed, or ii) cooling the reaction mixture to room temperature, if necessary, and adding a shell forming monomer to the reaction mixture from a), whereby inorganic nanoparticles have a core size of 2 to 15 nm and/or an average size of 2 to 50 nm are formed; c) adjusting, if necessary, the pH of the reaction mixture to a pH of 6 to 10 comprising the inorganic nanoparticles from b) i) or b) ii), respectively; d) adding at room temperature to the reaction mixture comprising the inorganic nanoparticles from b) i) or b) ii), respectively, a PEG-silane conjugate and holding the resulting reaction mixture at a time ($t^2$) and temperature ($T^2$); e) heating the mixture from d) at a time ($t^3$) and temperature ($T^3$), whereby the inorganic nanoparticles surface functionalized with PEG groups are formed; f) purifying the reaction mixture by liquid chromatography.

Statement 20. A method according to Statement 19, where purifying comprises isolating a selected portion of a plurality of inorganic nanoparticles from the reaction mixture.

Statement 21. A method according to Statement 19 or Statement 20, further comprising analyzing the selected portion of the plurality of inorganic nanoparticles via GPC.

Statement 22. A method according to any one of Statements 19-21, further comprising analyzing the selected portion of the plurality of inorganic nanoparticles via HPLC.

Statement 23. The method according to any one of Statements 19-22, where the purification step comprises: depositing a plurality of inorganic nanoparticles in a chromatography column comprising an input in fluid communication with a stationary phase in fluid communication with an output in fluid communication with a detector, and passing a mobile phase through the chromatography column, such that the plurality of inorganic nanoparticles elutes from the column; collecting an eluent comprising the selected portion of the plurality of inorganic nanoparticles.

Statement 24. A method according to Statement 22, comprising depositing the selected portion of the plurality of inorganic nanoparticles in an HPLC column comprising an input in fluid communication with a stationary phase in fluid communication with an output in fluid communication with a detector; passing a mobile phase through the HPLC column, such that the selected portion of the plurality of inorganic nanoparticles elutes from the column and enters the detector, such that the detector generates a signal, where the signal indicates the location of the one or more dye on and/or in the individual inorganic nanoparticles of the selected portion of the plurality of the inorganic nanoparticles; analyzing the signal to determine the location of the one or more dye on and/or in the individual inorganic nanoparticles of the selected portion of the plurality of inorganic nanoparticles; and optionally, collecting one or more fraction of the eluent.

Statement 25. A method according to any one of Statements 19-24, where the reaction mixture further comprises alumina or aluminosilicate core monomer and the pH of the reaction mixture is adjusted to a pH of 1 to 2 prior to addition of the alumina or aluminosilicate core forming monomer and, optionally, PEG is added to the reaction mixture prior to adjusting the pH to a pH of 7 to 9, and the core is an aluminosilicate core.

Statement 26. A method according to any one of Statements 19-25, where the dye precursor is a positively charged dye precursor, a negatively charged dye precursor, or a net neutral dye precursor.

Statement 27. A method according to Statement 26, where the positively charged dye precursor is formed from a positively charged dye chosen from Cy5.5, Cy5, Cy3, ATTO647N, methylene blue, ATTO663, ATTO620, ATTO665, ATTO465, ATTO495, ATTO520, ATTORho6G, ATTORho3B, ATTORho11, ATTORho12, ATTOThio12, ATTO580Q, ATTORho101, ATTORho13, ATTO610, ATTO612Q, ATTO647N, ATTORho14, ATTOOxa12, ATTO725, ATTO740, ATTOMB2, and combinations thereof.

Statement 28. A method according to Statement 26, where the negatively charged dye precursor is formed from a negatively charged dye chosen from sulfo-Cy5.5, sulfo-Cy5, sulfo-Cy3, Alexa Fluor 532, Alexa Fluor 430, ATTO430LS, ATTO488, ATTO490LS, ATTO532, ATTO594, and combinations thereof.

Statement 29. A method according to Statement 26, where the net neutral dyes precursor is formed from a net neutral dye chosen from tetramethylrhodamine (TMR), ATTO390, ATTO425, ATTO565, ATTO590, ATTO647, ATTO650, ATTO655, ATTO680, ATTO700, and combinations thereof.

Statement 30. A composition comprising a plurality of inorganic nanoparticles, where the individual inorganic nanoparticles of the plurality of inorganic nanoparticles comprise 1-7 dye group(s), where: i) none of the dye groups are disposed or partially disposed on the surface of the inorganic nanoparticles; or ii) the majority (e.g., greater than 50%) of the inorganic nanoparticles have at least one (e.g., one, two, three, four, five, six, seven, or a combination thereof) dye group(s) disposed or partially disposed on the surface of the inorganic nanoparticles; or iii) all of the dye groups are disposed or partially disposed on the surface of the inorganic nanoparticles, where the dye group is positively charged.

Statement 31. A composition according to Statement 30, where the plurality of inorganic nanoparticles consists essentially of individual inorganic nanoparticles having 0, 1, 2, 3, 4, 5, 6, or 7 dye groups disposed or partially disposed on the surface of the inorganic nanoparticles.

Statement 32. A composition comprising a plurality of inorganic nanoparticles, where the individual inorganic nanoparticles of the plurality of inorganic nanoparticles comprise 1-7 dye group(s), where: i) none of the dye groups are disposed or partially disposed on the surface of the inorganic nanoparticles; or ii) the majority (e.g., greater than 50%) of the inorganic nanoparticles have at least one (e.g., one, two, three, four, five, six, seven, or a combination thereof) dye group(s) disposed or partially disposed on the surface of the inorganic nanoparticles; or iii) all of the dye groups are disposed or partially disposed on the surface of the inorganic nanoparticles, where the dye group is negatively charged Statement 33. A composition according to Statement 32, where the plurality of inorganic nanoparticles consists essentially of individual inorganic nanoparticles having 0, 1, 2, 3, 4, 5, 6, or 7 dye groups disposed or partially disposed on the surface of the inorganic nanoparticles.

Statement 34. A composition comprising a plurality of inorganic nanoparticles, where the individual inorganic nanoparticles of the plurality of inorganic nanoparticles comprise 1-7 dye group(s), where: i) none of the dye groups are disposed or partially disposed on the surface of the inorganic nanoparticles; or ii) the majority (e.g., greater than 50%) of the inorganic nanoparticles have at least one (e.g., one, two, three, four, five, six, seven, or a combination thereof) dye group(s) disposed or partially disposed on the surface of the inorganic nanoparticles; or iii) all of the dye groups are disposed or partially disposed on the surface of the inorganic nanoparticles, where the dye group is a net neutral charge.

Statement 35. A composition according to Statement 34, where the plurality of inorganic nanoparticles consists essentially of individual inorganic nanoparticles having 0, 1, 2, 3, 4, 5, 6, or 7 dye groups disposed or partially disposed on the surface of the inorganic nanoparticles.

Statement 36. A composition according to Statement 30, Statement 31, Statement 34, or Statement 35, where the one or more dye group is positively charged or has net neutral charge and the plurality of inorganic nanoparticles do not exhibit size-dependent surface inhomogeneity.

Statement 37. A composition according to Statement 36, where size-dependent surface inhomogeneity is determined by HPLC.

The following examples are presented to illustrate the present disclosure. They are not intended to limiting in any matter.

Example 1

The following in an example of synthesis and characterization of nanoparticles of the present disclosure.

Ultrasmall fluorescent silica nanoparticles (SNPs) and core-shell SNPs surface functionalized with polyethylene glycol (PEG), specific surface ligands, and overall SNP size in the regime below 10 nm are of rapidly increasing interest for clinical applications due to their favorable biodistribution and safety profiles. Herein, an aqueous synthesis methodology for the preparation of narrowly size-dispersed SNPs and core-shell SNPs with size control below 1 nm (e.g., at the level of a single atomic layer) is presented. Different types of fluorophores, including near infrared (NIR) emitters, can be covalently encapsulated. Brightness can be enhanced via addition of extra silica shells. This methodology further enables synthesis of <10 nm sized fluorescent core and core-shell SNPs with previously unknown compositions. In particular addition of an aluminum sol-gel precursor leads to fluorescent aluminosilicate nanoparticles (ASNPs) and core-shell ASNPs. Encapsulation efficiency and brightness of highly negatively charged NIR fluorophores is enhanced relative to the corresponding SNPs without aluminum. Resulting particles show quantum yields of ~0.8 (e.g., starting to approach the theoretical brightness limit). All particles may be PEGylated providing steric stability. Finally, heterobifunctional PEGs can be employed to introduce ligands onto the PEGylated particle surface of fluorescent SNPs, core-shell SNPS, and their aluminum containing analogues, producing ligand functionalized <10 nm NIR fluorescent nanoprobes. In order to distinguish these water based synthesis derived materials from the earlier alcohol-based modified Stöber process derived fluorescent core-shell SNPs referred to as Cornell dots or C dots, the SNPs and ASNPs described here and synthesized in water will be referred to as Cornell prime dots or C' dots and AlC' dots. These organic-inorganic hybrid nanomaterials may find applications in nanomedicine, including cancer diagnostics and therapy (theranostics).

The results of synthesis studies of ultrasmall SNPs using water as the reaction medium are presented. Combining fast hydrolysis, slow condensation and efficient PEG-silane induced termination of particle growth, precise size control of ultrasmall, <10 nm diameter, SNPs in steps below 1 nm, with narrow particle size distributions is demonstrated. By co-condensing different silane-conjugated fluorophores into the silica matrix this synthesis process can be used to produce <10 nm diameter fluorescent SNPs with optical characteristics tuned from the visible into the NIR part of the optical spectrum. Additional silica shells can be added to the synthesis protocol while keeping the overall particle diameter below 10 nm. This core-shell architecture leads to improved fluorescence brightness as compared to the parent cores. The water based synthesis approach is quite versatile and enables previously unknown inorganic compositions of the particles, without loss of particle size control. To that end as an example silica and mixed compositions derived from the addition of aluminum alkoxides as sol-gel precursors are investigated. The resulting growth conditions of these mixed inorganic NPs allow for more efficient incorporation of highly negatively charged NIR emitting fluorophores as compared to the plain silica based particles. At the same time the resulting NPs show enhanced quantum efficiency of encapsulated dye as compared to particles synthesized without the aluminum alkoxide addition. These aluminum containing fluorescent SNPs will be referred to as AlC' dots. Fluorescent SNPs, core-shell SNPs, and their aluminum containing analogues are PEGylated to provide steric stability. Finally, heterobifunctional PEGs are employed to introduce ligands onto the PEGylated particle surface of fluorescent SNPS and core-shell SNPS, as well as their aluminum containing analogues, producing ligand functionalized <10 nm NIR fluorescent nanoprobes for preclinical and clinical use in diagnostic and therapeutic applications. This is demonstrated using $\alpha_v\beta_3$ integrin-targeting cyclo (arginine-glycine-aspartic acid-D-tyrosine-cysteine), c(RGDyC) peptides used in earlier studies to target melanoma tumor in animal models and a first human clinical trial Besides the ability to synthesize size controlled and highly fluorescent silica-based nanoprobes for biotechnological and clinical applications, comparison of water-based particle growth pathways with those of the conventional Stöber process may contribute to a better fundamental understanding of the exact formation mechanisms of SNPs and other silica-based nanomaterials.

Experimental Section

Materials. All chemicals were used as received. Dimethyl sulfoxide (DMSO), isopropanol, (3-mercaptopropyl) trimethoxysilane (MPTMS), (3-Aminopropyl)triethoxysilane (APTES), tetramethyl orthosilicate (TMOS), tetraethyl orthosilicate (TEOS), polyethylene glycol chains (PEG, molar mass around 400), aluminum-tri-sec-butoxide, 2.0 M ammonia in ethanol and 27 wt % ammonium hydroxide are purchased from Sigma Aldrich. Methoxy-terminated poly (ethylene glycol) chains (PEG-silane, molar mass around 500) are purchased from Gelest. Heterobifunctional PEGs with maleimide and NHS ester groups (mal-PEG-NHS, molar mass around 800) are purchased from Quanta BioDesign. Acetic acid is purchased from Mallinckrodt. Cy5 and Cy5.5 florescent dyes are purchased from GE. Rhodamine green (RhG) and tetramethylrhodamine (TMR) fluorescent dyes are purchased from Life Technologies. DY782 florescent dye is purchased from Dyomics and CW800 florescent dye is purchased from Li-cor. Absolute anhydrous 99.5% ethanol is purchased from Pharmco-Aaper. Cyclo (Arg-Gly-Asp-D-Tyr-Cys) peptide, c(RGDyC), is purchased from Peptide International. Deionized water (DI water) is generated using a Millipore Milli-Q system.

When reaction conditions are listed as occurring overnight, the time the reaction can occur can range from about 8 hours to about 24 hours or even greater.

Synthesis of sub-10 nm PEGylated silica nanoparticles. For the synthesis of 4.2 nm PEGylated silica nanoparticles (SNPs), 1 mL of 0.02 M ammonia aqueous solution, which was prepared by mixing 100 μL of 2.0 M ammonia in ethanol and 10 mL Di water, was added into 9 mL of DI water (resulting concentration of ammonia hydroxide 0.002 M, see Table 1). The solution was stirred at room temperature for 10 minutes and 0.43 mmol of TMOS was then added under vigorous stirring (resulting concentration of TMOS 0.043 M, see Table 1) and the solution was stirred at room temperature overnight (12-24 hours). Following that, 0.21 mmol of PEG-silane was added and the solution was stirred at room temperature overnight (12-24 hours). In the next step, the temperature was increased to 800° C. and stirring is stopped. The solution was then left static at 800° C. overnight. Afterwards, the solution was cooled to room temperature and then transferred into a dialysis membrane tube (Pierce, Molecular Weight Cut off 10.000). The solution in the dialysis tube was dialyzed in 2000 mL DI-water and the water was changed every day for six days to wash away any remaining reagents. The particles were then filtered through a 200 nm syringe filter (Fisher brand) to remove any aggregates or dust present in the particle solution. The resulting particle solution was then subjected to long term storage at room temperature and characterization including TEM, DLS, TGA and NMR. The molar ratios of the reaction were 1 TMOS:0.093 ammonia:0.49 PEG-silane:1292 $H_2O$. Particles size was varied by tuning synthesis conditions. Details are summarized in Table 1.

TABLE 1

Synthesis condition of particles with different size.

| DLS Diameter | Temperature | Concentration of TMOS | Concentration of Ammonia hydroxide | Particle Growth Period |
|---|---|---|---|---|
| 2.4 nm | RT | 0.011M | 0.002M | 20 hrs |
| 3.1 nm | RT | 0.022M | 0.002M | 20 hrs |
| 3.7 nm | RT | 0.043M | 0.002M | 10 mins |
| 4.2 nm | RT | 0.043M | 0.002M | 20 hrs |
| 4.5 nm | RT | 0.043M | 0.02M | 20 hrs |
| 5.2 nm | RT | 0.043M | 0.06M | 20 hrs |
| 5.9 nm | 50 | 0.043M | 0.002M | 20 hrs |
| 6.5 nm | 65 | 0.043M | 0.002M | 20 hrs |
| 7.3 nm | 80 | 0.043M | 0.002M | 20 hrs |

Note that the same particles with the same size dispersity and structure control can also be synthesized using a 27 wt % ammonium hydroxide solution instead of the 2.0 M ammonia in ethanol as the ammonium hydroxide source as long as the solution pH is tuned to around 8. This indicates that the key to this C' dot particle synthesis is the correct pH plus water environment for optimized silica reaction kinetics. Small contamination of ethanol (around 10 µL ethanol in a 10 mL reaction) did not have any detectable effect in the particle synthesis as it does not appear to greatly disturb the reaction kinetics.

Synthesis of sub-10 nm PEGylated fluorescent silica nanoparticles. Cy5, Cy5.5, RhG, TMR, DY782, and CW800 dyes with maleimido functionality are first conjugated to MPTMS in DMSO with a molar ratio fluorophore: MPTMS=1:25. The silane-conjugated fluorophore was then added together with TMOS into the synthesis solution to co-condense into the particles. The molar ratio of silane-conjugated fluorophore to TMOS is around 1:1000. The remainder of the synthesis protocol was the same as described for the synthesis of the 4.2 nm particles.

In order to obtain the most precise fluorescence characterization of the fluorescent particles, any fluorophore-labeled particles prepared herein were further purified by GPC after the filtration step to further remove any remaining free dye molecules, which could disturb FCS and emission spectra measurements, and to maximize the fluorescent particle product purity. In detail, the cleaned particle solution was concentrated by about 30 times using spin-filters (GE healthcare Vivaspin with MWCF 30 k) and then purified by GPC column. Since the solvent used in the GPC setup is a 0.9 wt % NaCl solution, the purified particles are finally transferred back to DI water using spin-filters for further characterizations and long-term storage. In order to transfer the particles back to DI water, the purified particles were first concentrated by 30 times using spin-filters (GE healthcare Vivaspin with MWCF 30 k). DI water was then added into the concentrated particle solution to dilute it back to the normal volume. This process was repeated at least 8 times to decrease the concentration of NaCl to close to zero. The purified particle sample was then subjected to long-term storage at 40° C. and for further characterizations.

Synthesis of sub-10 nm PEGylated core-shell silica nanoparticles and sub-10 nm PEGylated fluorescent core-shell silica nanoparticles. The synthesis protocol for PEGylated core-shell SNPs is the same as that for the synthesis of the 4.2 nm particles except a shell addition step was added after the formation of the particles and before the addition of PEG-silane. One day after the addition of TMOS (and silane-conjugated fluorophore for the synthesis of PEGylated fluorescent core-shell SNPs) the reaction was cooled down to room temperature if a temperature above room temperature was applied for core particle formation (see Table 1).

The solution was then diluted 5 times with DI water. After that, a mixture of TEOS and DMSO (volume ratio 1:4) was dosed into the solution under vigorous stirring at room temperature. The volume of each dose was 10 µL and the time gap between doses was 30 minutes. 50 doses were added for the addition of one layer of silica shell resulting in a shell thickness close to 0.5 nm (particle size increase by around 1 nm). This process was repeated until the desired layers of shells (e.g., 1-4) were added. During the shell addition, the solution pH decreased as the result of the addition of extra TEOS and the formation of silicic acid. To keep the pH at neutral for optimized reaction kinetics, around 2 mL of 0.02 M ammonium hydroxide solution was further added into the reaction solution after the deposition of every two layers of silica shell. Afterwards, 1.05 mmol of PEG-silane (same PEG-silane concentration as the PEGylation of core particles) was added and 800° C. heat treatment was applied following the same procedure as described for the 4.2 nm particle synthesis. Purification steps were applied as described above.

Synthesis of sub-10 nm PEGylated aluminosilicate nanoparticles and PEGylated aluminosilicate core-silica shell aluminosilicate nanoparticles. For the synthesis of sub-10 nm PEGylated aluminosilicate nanoparticles (ASNPs), 1 mL of 0.5 N HCl solution was added into 9 mL of DI water and the solution was stirred for 10 minutes. Following that, 0.43 mmol of TMOS and 0.043 mmol of aluminum-tri-sec-butoxide (dissolved in isopropanol with volume ratio 1:9) were added under vigorous stirring at room temperature. 10-15 minutes later, 0.21 mmol PEG-silane was added followed by switching back of solution pH to neutral via adding about 140 µL of 27 wt % ammonium hydroxide. The final pH was double checked with pH paper. Afterward, the solution was kept at 800° C. overnight without stirring. The remainder of the synthesis protocol follows the same procedures as described for the synthesis of 4.2 nm particles.

For the synthesis of core-shell ASNPs, 0.21 mmol PEG (molecular mass around 400) was added instead of PEG-silane before the reaction pH is switched back to neutral. After the reaction pH was switched back to neutral, a mixture of TEOS and DMSO (volume ratio 1:8) was dosed into the solution under vigorous stirring at room temperature. The volume of each dose was 10 µL and the time gap between doses was 30 minutes. 50 doses were added for the addition of one layer of silica shell resulting in a shell thickness close to 0.5 nm (particle size increase by around 1 nm). This process was repeated until the desired layers of shells (e.g., 2) were added. Afterwards, 0.21 mmol PEG-silane was added and the 800° C. heat treatment is applied without stirring. The remainder of the synthesis protocol followed the same procedures as described for the synthesis of 4.2 nm particles. The addition of PEG-silane before switching solution pH back to neutral was not necessary, but this can improve the monodispersity of synthesized ASNPs and prevent their aggregation during the process of changing pH.

Synthesis of sub-10 nm PEGylated fluorescent aluminosilicate nanoparticles and sub-10 nm PEGylated fluorescent aluminosilicate core-silica shell aluminosilicate nanoparticles covalently encapsulating Cy5 or Cy5.5 fluorophores. In order to covalently encapsulate fluorophores into ASNPs, silane-conjugated Cy5 or Cy5.5 fluorophore was added right after the addition of TMOS and aluminum-tri-sec-butoxide using the same conjugation conditions and dye concentration as described herein. The remainder of the synthesis protocol was the same as described for the synthesis of blank ASNPs and purification steps were applied as described above.

PEGylated particle surface modification with easily accessible ligands. In order to functionalize the surface of any of the PEGylated particles described here with, for example, c(RGDyC) peptide ligands, the heterobifunctional NHS-PEG-mal was first conjugated with APTES in DMSO to produce mal-PEG-silane. The concentration of NHS-PEG-mal in DMSO was around 0.22 M. The reaction mixture was left at room temperature under nitrogen overnight. As the next step c(RGDyC) was then added into the DMSO solution and the solution was left at room temperature under nitrogen overnight. The molar ratio of c(RGDyC):NHS-PEG-mal:APTES is 1.1:1.0:0.9 to ensure every heterobifunctional PEG condensed on the particle surface has c(RGDyC) attached. Afterwards, the produced c(RGDyC)-PEG-silane was added followed by the addition of PEG-silane in the PEGylation step during nanoparticle synthesis. Different molar ratios of c(RGDyC)-PEG-silane: PEG-silane can be used to vary the amount of ligands on the particle surface. For example, a molar ratio of c(RGDyC)-PEG-silane:PEG-silane of about 1:40 gives around 22 c(RGDyC) ligands per 7 nm diameter particle, while decreasing the ratio to 1:400 will result in about 5 c(RGDyC) ligands per 7 nm particle. The remainder of the synthesis is the same as that described for the conventional PEGylation. The same methodology can be applied to all particles described herein for producing surface functionalized probes, including blank and fluorescent SNPs, core-shell SNPS, and their aluminum containing analogues, all with different types of covalently encapsulated fluorophores. Other ligands that can be used in this way include, but are not limited to, other linear and cyclic peptides, antibody fragments, various DNA and RNA segments (e.g. siRNA), therapeutic molecules including drugs and radioisotopes and their respective chelating moieties, as well as combinations thereof.

Gel permeation chromatography characterization (GPC). GPC characterization was performed using a BioLogic LP system equipped with a 275 nm UV detector and with resin Superdex 200 from GE healthcare. While the blank SNPs can hardly be detected by the 275 nm UV detector due to the low absorbance of silica, the fluorescent SNPs show strong signals in the GPC setup because the encapsulated fluorophores have absorbance overlapping with the 275 nm detecting channel. As a result, GPC can be used to further increase the purity of cleaned C' dot products for characterization and further clinical applications. Before usage, the GPC system was calibrated by protein standards from Bio-Rad, which were a mixture of thyroglobulin, bovine γ-globulin, chicken ovalbumin, equine myoglobin, and vitamin B12 with known molar masses. Afterwards, around 400 μL of particle solution was injected into the GPC setup and fractions were collected by a BioFrac fraction collector. A detailed analysis of different GPC factions is displayed in FIG. 15. By collecting the particle factions, the particle product purity can be further maximized.

Characterization of particle morphology. Transmission electron microscopy (TEM) images were taken using a FEI Tecnai T12 Spirit microscope operated at an acceleration voltage of 120 kV. Hydrodynamic particle sizes and size distributions were measured by dynamic light scattering (DLS) using a Malvern Zetasizer Nano-SZ operated at 200° C. Each DLS sample was measured three times and results were superimposed in the respective figures herein. Number percentage curves were used to present the measurement results. The average diameter of each sample was calculated by averaging the mean diameters of number percentage curves from three measurements.

Characterization of fluorophore encapsulating particles. Absorbance spectra of samples were measured by a Varian Cary 5000 spectrophotometer. By varying sample concentration, the absorbance spectra of different samples were matched and thus the optical density of different samples were adjusted to be the same. Afterwards, the absorbance-matched samples were subjected to emission scans using a Photon Technologies International Quantamaster spectrofluorometer. The peak intensity of emission spectra of particles was divided by the peak intensity of the absorption-matched solution of free dye for quantum efficiency enhancement calculations.

Fluorescent auto-correlation spectroscopy (FCS) measurements were conducted using an FCS setup. A 488 nm solid-state laser was used as the laser source for RhG fluorophore. A 543 nm HeNe laser was used as the laser source for TMR fluorophore. A 633 nm solid-state laser was used as the laser source for Cy5 and Cy5.5 fluorophores. A 785 nm solid-state laser was used as the laser source for DY782 and CW800 fluorophores. The hydrodynamic size, brightness per particle and particle concentration are obtained from fits of the FCS auto-correlation curves. Dividing particle concentration obtained from FCS by fluorophore concentration obtained from absorbance measurements, the number of fluorophores per particle is calculated as described.

$^{29}$Si and $^{27}$Al solid state NMR characterization. The $^{29}$Si cross-polarization (CP)/magic angle spinning (MAS) NMR experiments were carried out on a Bruker Advance NMR spectrometer with a 9.4T magnet using a probe head for rotors of 4 mm diameter. During the $^{29}$Si CP/MAS NMR experiments the samples were spun at 7.00 kHz rotation frequency at the magic angle. For the final spectra, up to 3200 scans were accumulated using CP with ramped proton powers during the 5 ms CP contact times and detection with TPPM proton decoupling. The $^{29}$Si CP/MAS NMR scans were accumulated with repetition time of 3 s due to the probe duty cycle.

The $^{27}$Al NMR experiments were performed on a Bruker Avance NMR spectrometer with a 16.45T magnet (182.47 MHz $^{27}$Al Larmor frequency) using a probe head for rotors of 2.5 mm diameter. Potassium alum serves as external $^{27}$Al NMR chemical shift secondary reference (at −0.033 ppm) and for calibration of the 90 degree pulse lengths and rf power. The final $^{27}$Al NMR MAS spectra were acquired with a nominally 10 degree direct excitation pulse at 95 kHz rf field strength, adding up to 6144 scans with 100 ms repetition times, while spinning the sample at 15.00 kHz at the magic angle. The $^{27}$Al background of the probe head and rotor were characterized by acquiring the spectrum of an empty rotor under identical conditions and subtracting it from the sample spectra.

Thermogravimetric analysis (TGA). The particle solution were first frozen in liquid nitrogen and then left under vacuum at −200° C. over three nights to dry. The powder after freeze-drying was further left under vacuum at 600° C. overnight. The dried out particle sample was then subjected to TGA. The TGA was conducted using a TA Instruments Q500 thermogravimetric analyzer. During the measurement, the temperature was increased from room temperature to 1000° C. with a ramp of 100° C./min and then remains at 1000° C. for 2 h to fully exclude any residual water. Afterward, the temperature was further increased to 6000° C. with a ramp of 100° C./min removing any organic moieties and leaving pure inorganic silica or aluminosilicate behind. The average amount of PEG chains on a particle was then estimated according to these TGA results.

Molecular model of c(RGDyC) functionalized C' dot. Based on the full analysis of the C' dot structure, e.g., core size, shell thickness, PEG surface density, number of surface ligands, and number of fluorophores encapsulated, a schematic molecular model was generated displaying the architecture of a C' dot at the atomic level with realistic scale. In order to do this, a 4 nm $SiO_2$ sphere was constructed, which is a continuous random network of Si and 0 atoms. The coordinates of each Si and 0 atoms inside the network were generated by reverse Monte Carlo simulation of a silica glass. A total of about 800 $SiO_2$ units present inside the core particle were used, which agrees with a calculation using the density of amorphous silica. Following this, a volume inside this core particle was manually created where one encapsulated Cy5 fluorophore is drawn. Afterwards, around 100 PEG chains and 16 c(RGDyC)-functionalized PEG chains covalently bonded to the silica particle surface were added manually. The final drawing represents one C' dot particle with a ~3 nm core, ~0.5 nm shell, one encapsulated Cy5 fluorophore, around 100 PEG chains, and 16 c(RGDyC) ligands on surface. It is important to note that the model is not the result of a true simulation, but is rather a scaled schematic drawing that provides a realistic visualization of the relative size scale of the different building blocks of one C' dot particle.

Example 2

This example describes a method and nanoparticle of the present disclosure

In contrast to small molar mass compounds the detailed structural investigation of nanoparticles remains challenging. In particular, the assessment of batch reaction induced heterogeneities of surface chemical properties and their correlation with particle size has been a long-standing issue. Applying a combination of high performance liquid chromatography (HPLC) and gel permeation chromatography (GPC) on ultrasmall 10 nm) poly(ethylene glycol) coated (PEGylated) fluorescent core-shell silica nanoparticles, here we elucidate previously unknown surface heterogeneities resulting from varying dye conjugation to nanoparticle silica cores and surfaces. These heterogeneities are predominantly governed by dye charge as corroborated by molecular dynamics simulations. Since surface chemical properties are key to all nanoparticle interactions, it is expected these fundamental insights are relevant to a number of applications including bioimaging and nanomedicine.

The study of ultrasmall (<10 nm) nanoparticles is an area of growing academic and technological interest as a result of size dependent properties and applications ranging from catalysis to nanomedicine. While in the past decade the library of ultrasmall nanoparticles has expanded substantially, detailed characterization in particular of heterogeneities in their surface-chemical composition and size has remained challenging. Biological nanomaterials such as proteins, antibodies, and their fragments have the benefit of consistent molar mass, and can be routinely analyzed by techniques such as high performance liquid chromatography (HPLC) and liquid chromatography coupled mass spectrometry (LC-MS). In contrast, synthetically produced single-batch ultrasmall nanoparticles that may be composed of inorganic and organic components typically display a distribution of sizes and masses, including a distribution of surface chemistries present. The size and surface chemistry of nanoparticles has already been shown to be of paramount importance for the therapeutic and diagnostic application of nanomaterials. In the past researchers have relied heavily on electron microscopy for characterization, but these techniques reveal little information about the surface ligand chemistry of ultrasmall nanoparticles.

In order to characterize nanoparticle synthesis batch heterogeneity in surface chemistry and its correlation to particle size, described is a combination of HPLC and gel permeation chromatography (GPC). While using HPLC for the characterization of organic compounds and macromolecules is ubiquitous, its application to organic-inorganic hybrid nanoparticles is scarce. Described is the sensitivity of HPLC to small changes in chemistry applied to ultrasmall (<10 nm diameter) inorganic nanoparticles stabilized with organic ligands provides hitherto unknown insights into surface-chemical heterogeneity. In combination with other techniques, including fluorescence correlation spectroscopy (FCS), single molecule bleaching experiments, and molecular dynamics simulations, the molecular origin of these heterogeneities are elucidated and correlated to particle size via coupled GPC-HPLC runs. We expect that our approach will enable synthesis of better defined materials for applications e.g. in bioimaging and nanomedicine.

Ultrasmall (<10 nm) poly(ethylene glycol) coated (PEGylated) fluorescent core shell silica nanoparticles known as Cornell dots or simply C dots were studied. In particular, fluorescent Cy5 dye encapsulating particles synthesized in water referred to PEG-Cy5-C' dots and cyclic targeting peptide, c(RGDyC), functionalized c(RGDyC)-PEG-Cy5-C' dots were focused on. First human clinical trial results with such targeted nanoparticles demonstrated their safety, and multiple trials, including a phase 2 trial in melanoma. After synthesis, the PEG-Cy5-C' dot and c(RGDyC)-PEG-Cy5-C' dot batches were subjected to purification by GPC removing impurities including particle aggregates, free dye, and free PEG/c(RGDyC)-PEG that differ in size from the desired product and resulting in a single peak as shown for PEG-Cy5-C' dots in FIG. 1A. Purified C' dots were subsequently characterized using an HPLC method carefully tuned to separate the nanoparticles based on small differences in surface chemical properties (see Materials and Methods). A representative HPLC chromatogram for PEG-Cy5-C' dots as detected at the 647 nm Cy5 absorbance wavelength (FIG. 1B, blue line) revealed four distinct peaks, three dominant peaks at earlier times (<34 min) and a small peak at later time (~35 min). Using a 275 nm detector, a wavelength more sensitive to PEG, another main absorbing component of the particles, the chromatogram reproduced the three dominant peaks, albeit with different peak intensities (FIG. 1B, red line). The corresponding HPLC chromatogram for the c(RGDyC)-PEG-Cy5-C' dots (FIG. 1C) was less well resolved due to peak broadening, but the main features of the PEG-Cy5-C' dot chromatogram were still present, indicated the main source of heterogeneity was not the targeting peptides, but associated with the PEG-Cy5-C' dots synthesis.

In order to identify the origin of these heterogeneities, a range of cross experiments were performed. First, same size PEG-C' dots were synthesized, but without containing Cy5 dye. Applying the same HPLC method with 275 nm detection revealed only a single peak at the position of the first peak observed for PEG-Cy5-C' dots (FIG. 1B, black line). This suggested that the source of the heterogeneities is associated with the chemistry of Cy5 dye encapsulation. It also revealed that the first peak for the PEG-Cy5-C' dots can be assigned to a particle fraction that has the same surface characteristics as the PEG-C' dots, i.e., a purely PEGylated surface. These particles may or may not contain a dye. If they do, it must be fully encapsulated within the silica core (see illustration in FIG. 1B inset).

Biotin-functionalized PEG-Cy5-C' dots were immobilized on a glass slide previously functionalized with streptavidin (FIG. 1D) and exposed the particles to the evanescence field of a fluorescence microscope in total internal reflection geometry at low laser power and in the presence of an oxygen scavenger system. Continuous exposure of the immobilized particles caused Cy5 dye photobleaching. An image stack was recorded until 99% of the original fluorescence signal was muted (FIG. 1E). Representative fluorescence time traces of biotinylated PEG-Cy5-C' dots were extracted from the images and are shown in FIG. 1F. When a dye bleaches a sharp step in the intensity trace is observed as indicated by arrows. The traces show nanoparticles with one, two, three, and four steps, respectively, before the intensity reaches the background, suggesting one to four dyes per particle. About 650 immobilized particles of a single particle synthesis batch were analyzed to generate the statistics shown in FIG. 1G, indicating that ~55% of the PEG-Cy5-C' dots had one dye, with increasingly smaller numbers of particles carrying two, three, or four dye molecules per particle, respectively. These results together with the HPLC results indicated the four HPLC peaks are associated with zero, one, two, or three Cy5 dyes, respectively, at the silica core surface.

Cyanine dyes like Cy5 are known to undergo photo-induced cis-trans isomerization around the characteristic polymethine bridge between a fluorescent trans-state and a non-(or weakly) fluorescent cis-state. The rates of photo-isomerization and back-isomerization are sensitive to the steric environment and have been used to probe membrane microviscocity of cells using FCS. The more steric hindrance there is, the more retarded the isomerization becomes. The conformational change of cyanine dyes can be observed in FCS at short lag times ($<10^{-5}$ s) by a change of the amplitude in the correlation curve, as well as a change of associated characteristic relaxation time. The HPLC elution volume was fractionated (shaded areas in FIG. 1B) and performed FCS measurements on fractions associated with each of the three dominant peaks 1-3. FIG. 1H(i) compares FCS correlation curves for the three particle fractions, unfractioned particles, and free Cy5 dye. Curves for all particles are shifted to longer times relative to free dye, as their larger size leads to slower diffusion through the focal volume illuminated in FCS. The bottom curves (ii) show the isolated contributions of cis-trans photo-isomerization to the respective FCS curves in (i). Quantitative FCS analyses revealed that all particles tested had the same size (inset of FIG. 1H and FIG. 1I) confirming that HPLC is separating peaks predominantly as a function of particle surface chemistry. Separated fractions showed increasing numbers of dyes per particle as elution time increased (FIG. 1K), corroborating that additional dye covalently attached to the particle surface is the source of the heterogeneity. FIG. 1J illustrates that the brightness per dye decreases with increasing peak elution time. A decrease of dye brightness in particles with more dyes per particle is consistent with energy transfer between dyes or near surface dye locations. Cy5 has a hydrodynamic diameter of roughly 1.3 nm (FIG. 1I), so it stands to reason that two or more dyes would not fully reside inside a silica particle core of only 2.5 nm hydrodynamic radius. Dyes on the particle surface are less confined than dyes fully encapsulated within the rigid silica matrix and may be prone to additional forms of non-radiative energy dissipation pathways. One of the most significant non-radiative decay rates for Cy5 was quantified by analyzing the photo-isomerization of particles in each of the HPLC fractions as compared to unfractionated PEG-Cy5-C' dots. As peak elution time increases, the percentage of dye undergoing photo-isomerization increases (FIG. 1L), suggesting that particles with larger dye numbers are likely to have more Cy5 molecules on the particle surface, where it can more freely undergo photo-isomerization. For the PEG-Cy5-C' dots, this points to later eluting peaks corresponding to more dyes being located on or near the silica core surface, consistent with our hypothesis. The sensitivity of the HPLC method is high enough so that the difference of one dye on the silica core surface will have significant effects on elution time. It was estimated that the percentage of particles with zero, one, two, or three dyes on the surface from HPLC peak area integrations (Table T5). Differences to results from the dye photobleaching statistics (FIG. 1G) can be rationalized by the fact that HPLC does not separate based on the absolute number of dyes per particle, which includes particles that have dyes on the surface and fully encapsulated in the core.

Figure 2:
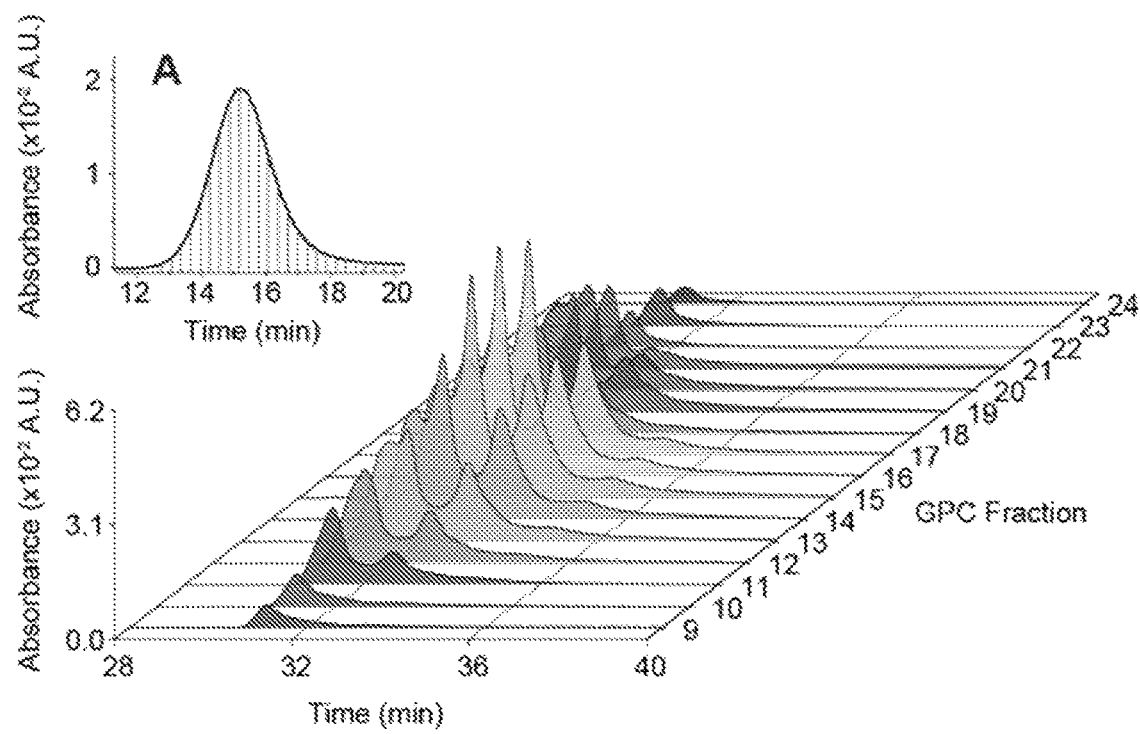
FIG. 2 shows coupled GPC-HPLC nanoparticle characterization. (A) Waterfall plot of coupled GPC-HPLC runs for PEG-Cy5-C' dots. The inset shows the GPC trace of the PEG-Cy5-C' dots used in this experiment; red lines are the fraction collection starting points. (B) Waterfall plot of coupled GPC-HPLC runs for PEG-Cy5-C' dots showing the subset of the GPC fractions collected in (A) that were concentrated to a uniform concentration and reanalyzed. The inset shows particle concentrations as determined by a combination of UV/Vis absorbance and FCS measurements. (C) Waterfall plot showing the coupled GPC-HPLC analysis of MB2 C' dots (PEG-MB2-C' dots). From the inset, the concentration of these particles is less uniform as compared to (B) in part because methylene blue is a non-fluorescent dye and FCS particle analysis could not be performed. (D, E) Overlay of three representative chromatograms from concentration normalized coupled GPC-HPLC runs in (B) and (C). Large, mid-sized, and small particles show only minor differences in surface chemistry heterogeneity.
Figure 2:
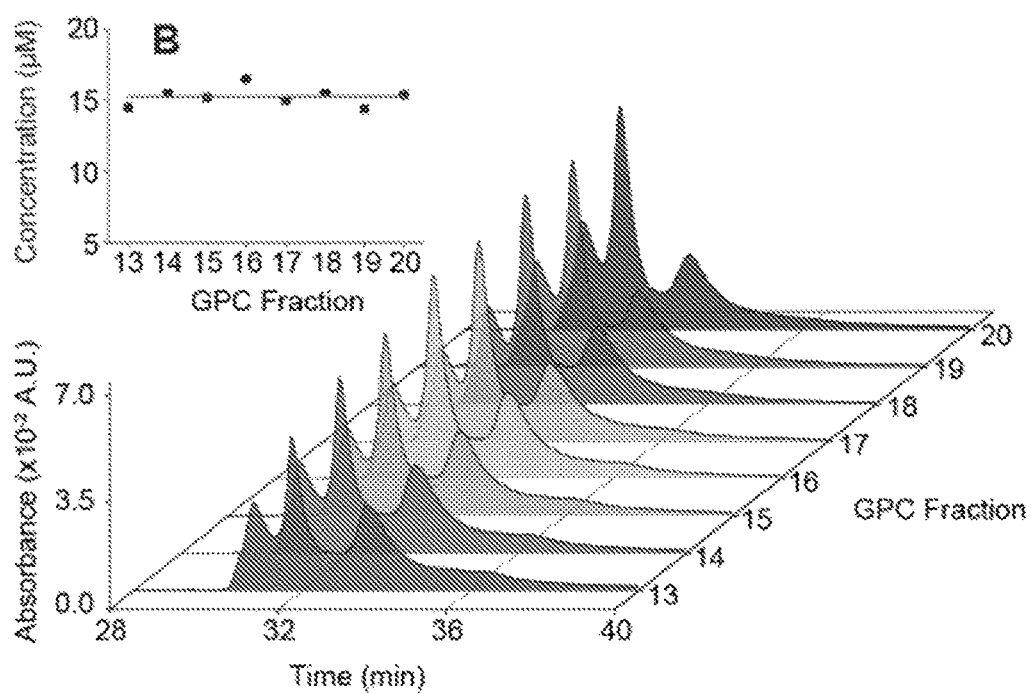
Figure 2:
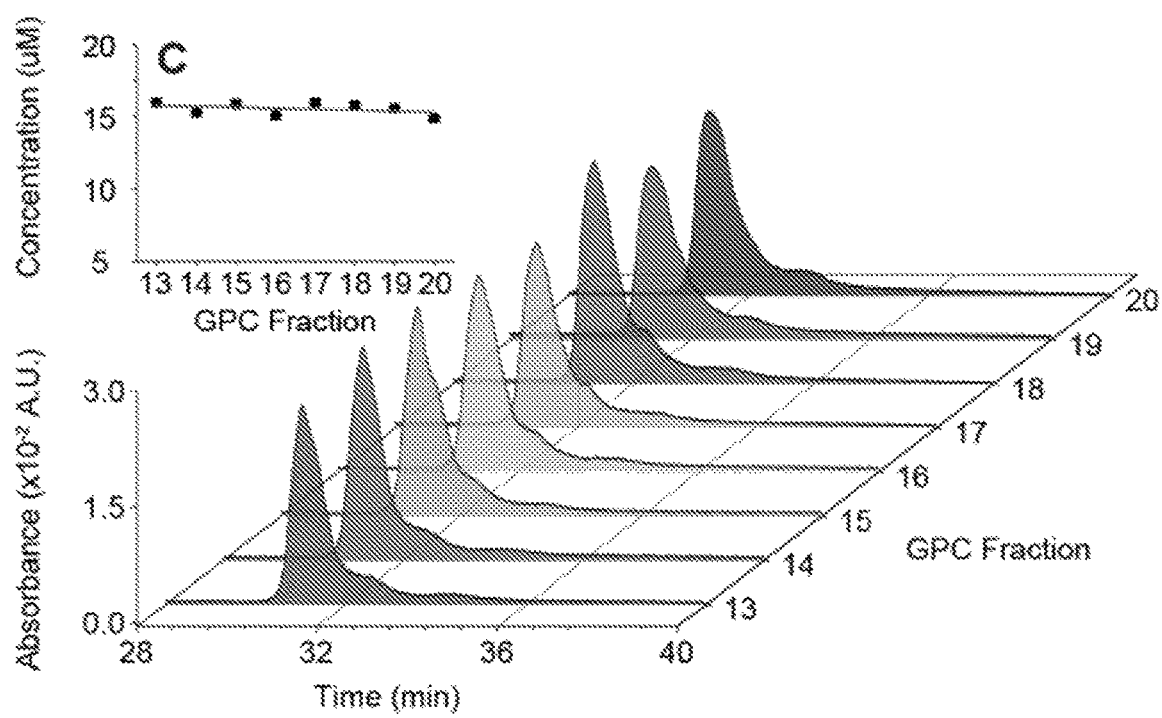
Figure 2:
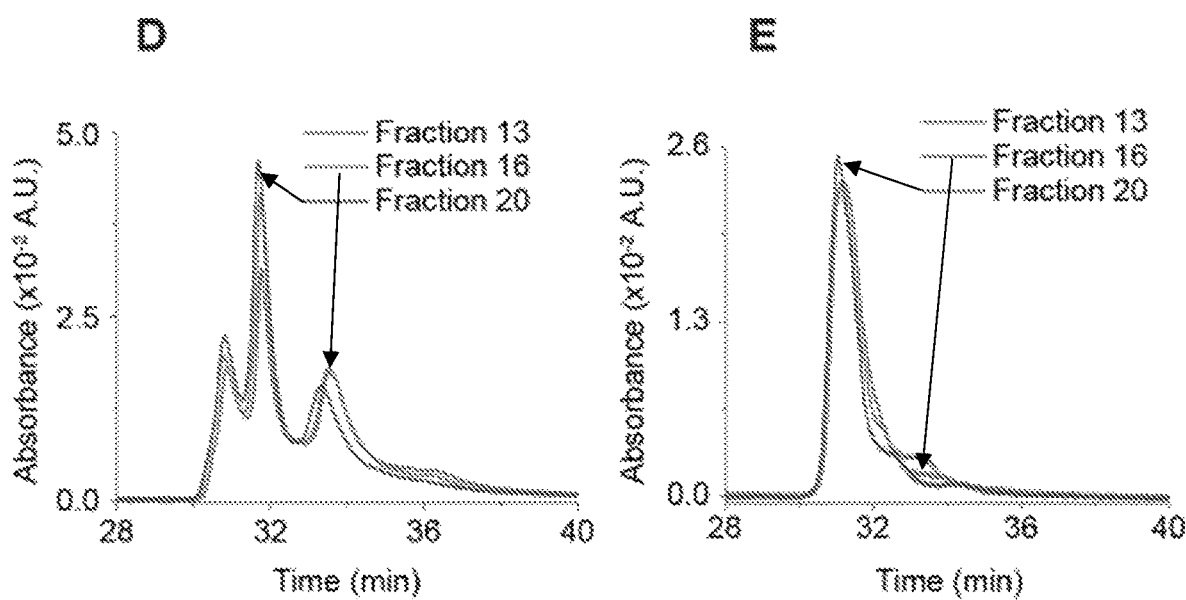
Figure 3:
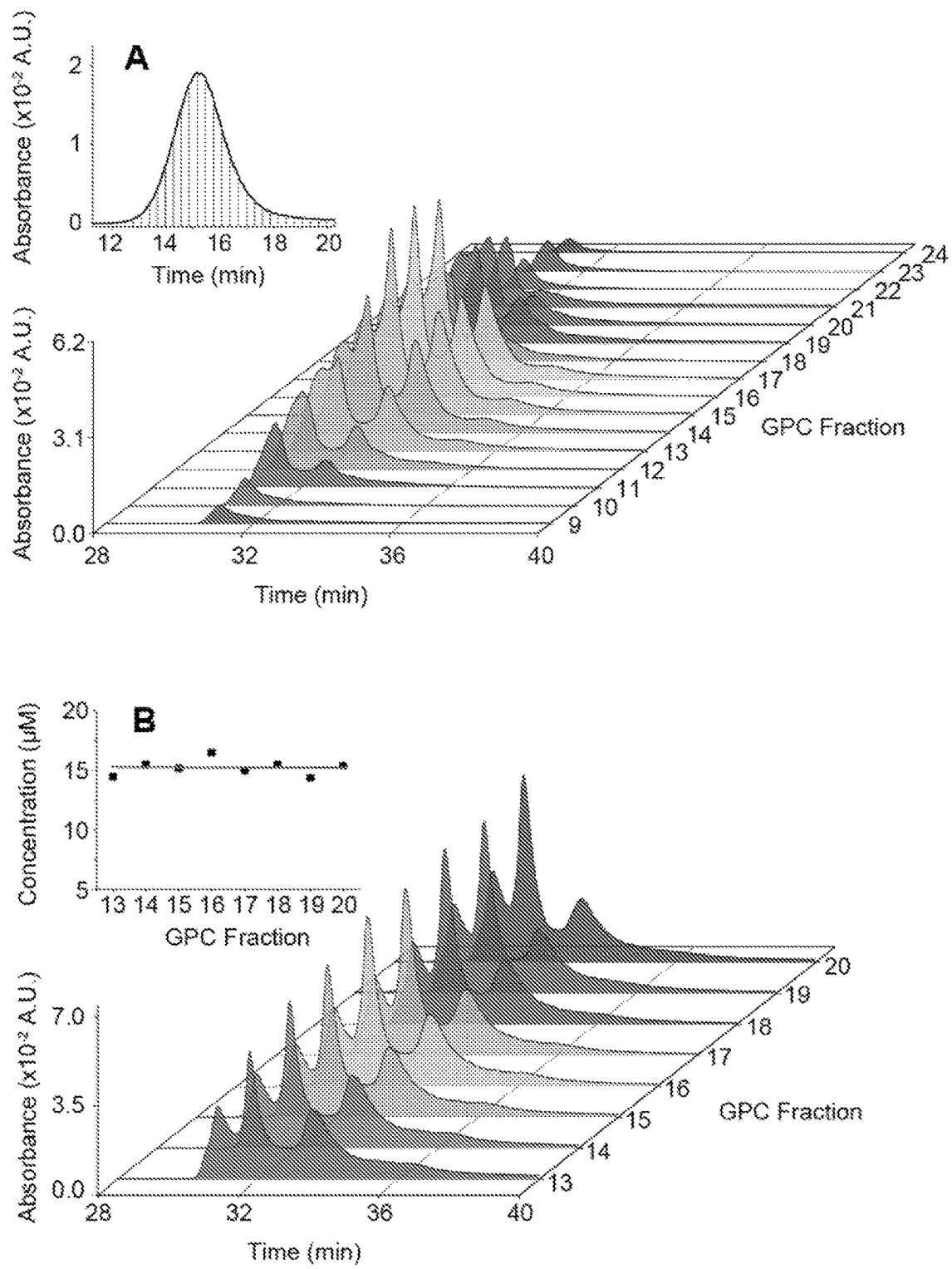
FIG. 3 shows coupled GPC-HPLC nanoparticle characterization. (A) Waterfall plot of coupled GPC-HPLC runs for PEG-Cy5-C' dots. Inset shows GPC trace of PEG-Cy5-C' dots; lines are the fraction collection starting points. (B) Waterfall plot of coupled GPC-HPLC runs for PEG-Cy5-C' dots from subset of GPC fractions collected in (A) and concentrated to a uniform concentration (inset) as determined by a combination of UV/Vis absorbance and FCS. (C) Same as in (B) for MB2 C' dots (PEG-MB2-C' dots), but with less uniform particle concentration, in part because methylene blue is a non-fluorescent dye, and FCS could not be performed. (D) Same as (B) and (C) but for PEG-Cy5 (+)-C' dots, a particle synthesized using the same dye as in PEG-Cy5-C' dots, but with a net positive charge as opposed to a net negative charge. (E, F, G) Overlay of three representative chromatograms from concentration normalized coupled GPC-HPLC runs in (B), (C), and (D). Large, mid-sized, and small particles show minor (E, F) or no (G) differences in surface chemical heterogeneity, depending on particle type.
Figure 3:
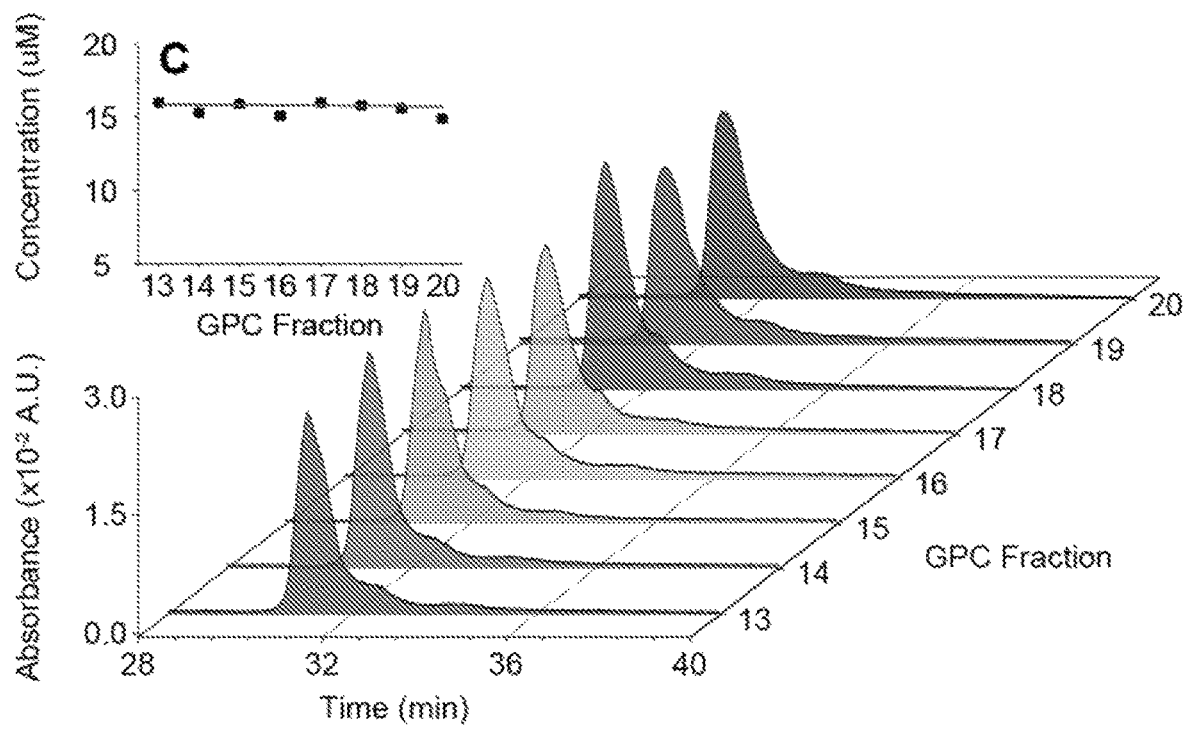
Figure 3:
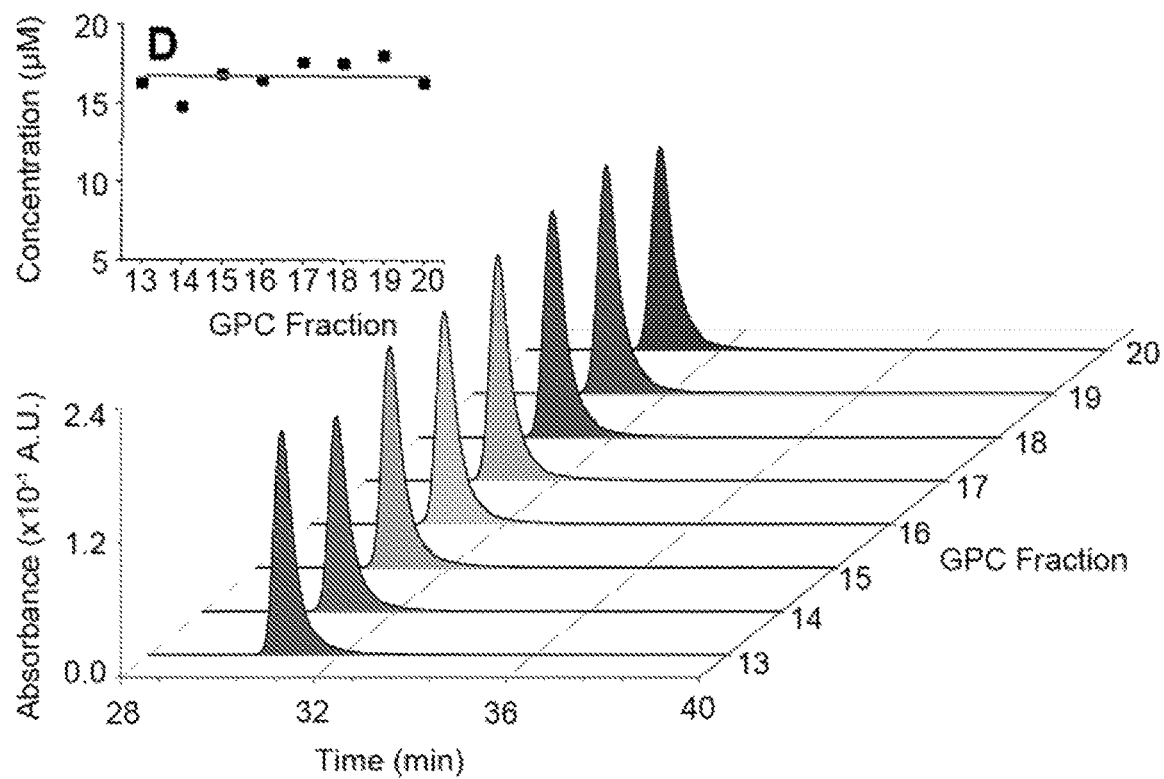
Figure 3:
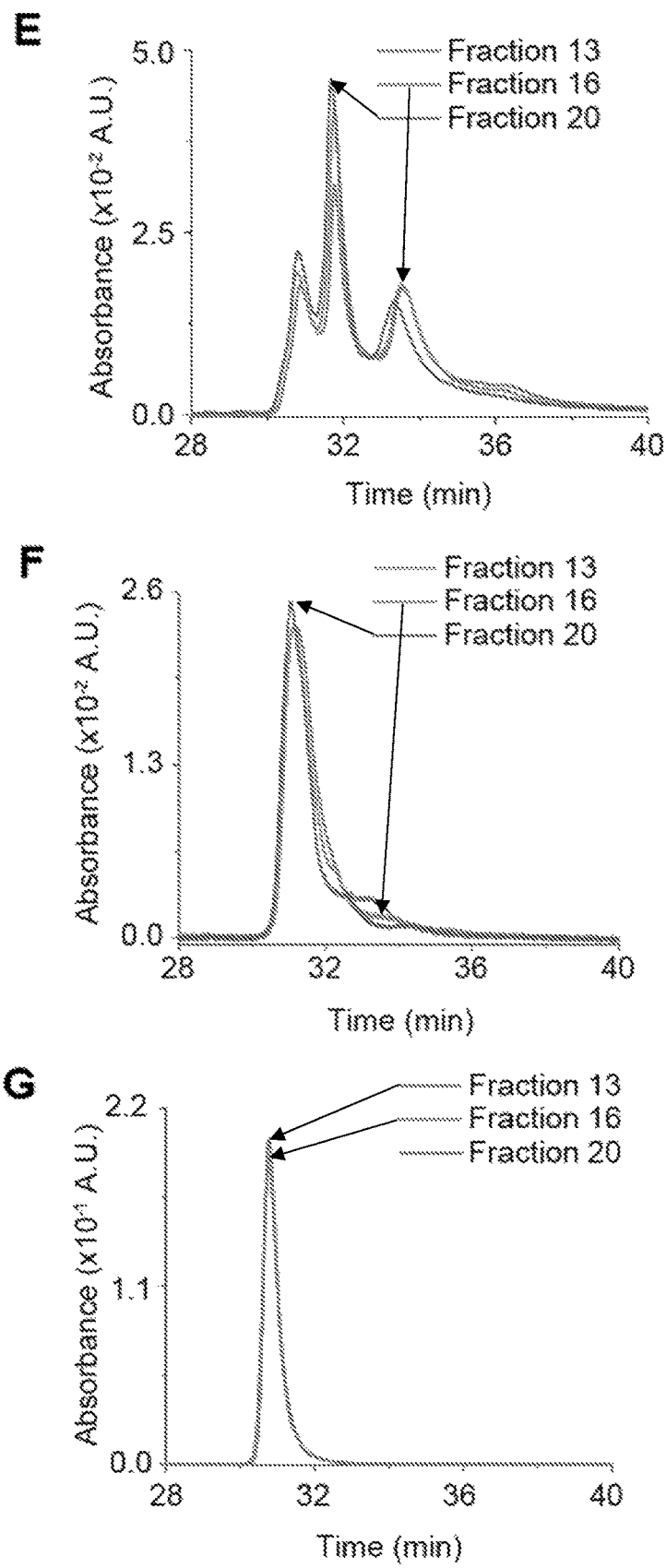

The high-resolution method enabled us to tackle hitherto unresolved questions about property variability across a particle synthesis batch. For example, it is highly desirable to elucidate variations in surface chemical properties as a function of particle size within a batch, as they are expected to have substantial impact, e.g., on biological properties of nanoparticles. In order to address this knowledge gap, coupled GPC-HPLC separations were performed. A sample of pre-purified PEG-Cy5-C' dots was split into 15 fractions using GPC, which were then up-concentrated linearly to retain their GPC concentration relationship (inset FIG. 2A). These samples were sequentially injected into the HPLC for analysis. Results were plotted in two-dimensional (2D waterfall) plots with HPLC resolution along the x axis, GPC resolution along the y axis, and absorbance along the z axis (FIG. 2). Concentration differences between tailing and central GPC fractions caused loss of full peak resolution for the tailing fractions (FIG. 2A). This could be circumvented by moving to a subset of eight GPC fractions with each fraction adjusted to the same final concentration and then run through the HPLC (FIG. 2B and inset). Results elucidate that within this subset there is no dependence of the surface chemical properties on particle size. Detailed comparison of fractions 13, 16, and 20 representing large, medium, and small particles of the distribution, respectively, reveal that there is a small increase in surface bound dyes with particle size as expected from their increased particle surface area (FIG. 2D). Results suggest that for these PEG-Cy5-C' dot batches fear of the "worst-case scenario" with surface chemical properties strongly correlated with size and thus maximum complexity in particle heterogeneity is unsubstantiated. FIG. 3 shows coupled GPC-HPLC nanoparticle characterization. (A) Waterfall plot of coupled GPC-HPLC runs for PEG-Cy5-C' dots. Inset shows GPC trace of PEG-Cy5-C' dots; lines are the fraction collection starting points. (B) Waterfall plot of coupled GPC-HPLC runs for PEG-Cy5-C' dots from subset of GPC fractions collected in (A) and concentrated to a uniform concentration (inset) as determined by a combination of UV/Vis absorbance and FCS. (C) Same as in (B) for MB2 C' dots (PEG-MB2-C' dots), but with less uniform particle concentration, in part because methylene blue is a non-fluorescent dye, and FCS could not be performed. (D) Same as (B) and (C) but for PEG-Cy5 (+)-C' dots, a particle synthesized using the same dye as in PEG-Cy5-C' dots, but with a net positive charge as opposed to a net negative charge. (E, F, G) Overlay of three representative chromatograms from concentration normalized coupled GPC-HPLC runs in (B), (C), and (D). Large, mid-sized, and small particles show minor (E, F) or no (G) differences in surface chemical heterogeneity, depending on particle type.

Figure 4:
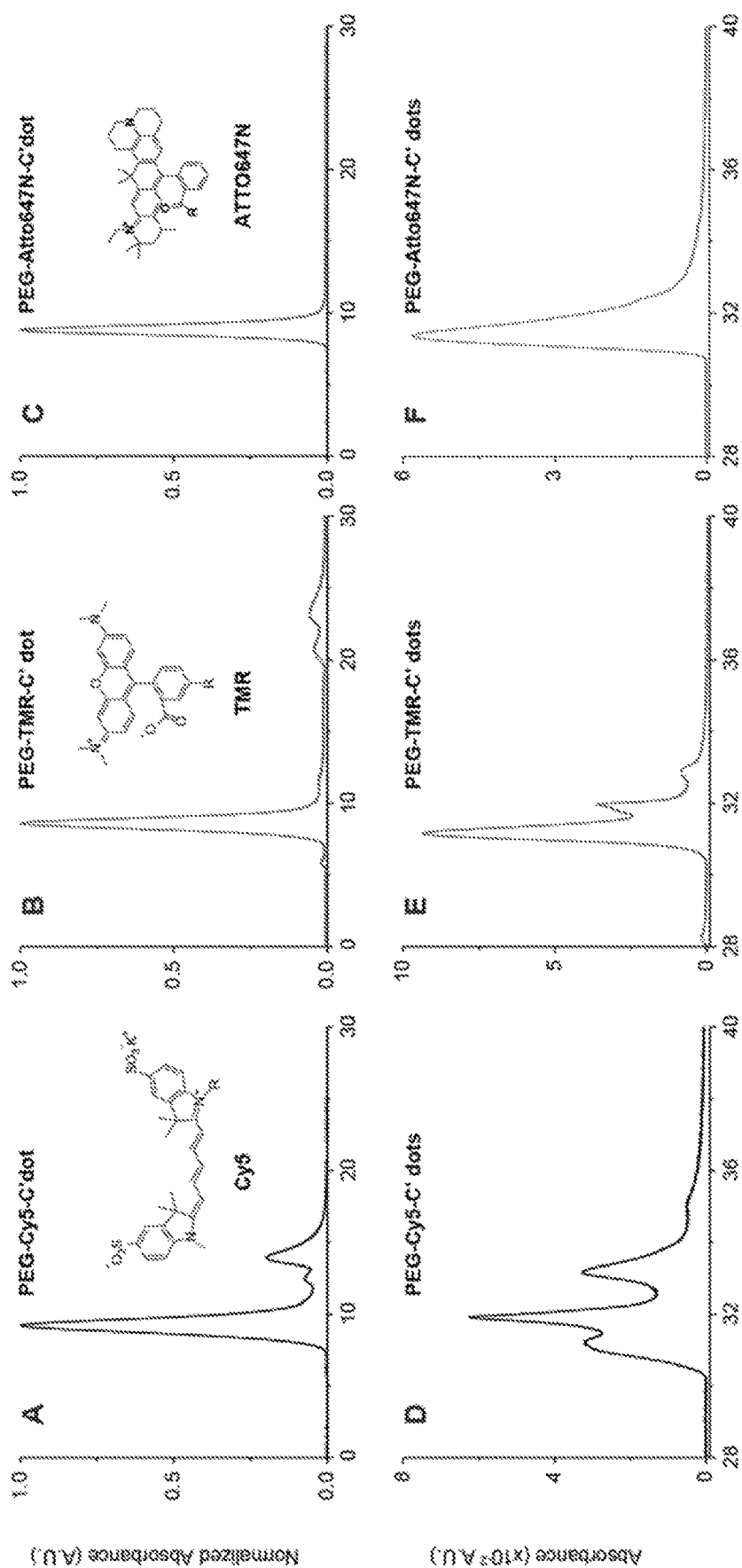
FIG. 4 shows dye incorporation efficiency and nanoparticle heterogeneity as a function of dye charge. (A-C) Analytical GPC chromatograms of native synthesis solutions prior to preparative scale purification: PEG-Cy5-C' dot solution (A) as detected at 647 nm with peaks corresponding to the particles, PEG-Cy5 conjugates, and free Cy5, in order of elution (for incorporation efficiency, see Table T3); PEG-TMR-C' dot solution (B) as detected at 553 nm with largest peak corresponding to PEG-TMR-C' dots (for incorporation efficiency see Table T2); PEG-ATTO647N-C' dot solution detected at 647 nm, (incorporation efficiency ~100%). (D-I) HPLC chromatograms of: PEG-Cy5-C' dots (D), PEG-TMR-C' dots (E), PEG-ATTO647N-C' dots (F), PEG-Cy3-C' dots (G), PEG-ATTO680-C' dots (H), and PEG-MB2-C' dots (I). Dye structures are shown in insets.
Figure 4:
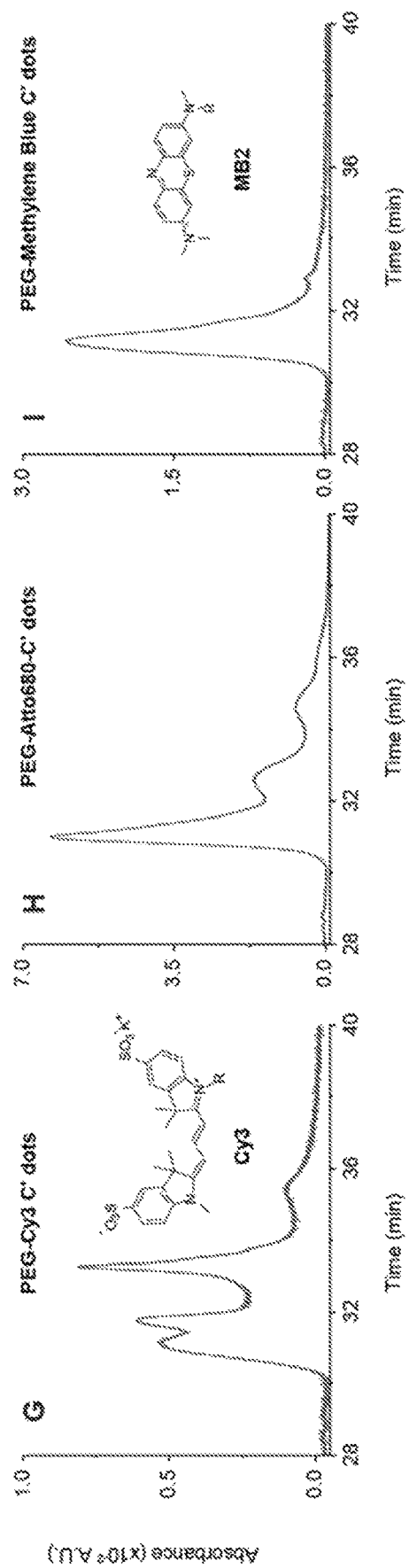
Figure 6:
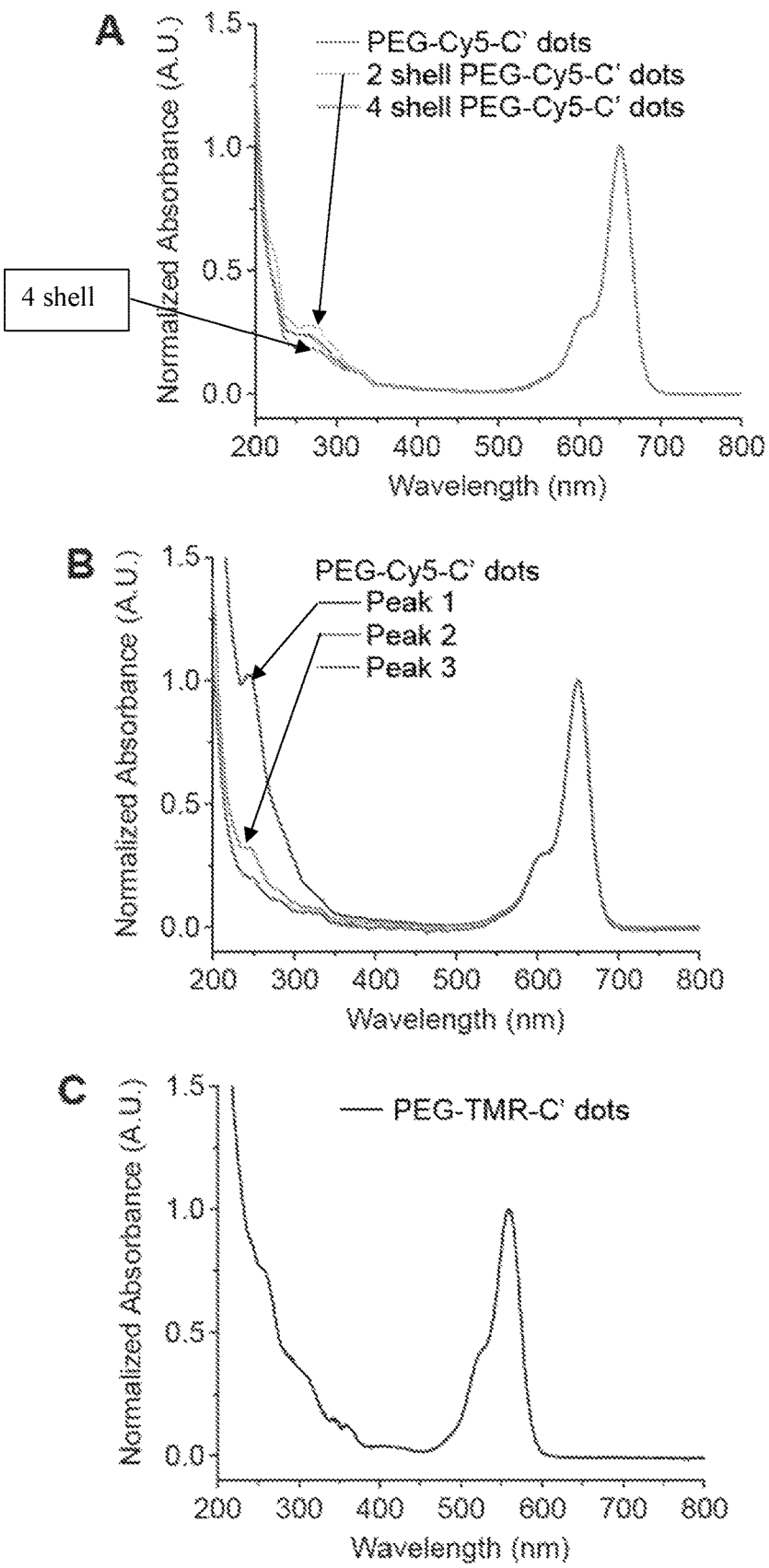
FIG. 6 shows (A) UV/Vis spectra of PEG-Cy5-C' dots. (B) UV/Vis spectra of Peak 1, Peak 2, Peak 3, collected from HPLC fractionation. (C) & (D) UV/Vis spectrum and FCS correlation curve of PEG-TMR-C' dots. (E) & (F) UV/Vis spectrum and FCS correlation curve of PEG-ATTO647N-C' dots. (G) & (H) UV/Vis spectrum and FCS correlation curve of PEG-Cy3-C' dots. (I) & (J) UV/Vis spectrum and FCS correlation curve of PEG-ATTO680-C' dots. (K) & (L) UV/Vis spectrum and FCS correlation curve of PEG-TMR-MB2-C' dots.
Figure 6:
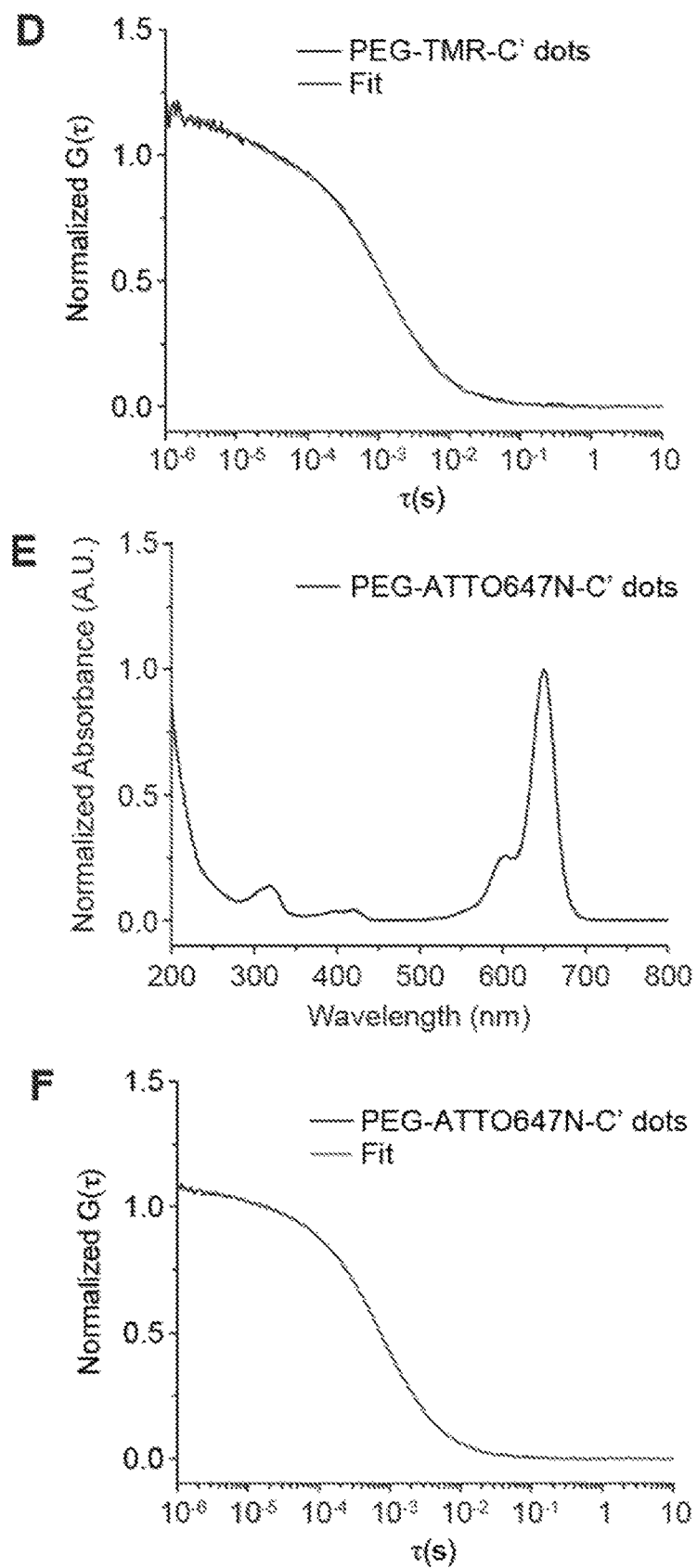
Figure 6:
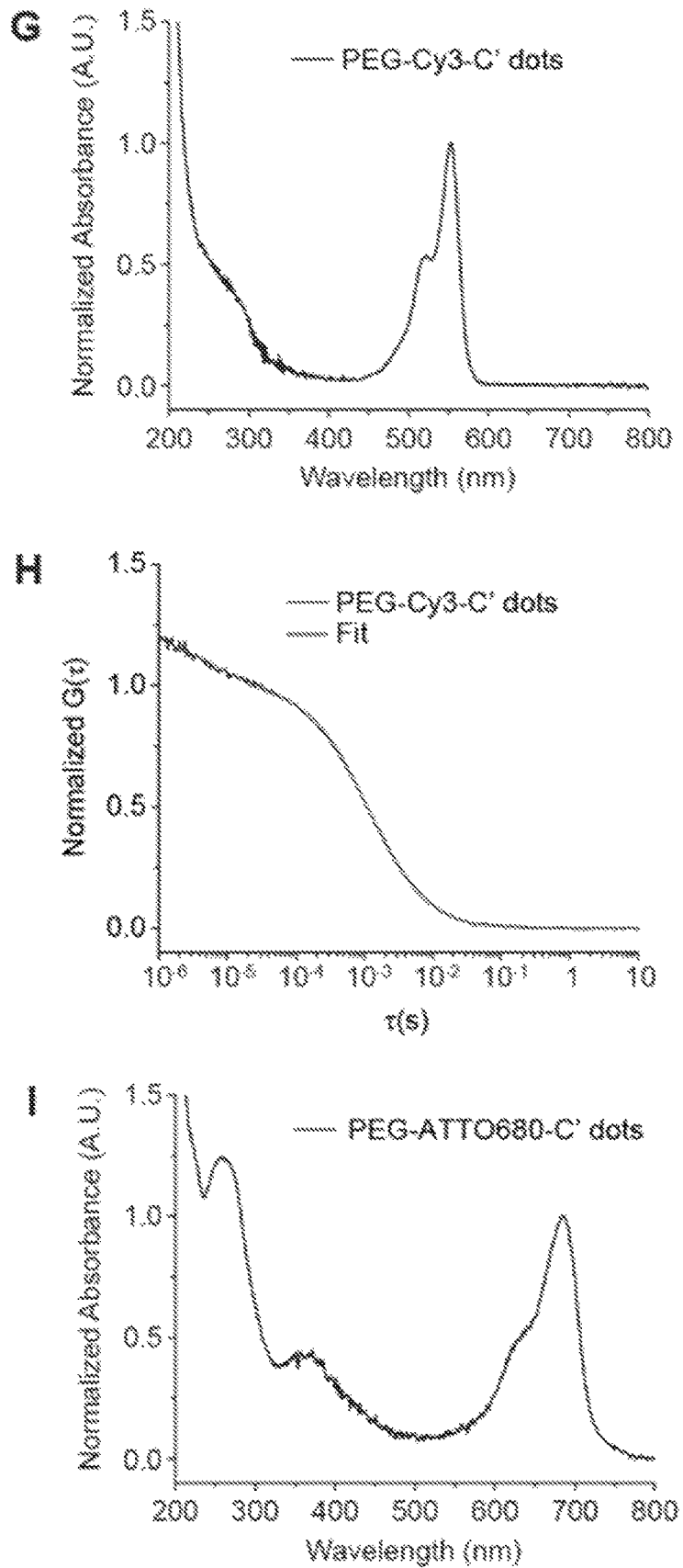
Figure 6:
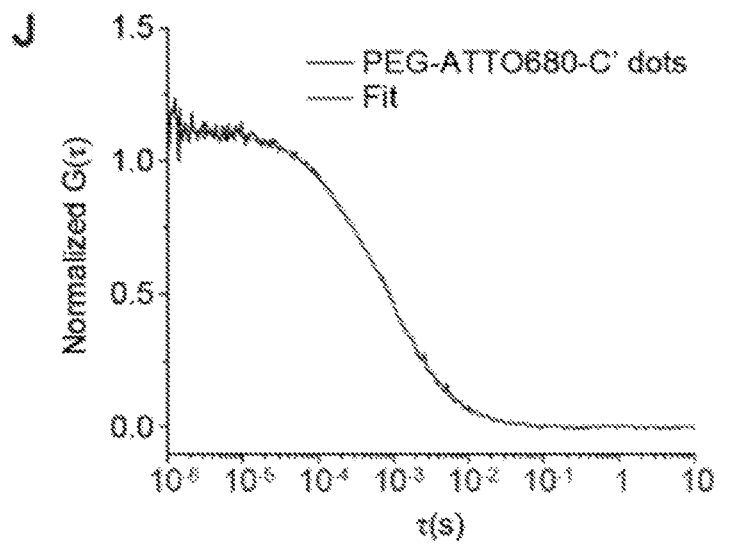
Figure 6:
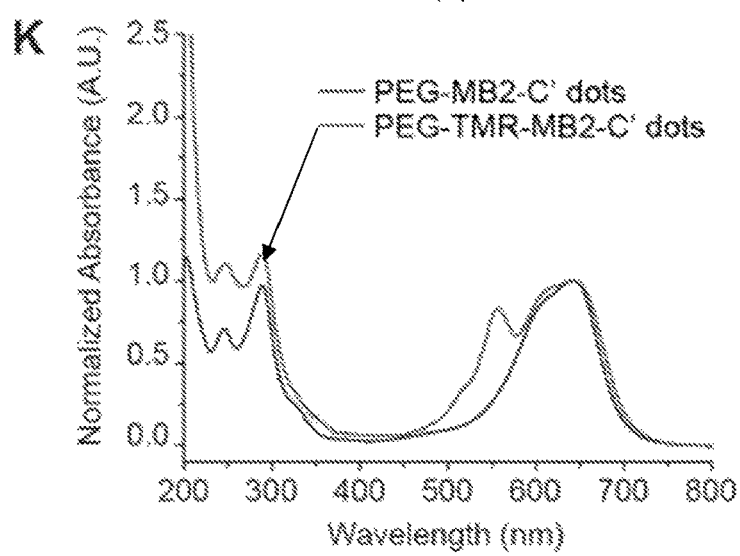
Figure 6:
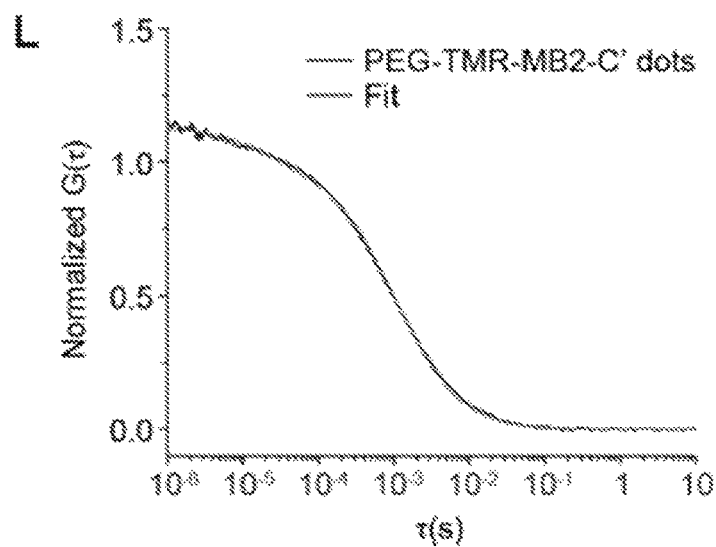
Figure 7:
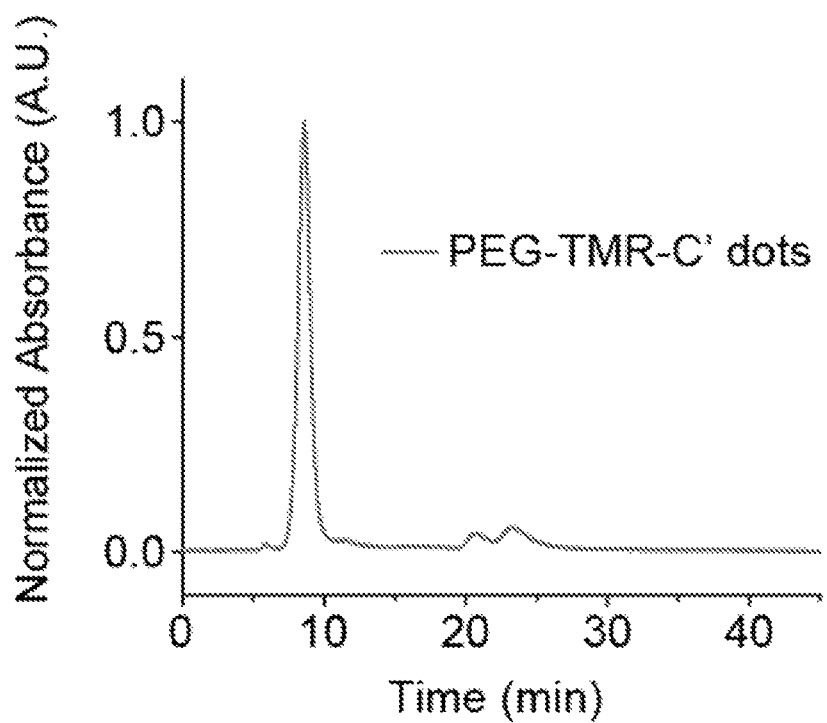
FIG. 7 shows GPC chromatogram of native synthesis solution of PEG-TMR-C' dots collected at 550 nm to measure dye incorporation.
Figure 8:
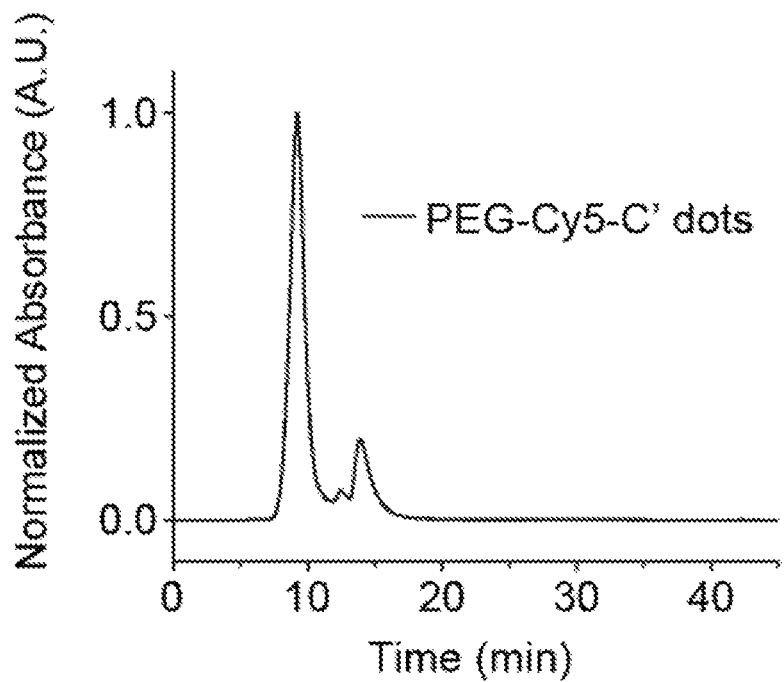
FIG. 8 shows GPC chromatogram of native synthesis solution of PEG-Cy5-C' dots collected at 647 nm to measure dye incorporation.
Figure 9:
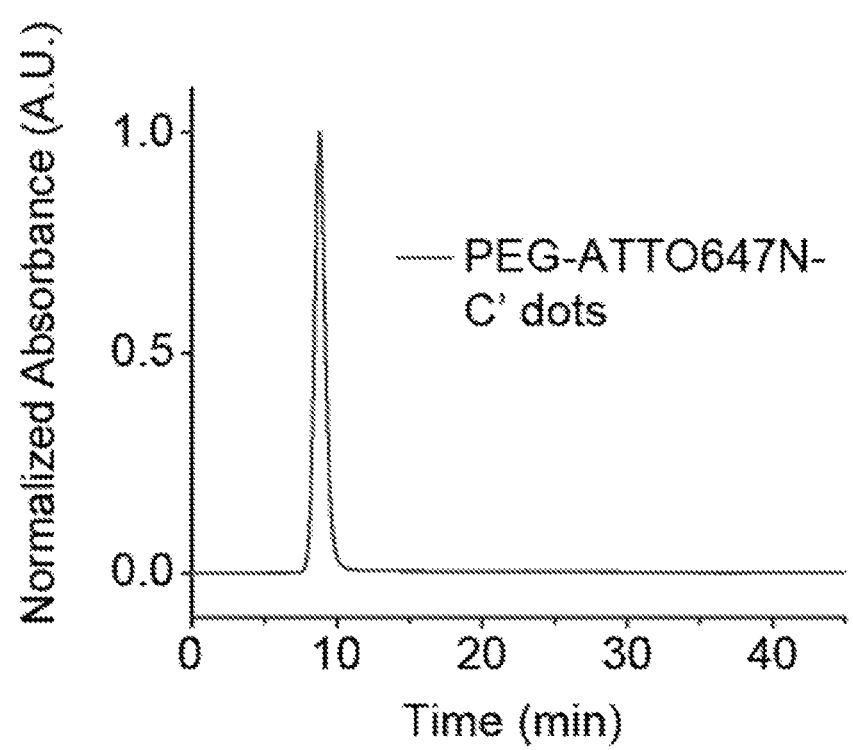
FIG. 9 shows GPC chromatogram of native synthesis solution of PEG-ATTO647N-C' dots collected at 647 nm to measure dye incorporation.
Figure 10:
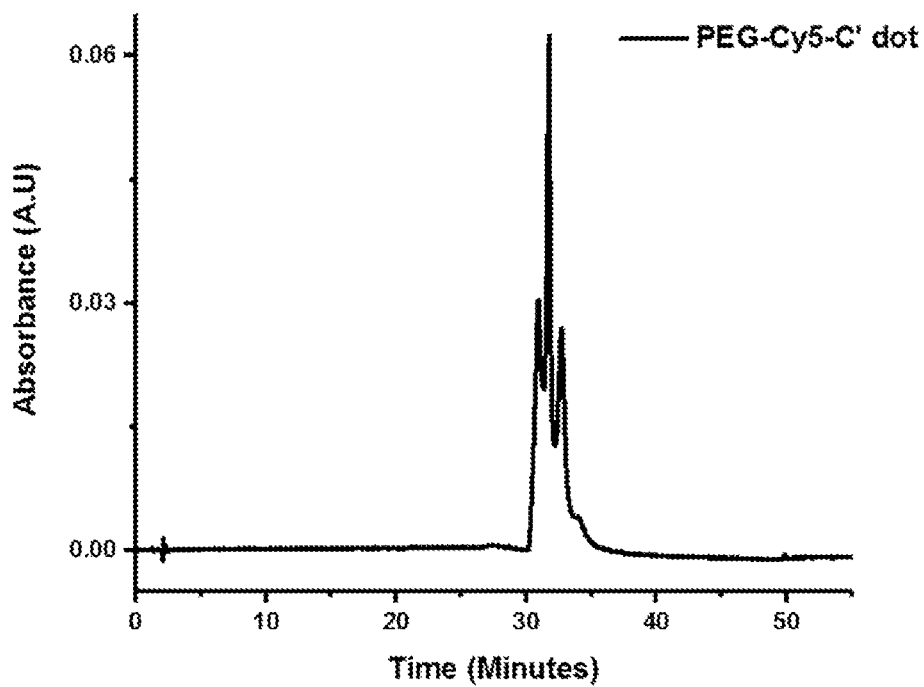
FIG. 10 shows A) representative chromatogram of PEG-Cy5-C' dots with no post processing done (i.e., baseline subtraction), B) the same chromatogram with baseline subtraction applied.
Figure 10:
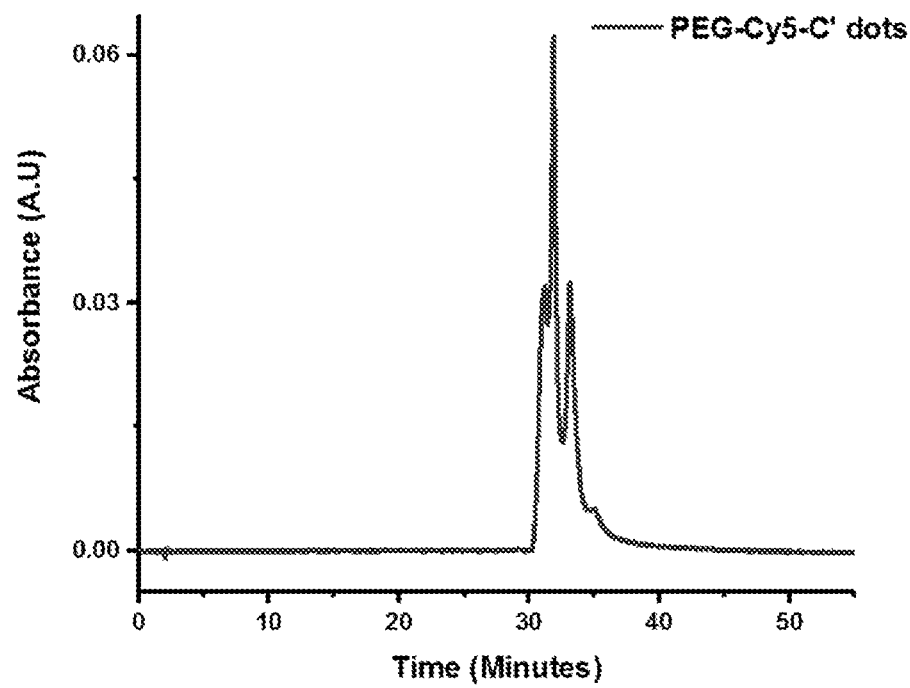

Heterogeneities in particle surface chemical properties are highly undesirable as they confound establishing exact particle structure-property correlations. This raised the question whether particle heterogeneity could be controlled. In further experiments, these heterogeneities were evaluated as a function of dye chemistry, in particular as a function of dye charge. In addition to working with negatively charged Cy5, synthesized PEG-C' dots were synthesized from zwitterionic TMR dye, as well as from positively charged ATTO647N dye (FIG. 4). GPC was used on native particle synthesis solutions to monitor dye incorporation efficiency and HPLC on purified samples to characterize surface chemical properties. The GPC and HPLC experiments revealed that dye incorporation efficiency and homogeneity of surface chemical properties substantially increased in the sequence Cy5<TMR<ATTO647N (FIG. 4A-F), with ATTO647N resulting in single peak chromatograms for both GPC and HPLC (FIGS. 4C and F). Incorporation efficiencies were near 100% for ATTO647N, 82% for TMR, and only 62% for Cy5 (FIGS. 7-9, Tables T2-T4). This suggested that net dye charge plays a crucial role in both, efficient dye encapsulation in silica and resulting heterogeneity in surface chemical properties. Results can be rationalized by considering Coulomb interactions between dye and silica particles during growth: the basic synthesis conditions silica nanoparticles are far above their isoelectric point (pH-2-3) and are stabilized by negative surface charges before surface PEGylation. Interactions therefore switch from repulsive to attractive when moving from Cy5 across TMR to ATTO647N, consistent with increasing dye incorporation efficiency as revealed by GPC, numbers of dyes per particle for the latter two as determined by FCS (Table T1 and FIG. 6), and improved homogeneity of surface chemical properties as documented by HPLC.

It was confirmed that these trends were primarily dependent on dye charge and not on specific dye chemical characteristics by repeating this series of experiments substituting Cy5, TMR, and ATTO647N with same net charge series Cy3, ATTO680 (chemical structure proprietary), and non-fluorescent absorber dye MB2, respectively. FIG. 4G to I shows the respective HPLC chromatograms. Despite slight differences, e.g., in HPLC retention time between PEG-ATTO647N-C' dots and PEG-MB2-C' dots (compare FIGS. 4F and I) or in peak width between PEG-TMR-C' dots and PEG-ATTO680-C' dots (compare FIGS. 4E and H), this series matches the overall peak structure of the earlier series remarkably well with negatively charged Cy3 dye (like Cy5 dye) producing 4 peaks and positively charged MB2 dye (like ATTO647N dye) resulting in essentially a single relatively sharp peak.

Figure 5:
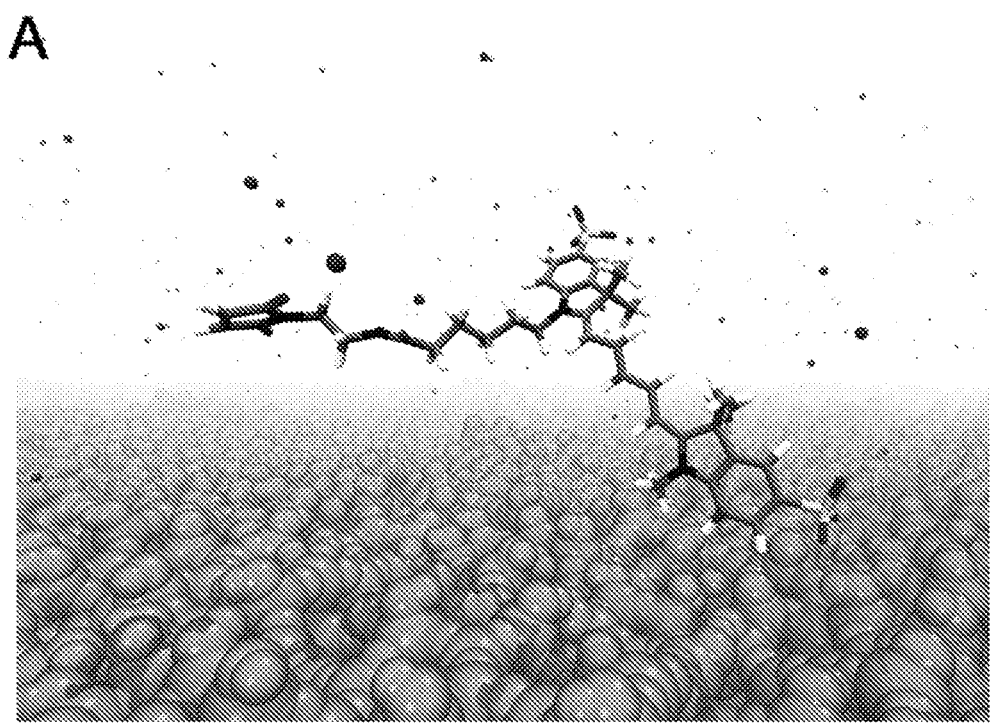
FIG. 5 shows molecular dynamics (MD) simulations and analysis. (A) Representative system of silica surface-dye MD simulations as-constructed, composed of water (not shown for clarity), amorphous $SiO_2$, Cy5 maleimide, and ammonium ions. In other systems Cy5 maleimide is replaced with the dye of interest, with or without attached silane unit. (B) Total linear interaction energies calculated between a silica surfaces and the dye silane molecules. Reported values are the average of the last 20 ns of five 100 ns simulations with randomly-oriented initial dye coordinates (see Materials & Methods for more details).
Figure 5:
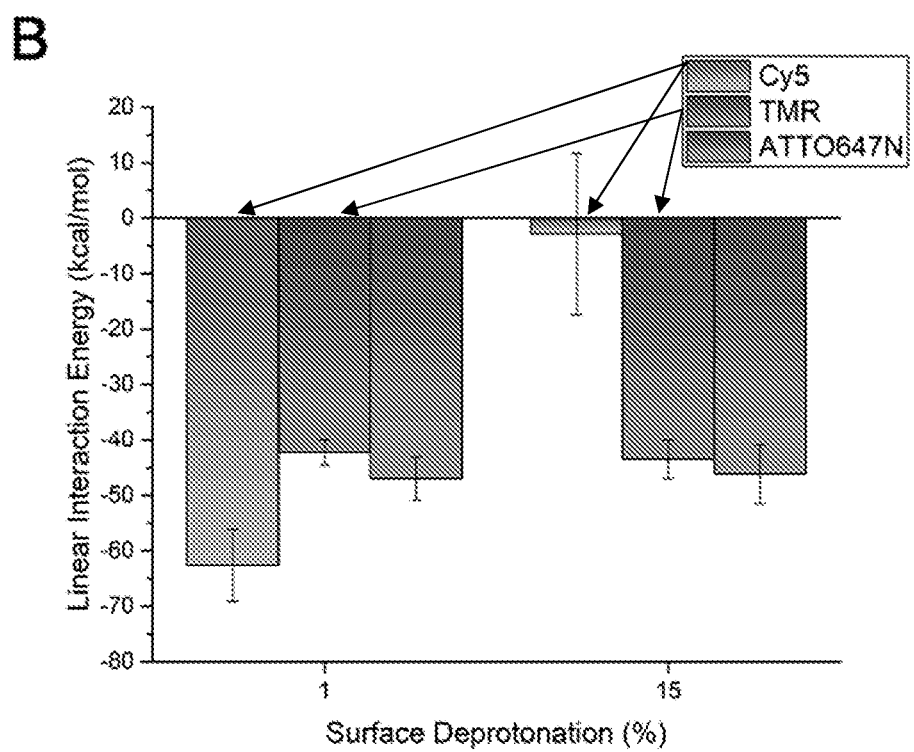
Figure 11:
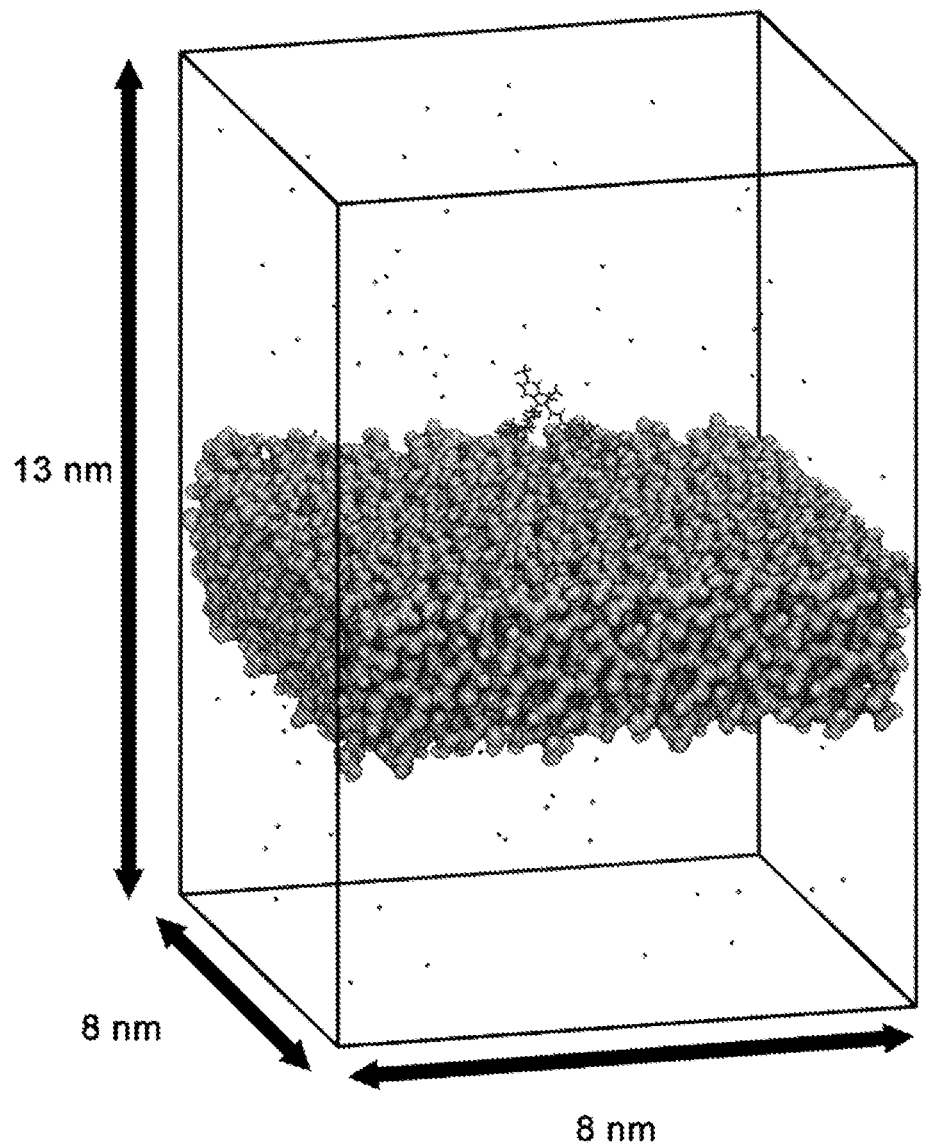
FIG. 11 shows Representative system of silica surface-dye MD simulations as-constructed, composed of water (not shown for clarity), amorphous $SiO_2$, Cy5 maleimide, and ammonium ions. In other systems Cy5 maleimide is replaced with the dye of interest, with or without attached silane unit.
Figure 12:
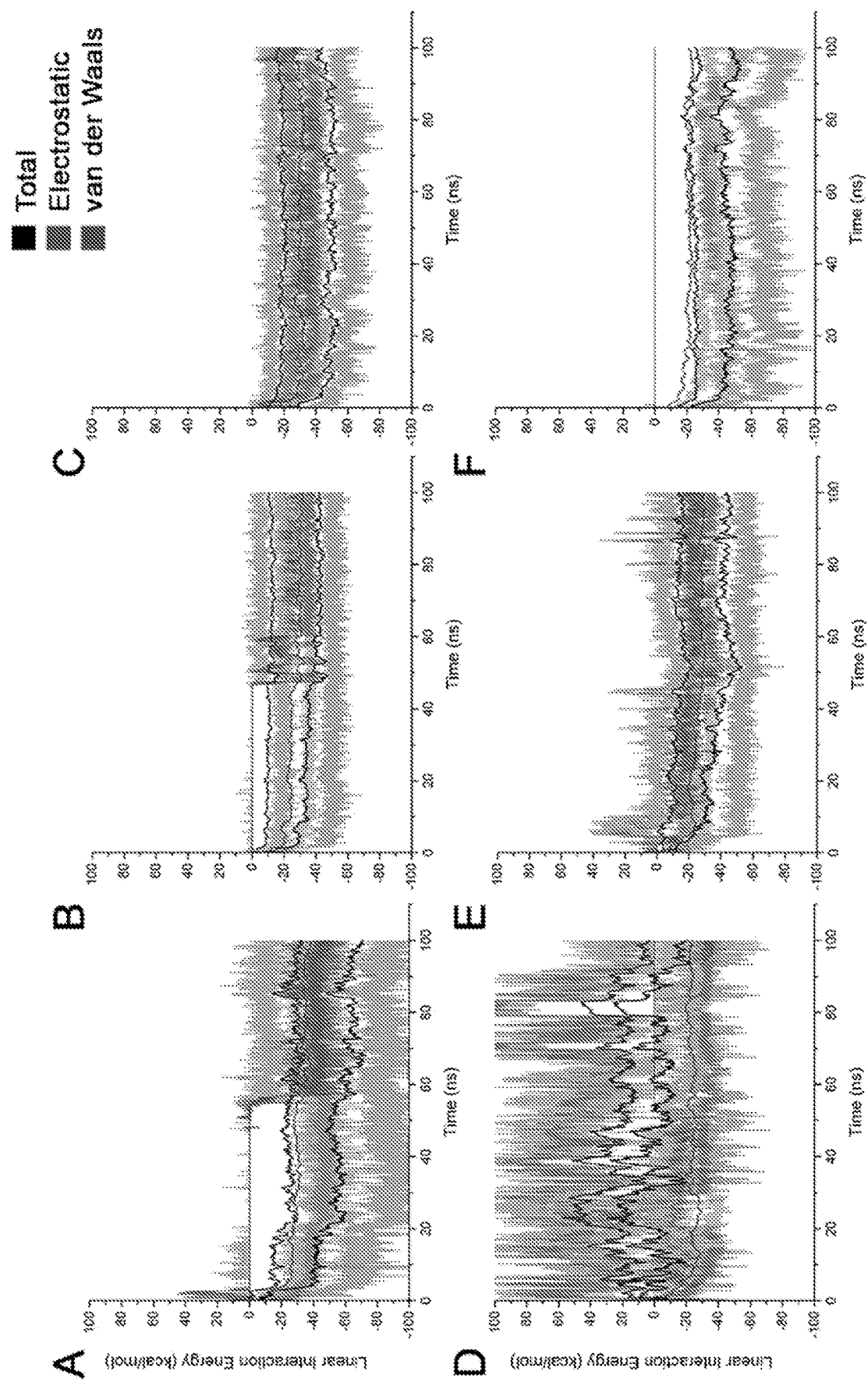
FIG. 12 shows (A-F): Linear interaction energy between silica surface and dye silanes over the entirety of the production simulations. Solid lines denote average of five simulations with random starting dye orientation, transparent lines indicate maximum and minimum of five simulations with random starting dye orientation. (a-c) 1% deprotonated silica surface, (d-f) 15% deprotonated silica surface. (a, d) Cy5, (b, e) TMR, and (c, f) ATTO647N.
Figure 13:
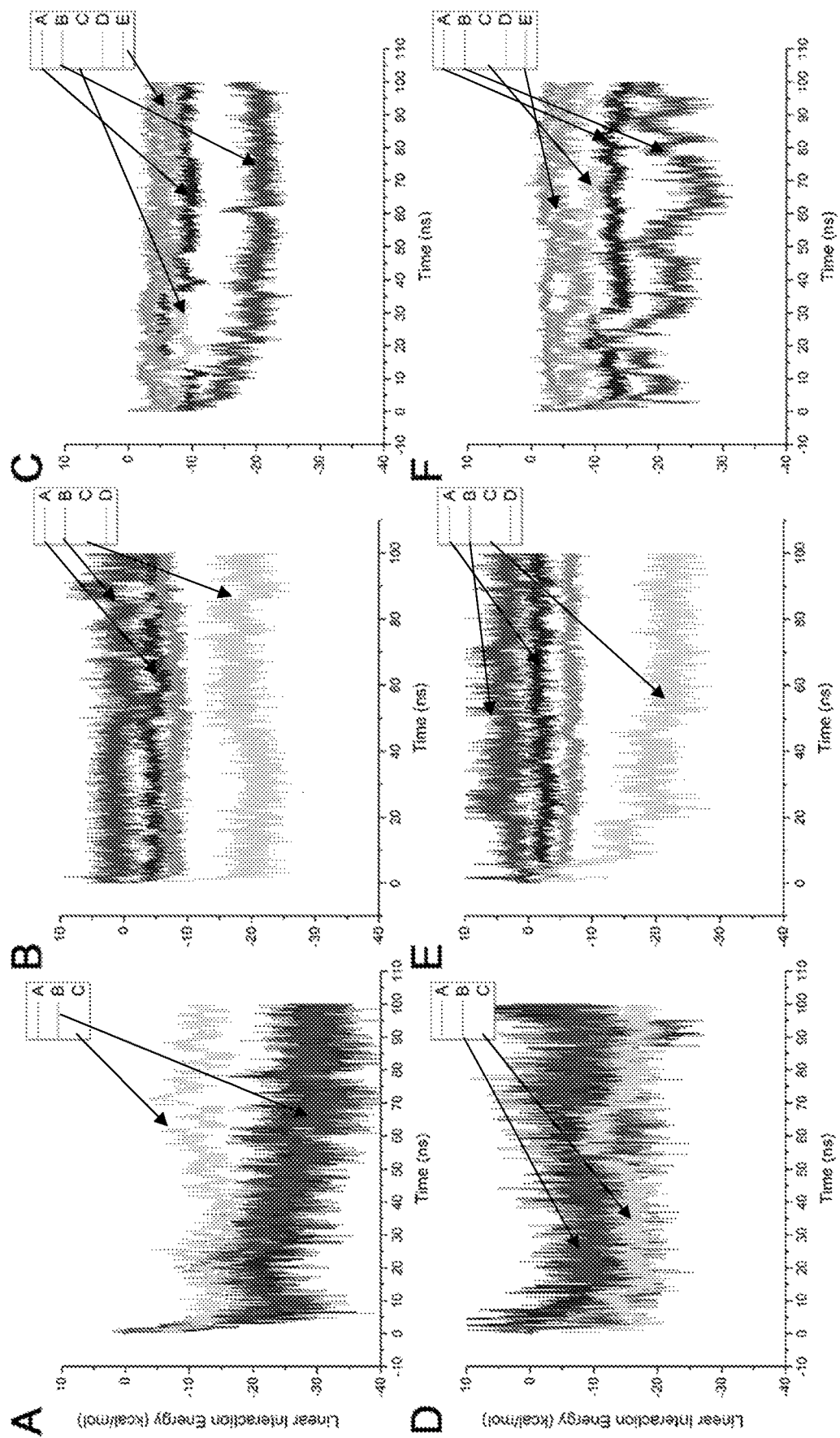
FIG. 13 shows (A-F) Linear interaction energies between silica surface and specific groups of maleimide dye atoms. (A-C) 1% deprotonated silica surface, (D-F) 15% deprotonated silica surface. (A, D) Cy5, (B, E) TMR, and (C, F) ATTO647N. (G-I) Illustrations of atom groupings for Cy5 (G), TMR (H), and ATTO647N (I), respectively. Group interactions highlight how the charged sections of the dye molecule dominate interactions with the silica surface.
Figure 13:
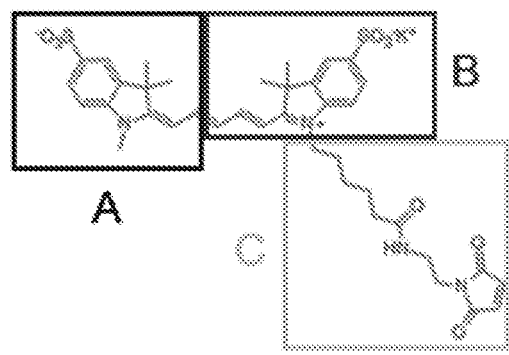
Figure 13:
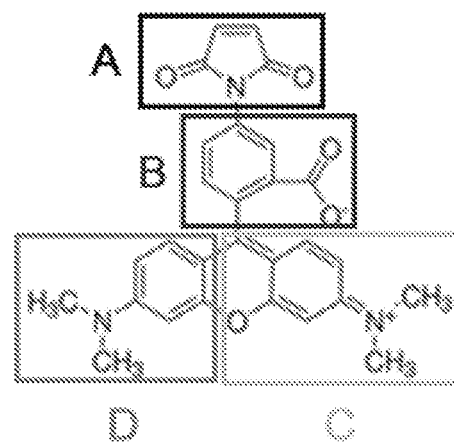
Figure 13:
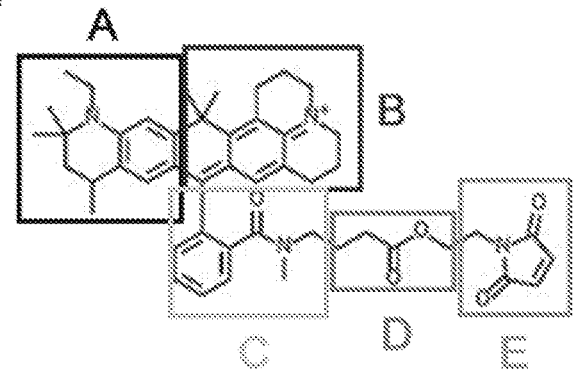

To further elucidate the observed differences in dye incorporation efficiency and dye location either on the surface or in the core of the particle, we performed all-atom molecular dynamics (MD) simulations. Atomistic MD has been extensively employed to silica surfaces and their interactions with silanes and other organics. Systems of amorphous silica were constructed with a given surface charge (ratio of $SiO^-/SiOH$ units available on the surface referred to as the deprotonation percentage), a single dye molecule, water, and the number of ammonium ions necessary to reach a net-neutral system charge (FIG. 5A, for dimensions see FIG. 11). The resulting total linear interaction energies between the silica surfaces and the dye silanes over the last 20 ns of the production simulations are shown in FIG. 5B. These values are the non-bonded energies between the surface and the dye calculated from the simulation trajectory: large negative values indicate strong attraction, whereas positive values indicate repulsion (for details see FIG. 12). Results indicate that all three dyes have a similarly affinity to the passivated surface of a fully-formed nanoparticle (with Cy5 potentially being slightly more attracted) as represented by the 1% deprotonated surface. A more-negatively-charged 15% deprotonated surface, representative for intermediate silica cluster surfaces during synthesis, shows unchanged affinity for TMR and ATTO647N. In contrast, Cy5 shows little to slightly repulsive interaction, suggesting that Cy5 is less attracted to these clusters and therefore less likely to be incorporated into the core of the particle. Moreover, analyzing the interaction energies between specific atomic groups within the dye molecules and the silica surface (FIG. 13) provides evidence that these interactions are indeed driven by electrostatics, consistent with experiments. For example, the electrostatic repulsion between Cy5 and the 15% deprotonated surface is the strongest interaction measured, as described herein.

The highest degree of particle homogeneity in surface chemical properties was obtained for PEG-MB2-C' dots (see FIG. 4). For a synthesis batch of these particles, the same coupled GPC-HPLC experiment was conducted as described for PEG-Cy5-C' dots. When PEG-MB2-C' dots were fractionated with GPC, normalized in concentration, and subjected to HPLC, again there was no substantial dependence of the surface chemical properties on particle size (FIG. 2C). Detailed comparison of different fractions further revealed that there was a small increase in surface bound dyes with particle size (FIG. 2E), similar to PEG-Cy5-C' dots. These experiments corroborated earlier conclusions for PEG-Cy5-C' dots that for this synthesis approach to fluorescent core-shell silica nanoparticles heterogeneities in particle size and surface chemical properties are essentially uncorrelated. Comparison of waterfall plots in FIGS. 2A and C for PEG-Cy5-C' dots and PEG-MB2-C' dots illustrate the remarkable control in particle batch surface chemical homogeneity that can be achieved by the appropriate choice of dye chemistry.

UHPLC grade acetonitrile was purchased from BDH. Superdex 200 resin was purchased from GE Healthcare Life Sciences. Vivaspin 30 k MWCO spin filters were purchased from GE Healthcare Life Sciences. 5 M NaCl in water solution was purchased from Santa Cruz Biotechnology. Dimethyl sulfoxide (DMSO), Tetramethyl orthosilicate (TMOS), (3-Mercaptopropyl)trimethoxysilane (MPTMS), 2.0 M ammonia in ethanol were all purchased from Sigma- Aldrich. Methoxy-PEG(5-9)-silane (500 g/mol) was purchased from Gelest. Cy5-maleimide, Cy5.5-maleimide, Cy3-maleimide were purchased from GE. TMR-maleimide (tetramethylrhodamine) purchased from Life Technologies. Alexa Fluor 647-COOH was purchased from Thermo Fisher. DI water generated using Millipore Milli-Q system (Milli-Q, 18.2 MΩ·cm). Atto647N-maleimide, Atto680-maleimide, and MB2-maleimide were purchased from Atto-Tec Gmbh. Xbridge Protein BEH C4 Column (300 Å, 3.5 μm, 4.6 mm×150 mm, 10K-500K) and BioSuite. High Resolution SEC Column (250 Å, 5 μm, 7.8 mm×300 mm, 10K-500K) were purchased from Waters Technologies Corporation. Streptavidin and N-γ-maleimidobutyryl-oxysuccinimide ester (GMBS) were purchased from Life Technologies. All chemicals were used as received without further purification.

Particle Synthesis. Cy5, TMR, Cy3, and Atto680 C' dots were synthesized as previously described. Briefly, a mono functional maleimido derivatized dye was dissolved in DMSO overnight in a glovebox. A 25-fold excess of mercaptopropyltrimethoxysilane was added to the dissolved dye and allowed to react overnight in the glove box. The next day, a flask containing deionized water adjusted to pH 8 using 2.0 M ammonia in ethanol solution was prepared and stirred vigorously. Tetramethylorthosilicate (TMOS) and the prepared dye-silane conjugate were added to the flask and allowed to react overnight. The following day, 100 uL of mPEG(5-9)-silane was added to the flask and allowed to react overnight. The following day the stirring of the solution was stopped and the flask was heated to 80° C. for 24 hours. Following this the particles are extensively dialyzed using 10 k MWCO cellulose dialysis tubing, followed by syringe filtration with a 200 nm membrane, spin filtering with a 30 k MWCO PES membrane spin filter and finally GPC purification through Superdex 200 resin on a Bio-Rad FPLC. The particles are then characterized using fluorescence correlation spectroscopy on a home-built setup and UV/Vis spectroscopy on a Cary 5000 spectrometer. Atto647N and MB2 C' dots have a slight adjustment to the protocol, for a 10 mL reaction 2 mL of 0.02 M $NH_4OH$ solution and 8 mL of DI water are added to the reaction flask instead of the previously reported 1 mL the resultant increase in pH was used to decrease the final size of the nanoparticles, as dyes with positive charges tend to form larger nanoparticles under standard conditions.

High Performance Liquid Chromatography (HPLC). All HPLC runs were carried out on a Waters Alliance 2965 separations module equipped with a column heater, a Waters 2424 evaporative light scattering detector, and a Waters 2996 photodiode array detector. The sample loop was 50 the standard size for an analytical system. The hardware was controlled by a computer running Empower 3 Feature Release 2 and all chromatograms were analyzed using the ApexTrack peak integration algorithm. Deionized water was generated from a Millipore Milli-Q water system (18.2 MΩ resistivity) and acetonitrile was obtained from BDH (UHPLC grade). The columns used were 150 mm Waters Xbridge BEH C4 Protein separation columns with 300 Å pore size and 3.5 μm particle size. All injections were 8 μL of 15 μM C' dots. Concentrations for injected samples were determined by FCS. The separation method used is as follows: The sample was first injected onto the column in a flow of 90:10 water:acetonitrile at a flow rate of 1 mL/min. These conditions were maintained for 20 minutes to allow equilibration of the analyte with the stationary phase. After 20 minutes the flow rate was slowed to 0.5 mL/min and the baseline was allowed to equilibrate. Then the mobile phase composition was changed to 45:55 water:acetonitrile in a step-like fashion and the baseline was allowed to equilibrate again. Finally a composition gradient of 45:55 to 5:95 water:acetonitrile was carried out for 20 minutes, during this time the analyte elutes from the column. The analytical run above was followed by a short washing step and column equilibration period to ensure that all material from the previous run had eluted from the column and that the column conditions for the next sample analysis were identical to those for the previous sample analysis. In addition to the above method, the same separation method can be used with a constant flow rate of 0.75 mL/minute for the entirety of the experiment for identical results. The use of either method is based entirely on preference, as flow rate changes between 0.5 mL/min and 1 mL/min do not have any drastic effect on the particle separation. The data was collected and analyzed in Empower 3. The ApexTrack integration algorithm native to the Empower 3 software was used to identify peaks and determine the area percentage associated with each eluting peak. For plotting purposes, data was exported after analysis and baseline subtracted with a blank taken before the chromatographic run using OriginLab. For a comparison between baseline subtracted and raw data, see FIG. 9.

Analytical Gel Permeation Chromatography. Analytical scale gel permeation chromatography was performed on as made solutions prior to preparative scale GPC purification. Injection volumes were 30 μL of native synthesis solution diluted with 70 μL of deionized water for a final injection volume of 100 μL. The solution used was the same as the preparative scale GPC solution, prepared the same way directly prior to injection. The column used was a 300 mm Water BioSuite High Resolution Size Exclusion Chromatography column. The separations were performed under isocratic conditions with a flow rate of 1 mL/min. Particle samples including free dye and unreacted PEG-silane eluted within 30 minutes, but the column was run for an additional 20 minutes to ensure that all material had eluted during the chromatographic run.

Dye incorporation efficiency was calculated by using the ApexTrack integration algorithm native to the Empower3 software used to control the instrument and collect data. The peak area percentage attributed to dye at the absorption maximum of the dye is taken to be the percentage of dye successfully incorporated in the nanoparticle.

Gel Permeation Chromatography (GPC). Preparative scale gel permeation chromatography was carried out on a Bio-Rad FPLC equipped with a UV detector set to 275 nm and a conductivity detector. Particles were purified in isocratic mode using 0.9 wt. % NaCl in deionized water. The solution was prepared at the time of purification by diluting 0.2 μm membrane filtered 5 M NaCl in water (Santa Cruz Biotechnology) with deionized water. The column used was hand-packed with Superdex 200 resin with dimensions 20 mm×300 mm and run at a flow rate of 2.0 mL/min. All samples were concentrated in GE Life Sciences 30 kDa MWCO VivaSpin filters prior to injection the total injection volume was less than 1 mL per run. Particles eluted around the 15 minute mark and the total run lasted 30 minutes.

Steady-State Absorption Spectroscopy. Absorbance spectra of particle samples and dye were measured in DI water on a Varian Cary 5000 spectrophotometer in a 3 mL quartz cuvette with a 10 mm light path (HellmaAnalytics) from 200 nm to 800 nm in 1 nm increments. All spectra were baseline corrected using a cuvette with DI water as reference cell. Peak intensities were kept between 0.01 and 0.06.

Fluorescence Correlation Spectroscopy (FCS). All FCS measurements were carried out on a homebuilt confocal FCS setup. In short, a continuous wave laser beam (635 nm solid state laser for particle containing Cy5, ATTO647N, or ATTO680, and a 543 nm HeNe laser for particles containing TMR, or Cy3) is focused onto the image plane of a water immersion microscope objective (Zeiss Plan-Neofluar 63×NA 1.2). The stokes-shifted emitted fluorescence is collected by the same objective, passed through a dichroic mirror, spatially filtered by a 50 µm pinhole, split into two paths with a beam splitter, spectrally filtered by long pass filters (ET6651p, Chroma, for 635 nm excitation, and ET5601p, Chroma, for 543 nm excitation), and detected by two avalanche photodiode detectors (SPCM-AQR-14, PerkinElmer). To filter detector afterpulsing effects from sample fluorescence fluctuations, the detector signals were cross-correlated by a digital correlator (Flex03LQ, Correlator.com)(38), allowing lag time resolution of 15 ns. Respective correlation curves were fitted accounting for translational diffusion, photo-induced cis-trans isomerization, and rotational diffusion by using equation (1):

$$G(\tau) = 1 + \frac{1}{N_m}\left(\frac{1}{1+\tau/\tau_D}\right)\left(\frac{1}{1+\tau/(\tau_D\kappa^2)}\right)^{1/2} \quad (1)$$

$$\frac{1}{(1-P)}(1 - P + P\exp(\tau/\tau_P))(1 + \alpha_{Rot}\exp(\tau/\tau_{Rot}))$$

where $N_m$ is the number of dye molecules or particles in the ellipsoidal observation volume, defined by a structure factor $\kappa=\omega_z/\omega_{xy}$ with axial ($\omega_z$) and radial ($\omega_{xy}$) radii. $\tau_D$ is the characteristic diffusion time of a dye or particle through the observation volume. P is the fraction of Cy5 dye molecules being in the non-fluorescent (or weakly fluorescent) cis-conformation, which the characteristic relaxation time $\tau_p$. For particles a third relaxation time is noticeable at very short lag times ($\tau$=100 ns) that can be attributed to particle rotation, where $\alpha_{Rot}$ is the pre-exponential amplitude of particle rotation, and $\tau_{Rot}$ the characteristic rotational diffusion time of a particle. Particle rotation was not further characterized and only used for improved fits. All correlation curves were normalized according to equation (2):

$$G(\tau)=(G(\tau)-1)N_m \quad (2)$$

The FCS observation volume $V_{eff}$ was calibrated before each measurement by diluting a dye stock solution with DI water to nanomolar concentrations and determining the structure factor with a standard dye (Alexa Fluor for 635 nm laser and TMR for 532 nm laser). To avoid singlet-triplet transitions in Cy5 dye, all measurements were carried out at 5 kW cm$^{-2}$. All FCS samples were measured five times in five individual 30 s runs in a 35 mm glass bottom dish (P35G-1.5-10-C, Mattek Corporation) at nanomolar concentration in DI water at 20° C. The particle diameters, d, were determined from the fits using equation (3) and (4):

$$D = \frac{\omega_{xy}^2}{4\tau_D} \quad (3)$$

$$d = 2\frac{k_B T}{6\pi\eta D} \quad (4)$$

where D is the diffusion constant. Since cis-trans isomerization of co-diffusion Cy5 molecules is independent from each other, the amplitude of isomerization, $\alpha$, appears smaller, for particles carrying more than one Cy5 molecule.

Therefore, P needs to be adjusted for the average number of dyes per particle, $n_m$, using equations (5) and (6):

$$P=\alpha/(1+\alpha) \quad (5)$$

$$\alpha=\alpha_p/n_m \quad (6)$$

To determine $n_m$ the measured optical density of each sample was compared to the mean particle concentration as obtained by FCS using equation (7):

$$n_m = \frac{C_{Abs}}{\langle C \rangle_{FCS}} \quad (7)$$

Total Internal Reflection Fluorescence Microscopy (TIRFM). Samples for photobleaching experiments were prepared by immobilizing biotinylated particles on streptavidin coated glass slides. Streptavidin coated slides were prepared by binding streptavidin via GMBS and MPTMS to a plasma cleaned glass bottom slide (P35G-1.5-14-C, Mattek Corporation) as previously described. Free particles were removed by rinsing the slides with PBS twice before covering the sample with 1 mL of PBS and a glucose oxidase/catalase oxygen scavenger system. Single particle imaging was performed on an inverted Zeiss Elyra microscope operated at TIRF angles of 62-65° as indicated in the Zen 2012 (Zeiss) software, using a 1.46 NA 100× oil immersion objective, and 642 nm laser (laser power 0.165 mW, measured at the objective) with typical integration times of 100 ms per frame. Fluorescence emission was spectrally filtered with a 655 nm long pass filter. Each movie was recorded at 10 Hz until 99% of the initial fluorescence signal decayed. The excitation laser was turned on right after the photobleaching movie recording was started. The "Definite focus" focal-drift compensation was activated during data acquisition. To avoid overlapping point spread functions only samples that were sparsely labeled with particles were included in the analysis.

Single Particle Photobleaching Analysis. To analyze the recorded movies *.zvi files were loaded into ImageJ and converted to 8-bit *.tiff files. Individual particle fluorescence time traces (arbitrary units, A.U.) were extracted using the custom software (ImageC.exe), developed and kindly provided by Dr. Warren Zipfel (Cornell University, NY, USA). Due to sparse labeling it was assumed that each point spread functions (PSF) in the image represents one particle. Particles were automatically located from the summed projection of the image stack by applying a Gaussian mask algorithm. Particle fluorescence time trace were the summed pixel intensities of 5×5 region of interest (ROI) centered around the brightest pixel and plotted against measurement time. The brightest pixel was maintained as the center of each ROI for each frame. Due to shot noise variations and possible minor drift, the ROI was allowed to move at most 1 pixel per frame. Fluorescence bleaching steps were counted by hand. Traces with undiscernable bleaching steps were rejected from the analysis. A total number of 644 particles were analyzed.

Simulations. All-atom molecular dynamics (MD) simulations were performed using the AMBER 16 molecular dynamics package. All dye molecules were constructed in Discovery Studio Visualizer and assigned force field parameters from the general AMBER force field (GAFF) version 1.8. Dyes with attached silane units also included force field parameters from the CHARMM silicate force field applied to silicon and silicon-adjacent atoms. Partial charges were assigned to the dye molecules via the restrained electrostatic potential (R.E.S.P.) method using R.E.S.P. ESP charge Derive (R.E.D.) Server Development. During R.E.S.P. calculations, the net molecule charge and the local charge on atoms shown with a formal charge were restrained. All dye molecules were individually energy minimized in vacuum prior to their addition to surface-solvent systems.

Systems containing silica surfaces, dye, and water were constructed by first copying and translating the coordinates for an amorphous silica surface in to create a bonded silica surface approximately 80×80×20 Å in the x, y, and z directions, respectively. Hydrogens were randomly removed to reach the desired deprotonation percentage, followed by changing the dangling oxygen atom types and partial charges as necessary. The target dye molecule was then added to the system with a center-of-mass 4-9 Å above the surface in the positive z-direction, with the distance chosen to ensure that the dye does not overlap with the silica surface after addition. The dye molecule was then randomly rotated by first choosing a random unit vector through the molecule center-of-mass as the axis of rotation and then a random angle between 0 and $2\pi$ by which to rotate the dye molecule. For each surface-dye combination, five independent systems differing only by this random dye molecule rotation were created and simulated. Reported linear interaction energies are the average of these five simulations. The dye molecule and silica surface were then solvated with TIP3P water using a buffer distance of 40 Å in the positive and negative z-directions. Random water molecules were then removed and replaced by positively-charged ammonium ions to reach a net neutral charge for the entire system. Thus, the starting simulation coordinates were approximately 80×80×130 Å with 85,000-95,000 atoms total. A visualization of a representative starting system conformation with Cy5 maleimide is shown in FIG. 5A and FIG. 9.

All simulations utilized periodic boundary conditions, the Langevin thermostat with a collision frequency of 2 $ps^{-1}$, the Berendsen barostat (if NPT ensemble) with a relaxation time of 1 ps, and a van der Waals cutoff value of 8 Å with long-range electrostatics calculated via the Particle Mesh Ewald method. Prior to production simulations, each system was independently equilibrated with the silica surface and dye molecule harmonically restrained with a force constant of 5.0 kcal/mol by the following five-step procedure: (1) structural energy minimization, (2) a constant-volume (NVT ensemble) heating step from 0 to 300 K at a rate of 3 K/ps, (3) an NVT equilibration step at 300 K for 0.3 ns, (4) a constant-pressure (NPT ensemble) equilibration step at 1 atm and 300 K for 0.5 ns, and (5) an NPT equilibration step at 1 atm and 300 K with a timestep of 2 fs and the SHAKE algorithm applied to covalent bonds involving a hydrogen for 1 ns (steps 1 to 4 used a 1 fs timestep). Production simulations, from which all reported data was calculated, were performed in the NPT ensemble at 1 atm and 300 K with a timestep of 2 fs for 100 ns. Linear interaction energies were calculated using AMBER's cpptraj post-processing software.

TABLE T1

Particle size and dyes per particle of the various C' dots used in the paper. For samples subjected to fluorescence correlation spectroscopy, photoisomerization and brightness per dye is also tabulated.

| Sample | Diameter (nm) | Dyes/ Particle (#) | Photoisom- erization P (%) | Bright- ness/Dye (kHz) |
|---|---|---|---|---|
| Cy5 (free dye) | 1.3 | 1.0 | 43.2 | 7881 |
| PEG-Cy5-C' dots | 5.8 | 1.6 | 35.2 | 17443 |
| PEG-Cy5-C' dots Peak 1 | 5.6 | 1.5 | 33.2 | 18203 |
| PEG-Cy5-C' dots Peak 2 | 5.8 | 2.0 | 37.8 | 14203 |
| PEG-Cy5-C' dots Peak 3 | 5.7 | 2.3 | 41.3 | 12424 |
| PEG-TMR-C' dots | 6.4 | 3.6 | — | — |
| PEG-ATTO647N-C' dots | 6.2 | 2.0 | — | — |
| PEG-ATTO680-C' dots | 7.0 | 1.4 | — | — |
| PEG-MB2-C' dots | 4.3 | 2.6 | — | — |

TABLE T2

Peak integration areas and retention times for native synthesis solution of PEG-TMR-C' dots shown in FIG. 7 as determined by Empower3 software using the ApexTrack peak detection algorithm.

| Peak Number | Retention Time (min) | Area (%) |
|---|---|---|
| 1 | 5.784 | 0.59 |
| 2 | 8.622 | 82.08 |
| 3 | 10.477 | 5.68 |
| 4 | 20.704 | 4.22 |
| 5 | 23.231 | 7.42 |

TABLE T3

Peak integration areas and retention times for native synthesis solution of PEG-Cy5-C' dots shown in FIG. 8 as determined by Empower3 software using the ApexTrack peak detection algorithm.

| Peak Number | Retention Time (min) | Area (%) |
|---|---|---|
| 1 | 9.037 | 62.11 |
| 2 | 11.946 | 7.45 |
| 3 | 13.412 | 30.44 |

TABLE T4

Peak integration areas and retention times for native synthesis solution of PEG-ATTO647N-C' dots shown in FIG. 9 as determined by Empower3 software using the ApexTrack peak detection algorithm.

| Peak Number | Retention Time (min) | Area (%) |
|---|---|---|
| 1 | 6.306 | 1.47 |
| 2 | 8.87 | 98.53 |

TABLE T5

Peak integration areas as determined with ApexTrack integration in Empower 3 for the HPLC chromatogram of PEG-Cy5-C' dots as shown in FIG. 1B.

| Peak Number | Retention Time (min) | Area (%) |
|---|---|---|
| 1 | 30.940 | 27.68 |
| 2 | 31.779 | 37.70 |
| 3 | 32.725 | 28.65 |
| 4 | 33.785 | 5.96 |

Example 3

This example describes fluorescent core-shell silica nanoparticles with improved optical and surface chemical properties from ATTO647N dye Highly fluorescent sub-10 nm PEGylated core-shell silica nanoparticles synthesized in water referred to as C prime dots (C' dots), have been demonstrated as a promising nanomaterials platform for theranostic applications in nanomedicine. The majority of past experiments were performed with particles covalently incorporating the near-infrared (NIR) absorbing and fluorescing dye Cyanine5 (Cy5). Particle analysis with high performance liquid chromatography (HPLC) has shown, however, that Cy5 gets poorly encapsulated into the silica matrix due to electrostatic repulsion between negative charges on dye and matrix. Here, we turn our attention to positively charged NIR dye ATTO647N with similar absorption and emission characteristics to Cy5. We demonstrate that replacing Cy5 with ATTO647N leads to C' dots with similar size and brightness. In depth characterization reveals, however, that a number of other physicochemical particle properties including surface-chemical homogeneity, stability against chemical degradation, and photobleaching stability, are substantially improved, rendering these ATTO647N based C' dots a promising new particle platform for nanomedicine.

It is therefore desirable to employ a positively charged dye in the C' dot synthesis that will be attracted to the growing silica, thus potentially improving the encapsulation efficiency and particle surface chemical properties. A possible candidate dye with optical characteristics similar to Cy5 is the carbo-rhodamine dye ATTO647N. ATTO647N is considerably more photo-stable than Cy5 due to its chemical structure, which is why it is often used as a stimulated emission depletion super-resolution microscopy (STED) probe, yet possesses limitations such as π-π stacking induced quenching when in aqueous environments. Presented is how covalent encapsulation of ATTO647N into the C' dot silica network alters particle properties relative to Cy5 based C' dots, including improved surface chemical homogeneity, stability against chemical degradation, and photobleaching stability. This renders these third generation ATTO647N based C' dots a promising new particle platform for applications including bioimaging and nanomedicine.

Methods and Materials. All chemicals were used as received without further purification. Dimethyl sulfoxide (DMSO), (3-mercaptopropyl) trimethoxysilane (MPTMS), tetramethylorthosilicate (TMOS), and ammonium hydroxide ($NH_4OH$) were purchased from Sigma-Aldrich. UHPLC grade acetonitrile was purchased from BDH. Superdex 200 resin was purchased from GE Healthcare Life Sciences. Vivaspin 30 k MWCO spin filters were purchased from GE Healthcare Life Sciences. 5 M NaCl in water solution was purchased from Santa Cruz Biotechnology. 2-[methoxy (polyethyleneoxy)6-9propyl] trimethoxysilane and tech-90 (PEG-silane, molar mass around 500 g/mol) were purchased from Gelest. Cy5-maleimide was purchased from GE, Alexa Fluor 647-COOH was purchased from Thermo Fisher, and ATTO647N-maleimide was purchased from Atto-Tec Gmbh. Heterobifunctional PEGs functionalized with both NHS ester and maleimide, were purchased from Quanta BioDesign. Cyclic c(RGDyC) peptide was purchased from Peptide International. DI water was generated using a Millipore Milli-Q system. The Xbridge Protein BEH C4 Column (300 Å, 3.5 μm, 4.6 mm×150 mm, 10K-500K) and BioSuite High Resolution SEC Column (250 Å, 5 μm, 7.8 mm×300 mm, 10K-500K) were purchased from Waters Technologies Corporation.

Particle Synthesis. Cy5-C' dots were synthesized as previously described. Briefly, a mono functional maleimido derivatized dye was dissolved in DMSO overnight in a glovebox. ATTO647N-C' dots had a slight adjustment to the protocol: For a 10 mL reaction 2 mL of 0.02 M $NH_4OH$ solution and 8 mL of DI water were added to the reaction flask instead of the previously reported 1 mL of 0.02 M $NH_4OH$; the resultant increase in pH was used to decrease the final size of the nanoparticles, as dyes with positive charges tend to form larger nanoparticles under standard conditions. A 25-fold excess of MPTMS was added to the dissolved dye and allowed to react overnight in the glove box. The next day a flask containing deionized water adjusted to pH 8 using 2.0 M ammonia in ethanol solution was prepared and stirred vigorously. TMOS and the prepared dye-silane conjugate were added to the flask and allowed to react overnight. The following day, 100 μL of PEG-silane was added to the flask and allowed to react overnight. The following day the stirring of the solution was stopped and the flask was heated to 80° C. for 24 hours. Following this, the particles were extensively dialyzed using 10 k MWCO cellulose dialysis tubing, followed by syringe filtration with a 0.2 μm membrane, spin filtering with a 30 k MWCO PES membrane spin filter and finally GPC purification through Superdex 200 resin on a Bio-Rad FPLC. The particles were then characterized using fluorescence correlation spectroscopy (FCS) on a home-built setup and UV/Vis spectroscopy on a Cary 5000 spectrometer.

Transmission Electron Microscopy. Transmission electron microscopy (TEM) images are taken using a FEI Tecnai T12 Spirit microscope operated at an acceleration voltage of 120 kV. Nanoparticle suspensions were diluted with ethanol and 10 μL of solution were placed on grids and allowed to completely dry.

High Performance Liquid Chromatography (HPLC). All HPLC runs were carried out on a Waters Alliance 2965 separations module equipped with a column heater and a Waters 2996 photodiode array detector. The sample loop was 50 μL, the standard size for an analytical system. The hardware was controlled by a computer running Empower 3 Feature Release 2 and all chromatograms were analyzed using the ApexTrack peak integration algorithm. Deionized water was generated from a Millipore Milli-Q water system (18.2 MΩ resistivity) and acetonitrile was obtained from BDH (UHPLC grade). The columns used were 150 mm Waters Xbridge BEH C4 Protein separation columns with 300 Å pore size and 3.5 μm particle size. All injections were 8 μL of 15 μM C' dots. Concentrations for injected samples were determined by FCS as described above. The separation method used was as follows: The sample was first injected onto the column in a flow of 90:10 water:acetonitrile at a flow rate of 1 mL/min. These conditions were maintained for 20 minutes to allow equilibration of the analyte with the stationary phase. After 20 minutes the flow rate was slowed to 0.5 mL/min and the baseline allowed to equilibrate. The mobile phase composition was then changed to 45:55 water: acetonitrile in a step-like fashion and the baseline was allowed to equilibrate again. Finally, a composition gradient of 45:55 to 5:95 water:acetonitrile was carried out for 20 minutes. During this time the analyte elutes from the column. The analytical run described above was followed by a short washing step and column equilibration period to ensure that all material from the previous run had eluted from the column and that the column conditions for the next sample analysis were identical to those for the previous sample analysis. In addition to the above method, the same separation gradient could be used with a constant flow rate of 0.75 mL/minute for the entirety of the experiment for identical results. The use of either method was based entirely on preference and column life, as flow rate changes between 0.5 mL/min and 1 mL/min do not have any drastic effect on the particle separation but a lower flow rate during the gradient section of the method can allow an older, less well maintained column to perform this separation well for a longer period of time. The data was collected and analyzed in Empower 3. The ApexTrack integration algorithm native to the Empower 3 software was used to identify peaks and determine the area percentage associated with each eluting peak.

Preparative Gel Permeation Chromatography (GPC). Preparative scale gel permeation chromatography (GPC) was carried out on a Bio-Rad FPLC equipped with a UV detector set to 275 nm and a conductivity detector. Particles were purified in isocratic mode using 0.9 wt. % NaCl in deionized water. The solution was prepared at the time of purification by diluting 0.2 µm membrane filtered 5 M NaCl in water (Santa Cruz Biotechnology) with deionized water. The column used was hand-packed with Superdex 200 resin with dimensions 20 mm×300 mm and run at a flow rate of 2.0 mL/min. All samples were concentrated in GE Life Sciences 30 kDa MWCO VivaSpin filters prior to injection. The total injection volume was less than 1 mL per run. Particles eluted around the 15 minute mark, and the total run lasted 30 minutes.

Analytical Gel Permeation Chromatography. Analytical scale gel permeation chromatography was performed on as made solutions prior to preparative scale GPC purification. Injection volumes were 30 µL of native synthesis solution diluted with 70 µL of deionized water for a final injection volume of 100 µL. The solution used was the same as the preparative scale GPC solution, prepared the same way directly prior to injection. The column used was a 300 mm Water BioSuite High Resolution Size Exclusion Chromatography column. The separations were performed under isocratic conditions with a flow rate of 1 mL/min. Particle samples including free dye and unreacted PEG-silane eluted within 30 minutes, but the column was run for an additional 20 minutes to ensure that all material had eluted during the chromatographic run.

Dye incorporation efficiency was calculated by using the ApexTrack integration algorithm native to the Empower3 software used to control the instrument and collect data. The peak area percentage attributed to dye at the absorption maximum of the dye was taken to be the percentage of dye successfully incorporated in the nanoparticle.

Steady-State Absorption Spectroscopy. Absorbance spectra of particle and dye samples were measured in DI water on a Varian Cary 5000 spectrophotometer in a 3 mL quartz cuvette with a 10 mm light path (HellmaAnalytics) from 200 nm to 800 nm in 1 nm increments. All spectra were baseline corrected using a cuvette with DI water as reference cell. Peak intensities were kept between 0.01 and 0.06. Spectral emission correction spectra were recorded on a Photon Technologies International Quantamaster spectrofluorometer.

Fluorescence Correlation Spectroscopy (FCS). All fluorescence correlation spectroscopy (FCS) measurements were carried out on a homebuilt confocal FCS setup. In short, a continuous wave 635 nm solid state laser beam was focused onto the image plane of a water immersion microscope objective (Zeiss Plan-Neofluar 63×NA 1.2). The stokes-shifted emitted fluorescence was collected by the same objective, passed through a dichroic mirror, spatially filtered by a 50 µm pinhole, split into two paths with a beam splitter, spectrally filtered by long pass filters (ET6651p, Chroma, for 635 nm excitation) and detected by two avalanche photodiode detectors (SPCM-AQR-14, PerkinElmer). To filter detector afterpulsing effects from sample fluorescence fluctuations, the detector signals were cross-correlated by a digital correlator (Flex03LQ, Correlator.com), allowing lag time resolution of 15 ns. Respective correlation curves were fitted accounting for translational diffusion, photo-induced cis-trans isomerization, and rotational diffusion by using equation:

$$G(\tau) = 1 + \frac{1}{N_m}\left(\frac{1}{1+\tau/\tau_D}\right)\left(\frac{1}{1+\tau/(\tau_D\kappa^2)}\right)^{1/2}$$

$$\frac{1}{(1-P)}(1 - P + P\exp(\tau/\tau_P))(1 + \alpha_{Rot}\exp(\tau/\tau_{Rot}))$$

where $N_m$ is the number of dye molecules or particles in the ellipsoidal observation volume, defined by a structure factor $\kappa = \omega_z/\omega_{xy}$, with axial ($\omega_z$) and radial ($\omega_{zy}$) radii. $\tau_D$ is the characteristic diffusion time of a dye or particle through the observation volume. P is the fraction of Cy5 and ATTO647N dye molecules in either the non-fluorescent cis-conformation (Cy5) or triplet state (ATTO647N), with the characteristic relaxation time $\tau_P$. For particles, a third relaxation time is noticeable at very short lag times ($\tau \approx 100$ ns) that can be attributed to particle rotation, where $\alpha_{Rot}$ is the pre-exponential amplitude of particle rotation, and $\tau_{Rot}$ the characteristic rotational diffusion time of a particle. Particle rotation was not further characterized and only used for improved fits. All correlation curves were normalized according to equation:

$$G(\tau) = (G(\tau) - 1)N_m$$

The FCS observation volume, $V_{eff}$, was calibrated before each measurement by diluting a dye stock solution with DI water to nanomolar concentrations and determining the structure factor with a standard dye (Alexa Fluor for 635 nm laser). To avoid singlet-triplet transitions in dyes, all measurements were carried out at 5 kW cm$^{-2}$. All FCS samples were measured five times in five individual 30 s runs in a 35 mm glass bottom dish (P35G-1.5-10-C, Mattek Corporation) at nanomolar concentration in DI water at 20° C. The particle diameters, d, were determined from the fits using equations:

$$D = \frac{\omega_{xy}^2}{4\tau_D}$$

$$d = 2\frac{k_B T}{6\pi\eta D}$$

where D is the diffusion constant. To determine concentration of nanoparticles, $n_m$, the measured optical density of each sample was compared to the mean particle concentration as obtained by FCS using equation:

$$n_m = \frac{C_{Abs}}{\langle C \rangle_{FCS}}$$

Determination of Relative Fluorescence Quantum Yields. The relative fluorescence quantum yield, $\Phi_F$, of different samples (Cy5-C'dots, ATTO647N-C'dots) were measured at room temperature in deionized water using absorbances between 0.01 and 0.09 to minimize effects of reabsorption. Samples were excited at 645 nm and fluorescence recorded from 655 nm to 800 nm. All quantum yields were determined against Cy5 ($\Phi_F$=0.28/0.20) as a standard:

$$\Phi_{F,i} = \Phi_{F,ref} \frac{A_{ref}}{A_i} \frac{\int I_i(\lambda)d\lambda}{\int I_{ref}(\lambda)d\lambda}$$

where $\Phi_{F,i}$ is the fluorescent quantum yield, $I_i$ is the fluorescence mean intensity of a sample or a reference, and $\int I_i(\lambda)d\lambda$ is the integrated fluorescence from 655 nm to 800 nm.

Ensemble Photobleaching Measurements. Photobleaching measurements were conducted in 100 µL quartz cuvettes using a 100 mW expanded and collimated 642 nm laser. Absorption spectra were taken at defined time intervals. The decrease in absorption was plotted against exposure time.

Cell Study. MDA-MB-231 cells were obtained from ATCC, which validated them with short tandem repeat (STR) analysis, and used within 3 months. Cells were maintained in RPMI 1640 supplemented with 10% FBS at 37° C. with 5% $CO_2$ in the presence of C' dots. To measure effects of C' dots on cells, cells at ~70% confluence were washed with PBS, exposed to trypsin, resuspended, and dispensed into 96-well tissue culture plates (20,000 cells per well). Cells were allowed to settle overnight, forming a monolayer ~70-80% confluent. Cells were then incubated for 6 days. Following incubation, medium was removed, cells washed with fresh medium and then incubated for one hour with fresh medium and Presto Blue per the manufacturer's recommendations. The absorbance of the Presto Blue was determined at 570 nm (background 600 nm) using a Tecan Safire microplate reader. Absorption was compared to that of a blank (medium plus Presto Blue in unused wells) to determine % viability of remaining cells, with the DMSO control lane defined as 100% viability, and the empty wells defined as 0% viability.

Lifetime Measurements. Lifetime measurements were taken using a 440 nm pulsed excitation (Becker&Hickl BDL-SMN-440 pulsed diode laser with ~100 ps pulsewidth), a Becker & Hickl SPC-830 Time-Correlated Single Photon Counting (TCSPC) card and Hamamatsu R3809U-50 microchannel plate photomultiplier tube (MCP-PMT). Fluorescence decay curves were collected from samples in 0.5 cm pathlength quartz cuvettes at 90 degrees. The collection path included a Glan-Thompson polarizer set at 54.7° relative to the excitation polarization and an OG11 longpass filter placed before the MCP-PMT.

Figure 15:
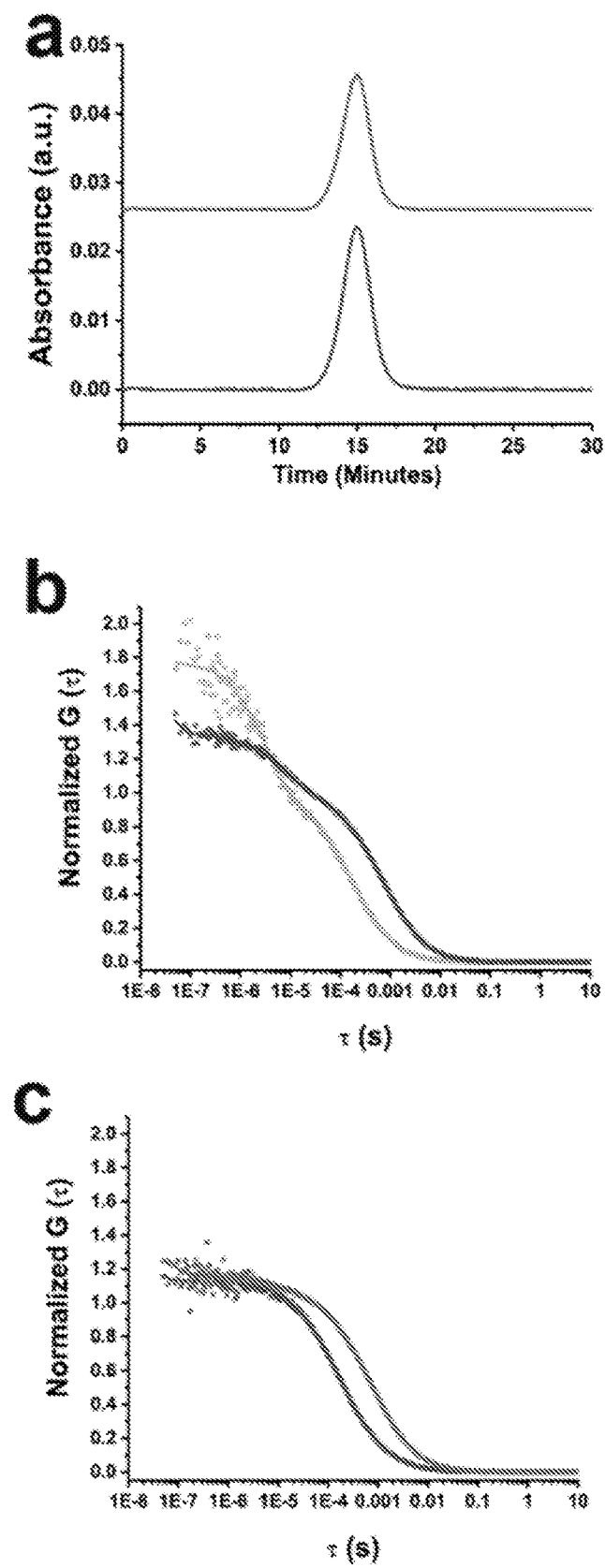
FIG. 15 shows standard particle characterization and ferroptosis comparison. a) Analytical GPC chromatogram of Cy5-C' dots (bottom) and ATTO647N-C' dots (top). b) FCS correlation curves of Cy5 dye (light) and Cy5-C' dots (dark). c) FCS correlation curves of ATTO647N (light) and ATTO647N-C' dots (dark). d-e) TEM images of Cy5-C' dots (d) and ATTO647N-C' dots (e). f) Percentage of inhibited cell growth as a function of concentration of Cy5 (dark) and ATTO647N (light) based C' dots.
Figure 15:
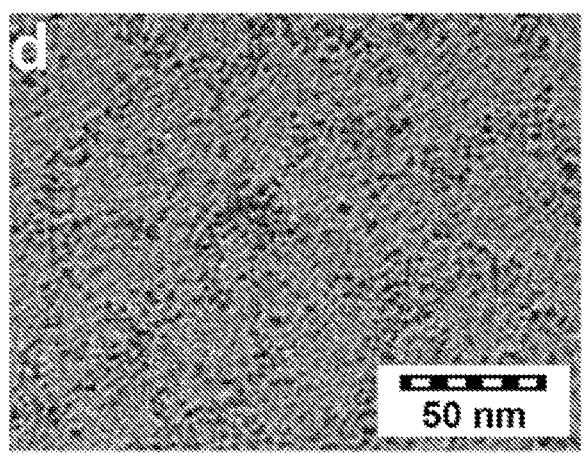
Figure 15:
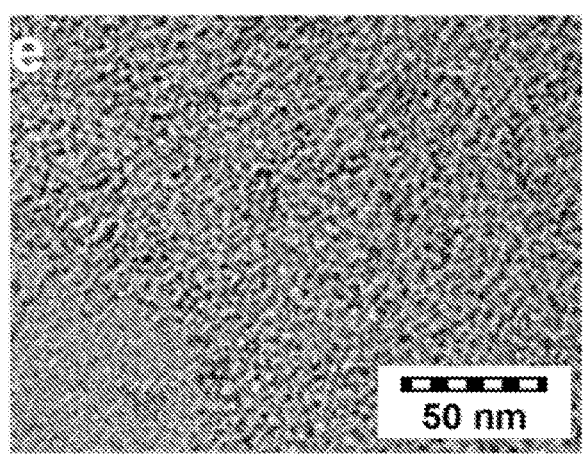
Figure 15:
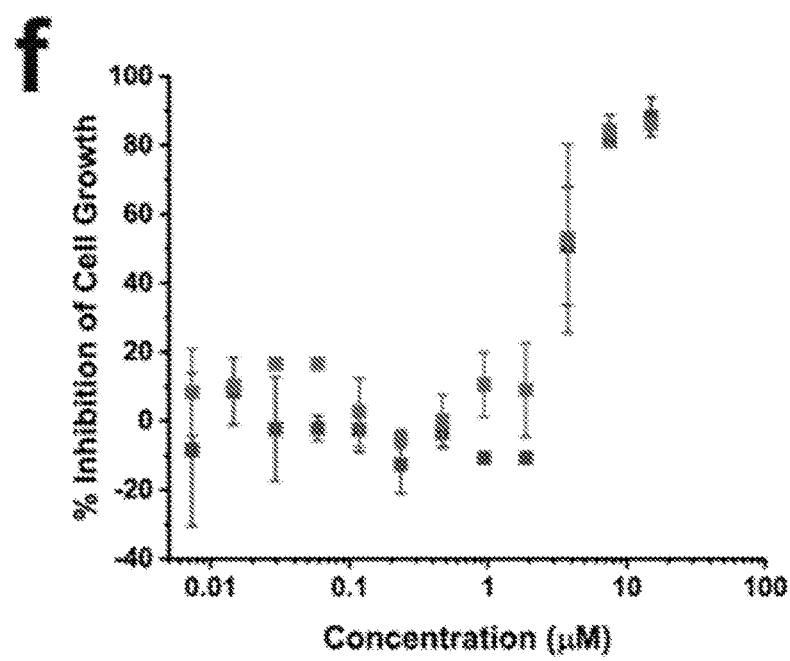

Results and Discussion. After C' dot syntheses with Cy5 and ATTO647N dye, respectively, particle batches were submitted to standard purification and characterization procedures established in previous studies including gel permeation chromatography (GPC) for purification and characterization, as well as fluorescence correlation spectroscopy (FCS) and transmission electron microscopy (TEM) for characterization. FIG. 15 shows representative data sets from these techniques applied to Cy5-based and ATTO647N-based C' dots purified by analytical GPC to remove unreacted species and particle aggregates (see Methods section). FIG. 15a depicts analytical GPC chromatograms for purified Cy5-C' dots (blue) and ATTO647N-C' dots (red) (see above) suggesting that both particles have similar size. Both chromatograms are symmetric and show a Gaussian distribution of particle sizes, suggesting narrow size distributions. This was confirmed by FCS shown in FIG. 15b,c, which compares results for free dye and dots for Cy5-(b) and ATTO647-(c) based particles. The results of ATTO647N free dye and particles (FIG. 15c) mainly differ in the longest correlation time, reflecting the increase in size when moving from free dye to particle. In contrast, in the case of Cy5 there is a substantial difference also observed for short correlation times. The latter reflects the difference in the reduced amount of trans-cis isomerization that takes place in the particle relative to the free dye. Both effects can be quantified through fits of the data sets (see Methods section for details). According to these correlation curve fits, the corresponding hydrodynamic diameters of free dyes and dots are: $d_{Cy5}$=1.35±0.02 nm, $d_{Cy5-C'dots}$=5.46±0.21 nm, $d_{ATTO647N}$=1.70±0.27 nm, $d_{ATTO647N-C'dots}$=5.95±0.18 nm, thereby corroborating the GPC results on similar sized dots. FIGS. 15d and e depict TEM images of Cy5- and ATTO647N-based C' dots. Even though TEM is not well suited to characterize such small silica nanoparticles, as silica is susceptible to electron beam damage, the images demonstrate the homogeneous particle size distribution of the silica cores, with diameters around 3.5 nm. Finally, Cy5- and ATTO647N-based C' dots to induce ferroptosis, a cell death program recently discovered to be activated by microporous and ultrasmall C' dots in various cancer cell lines under nutrient deprived conditions was tested. FIG. 15f shows results of these experiments expressed as cell growth as a function of the concentration of Cy5- and ATTO647N-C' dots added to MDA-MB-231 breast cancer cells. For both particles, similar concentration dependent cell behavior was observed suggesting cells underwent massive ferroptotic cell death when concentrations reached about 15 µM, consistent with results reported in an earlier study. All these results together suggested that aside from the difference in the covalently incorporated dye, i.e., Cy5 versus ATTO647N, both particle sets displayed similar behavior in our standard characterization experiments.

Figure 16:
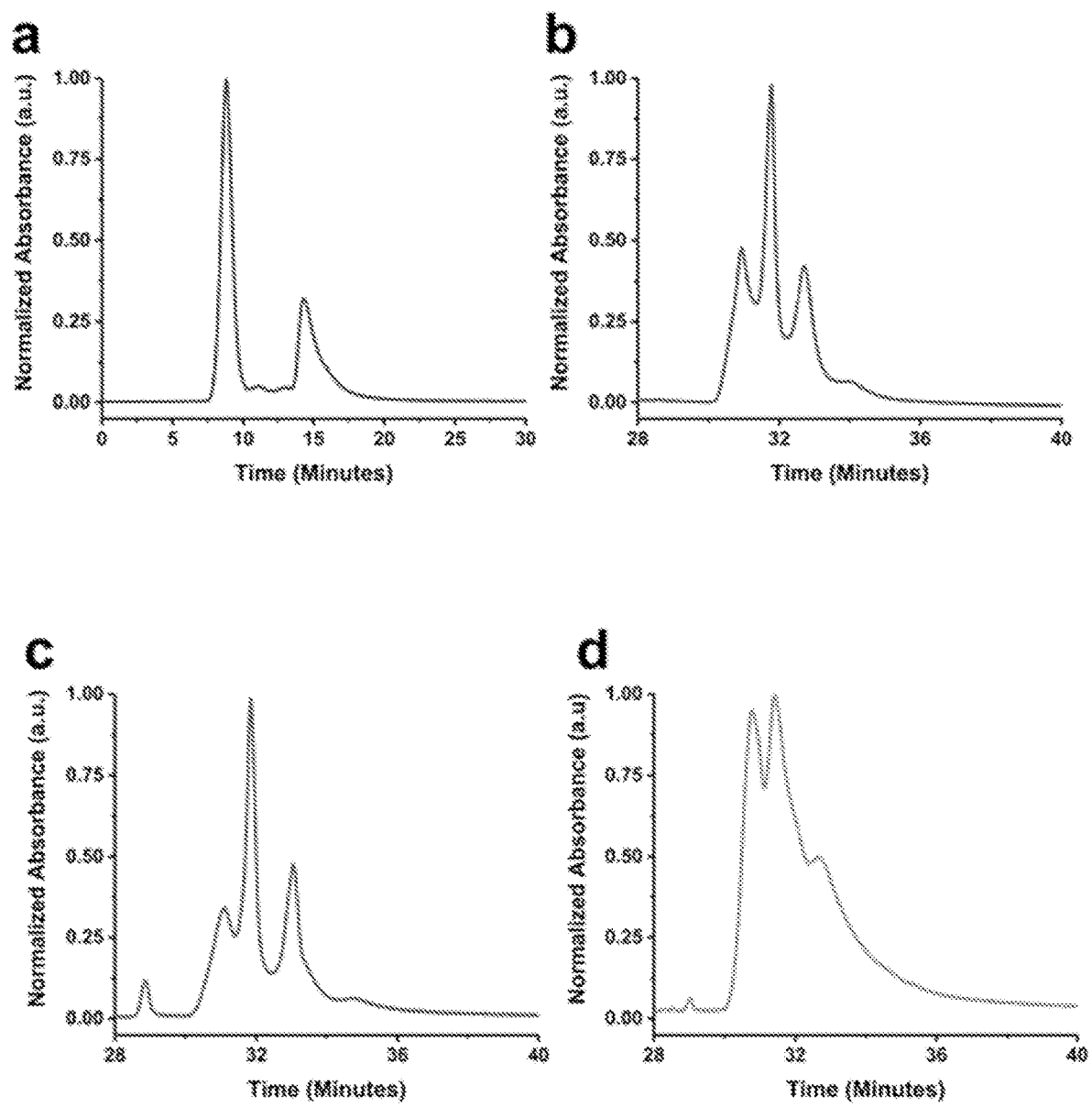
FIG. 16 shows chromatographic characterization of Cy5- and ATTO647N-based C' dots. Top row: results for Cy5 based C' dots; bottom row: results for Atto647N based C' dots. a and e) Size exclusion gel permeation chromatography (GPC) chromatograms of C' dot native synthesis solutions. b and f) High performance liquid chromatography (HPLC) chromatograms of GPC refined C' dots. c and g) HPLC chromatograms of C' dots after one year of storage. d and h) HPLC chromatograms of cRGD-C'dots after storage for several weeks.
Figure 16:
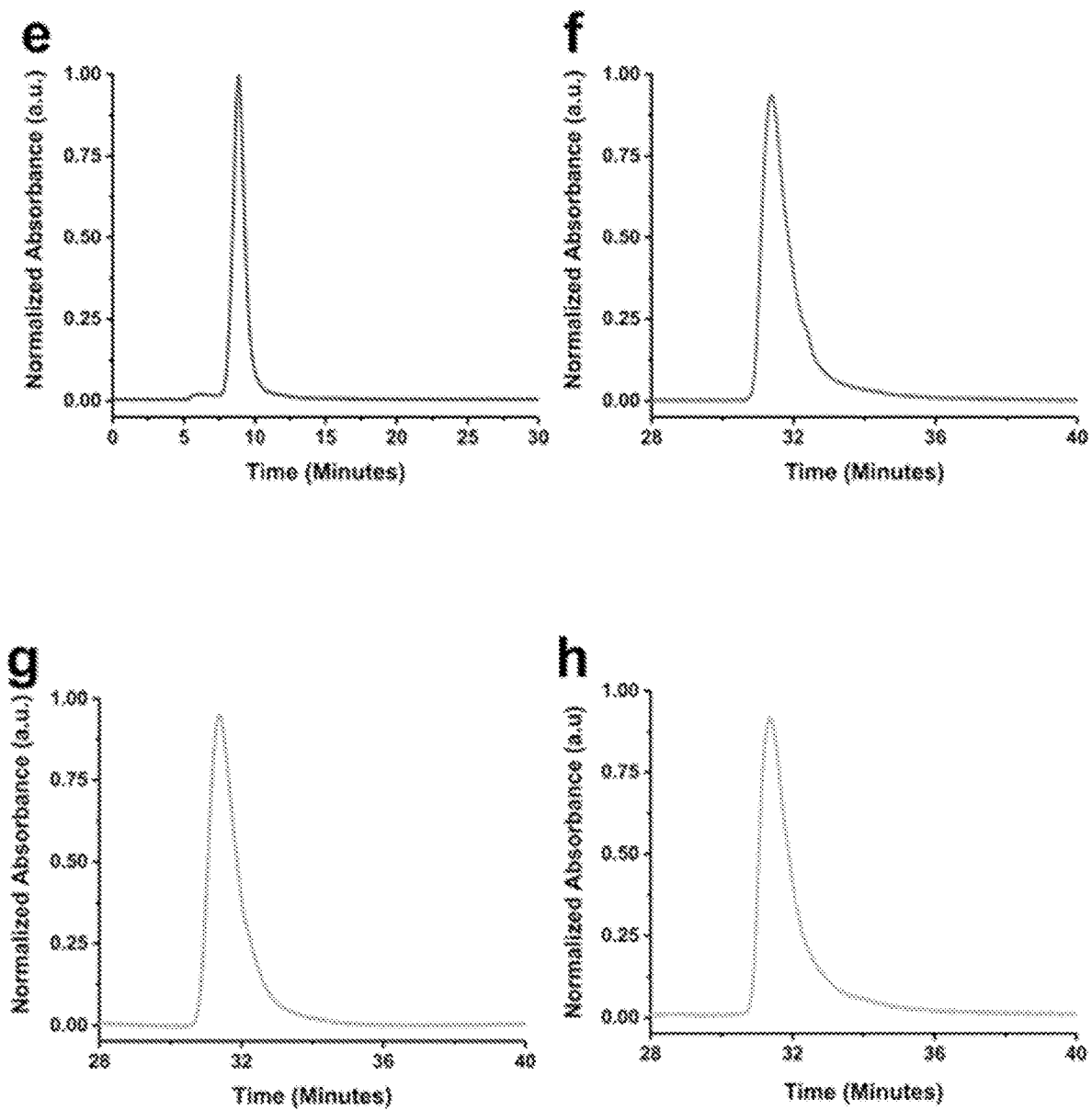

To further explore the effects of the different dye chemistries of Cy5 and ATTO647N on silica nanoparticle formation and architecture, high-resolution chromatography was used. FIGS. 16a and 16e show preparative size exclusion GPC chromatograms as observed using the 647 nm detection channel for native C' dot synthesis solutions, i.e., for solutions right out of the synthesis reactor without any prior purification steps. From these chromatograms we see that for Cy5-C' dots, in addition to the main particle peak located around 9 minutes there also is a substantial free dye peak at longer elution times of around 15 minutes (63%/37% for particle/free dye). In contrast, besides the main particle peak around 9 minutes the chromatogram for ATTO647N-C' dot only shows a small shoulder around 6-7 minutes (~9%) appearing just before the main particle peak corresponding to larger aggregates. These results suggest that the positively charged ATTO647N dye has a higher affinity to the negatively charged and growing silica particle during synthesis as compared to the negatively charged Cy5 dye.

FIGS. 16b and 16f compare HPLC chromatograms for GPC purified Cy5-based and ATTO647N-based C' dots, respectively. It has been shown in previous studies that the negative charge of the Cy5 dye produces particles with 0, 1, 2, and 3 dyes sitting on the silica core surface of the particles, respectively, resulting in the four HPLC peaks in FIG. 16b (3 dominant peaks and 1 small peak). In contrast, the same study demonstrated that ATTO647N produces particles with dyes primarily encapsulated in the silica core of the silica-PEG core-shell nanoparticles, resulting in essentially a single peak in the HPLC chromatogram in FIG. 16f. This increase in surface chemical homogeneity of ATTO647N-over Cy5-based C' dots benefits the shelf life of C' dots. To that end FIGS. 16c and 16g show HPLC chromatograms of Cy5- and ATTO647N-based C' dots after one year of cold (at 4° C.) dark storage. While the ATTO647N-based particle chromatogram in FIG. 16g is essentially unchanged over that of a freshly prepared sample in FIG. 16f, the chromatogram of one year old Cy5-C' dots in FIG. 16c exhibits a free dye peak located around 29 minutes not present in the freshly prepared sample (FIG. 16b) and suggesting dye leaching. Finally, the superior degree of dye encapsulation of the ATTO647N dye and concomitant surface-chemical homogeneity also influences the synthesis of targeting peptide bearing C' dots. To that end, FIGS. 16d and 16h compare HPLC chromatograms of Cy5- and ATTO647N-based C' dots functionalized with c(RGDyC) peptides targeting integrins overexpressed on several tumors (15 c(RGDyC) for Cy5-based C' dots and 12 for ATTO647N-based C' dots, see supporting information). Even with multiple c(RGDyC) copies attached to the chain end of some of the PEG chains, ATTO647N-based C' dots show only a single peak in the HPLC chromatogram. In contrast, in the corresponding chromatogram of c(RGDyC) functionalized Cy5-based C' dots the 3 dominant peaks of the unfunctionalized dots can still be identified (compare FIGS. 16b and d), but now features are broadened, suggesting substantial heterogeneity in the surface-chemical properties.

Figure 14:
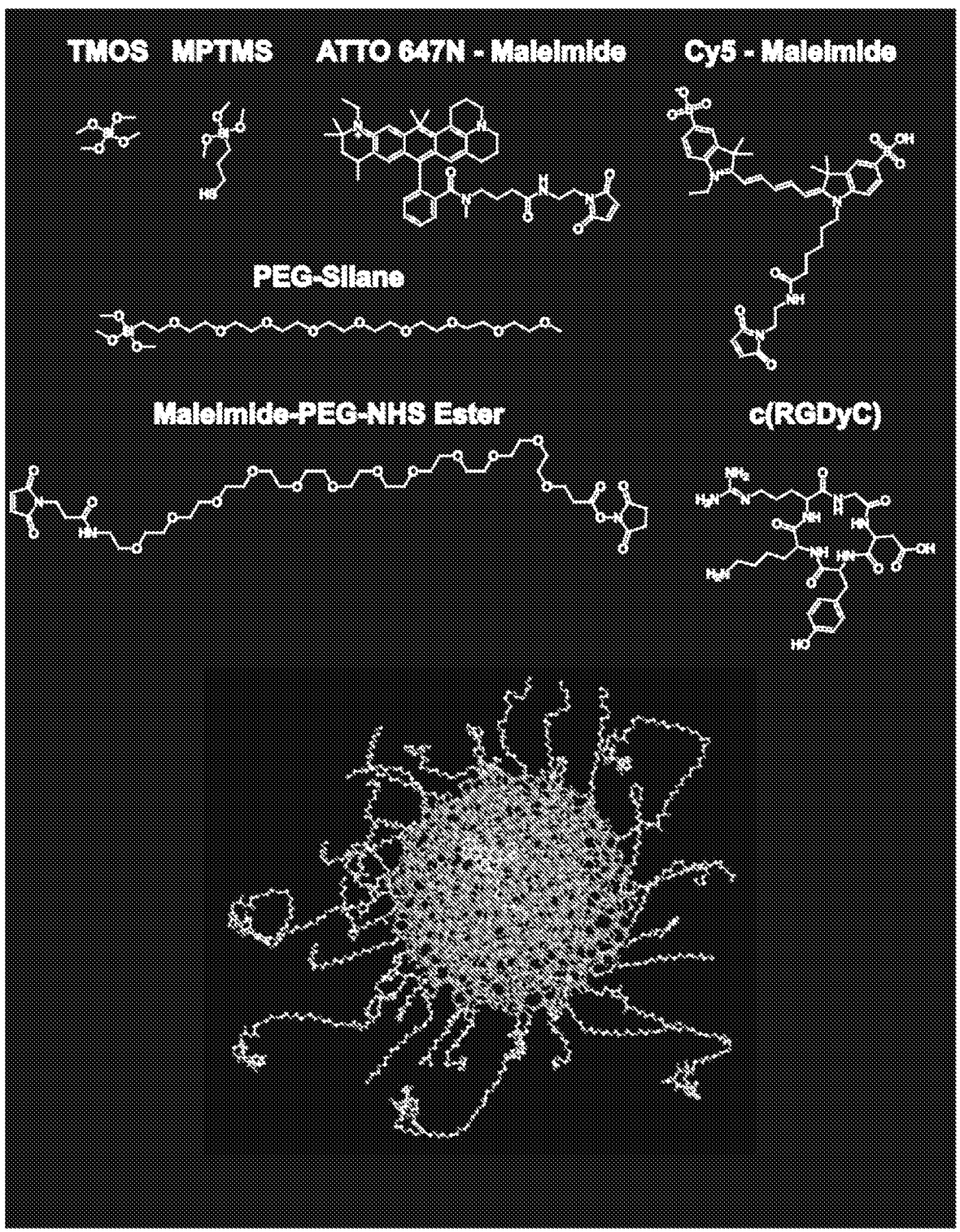
FIG. 14 shows particle rendering and materials. Chemical structures and particle illustration showing the dye encapsulation of ATTO647N, PEGylated exterior, and functionalized with integrin targeting peptide c(RGDyC). The inset shows the encapsulation of the ATTO647N dye.
Figure 17:
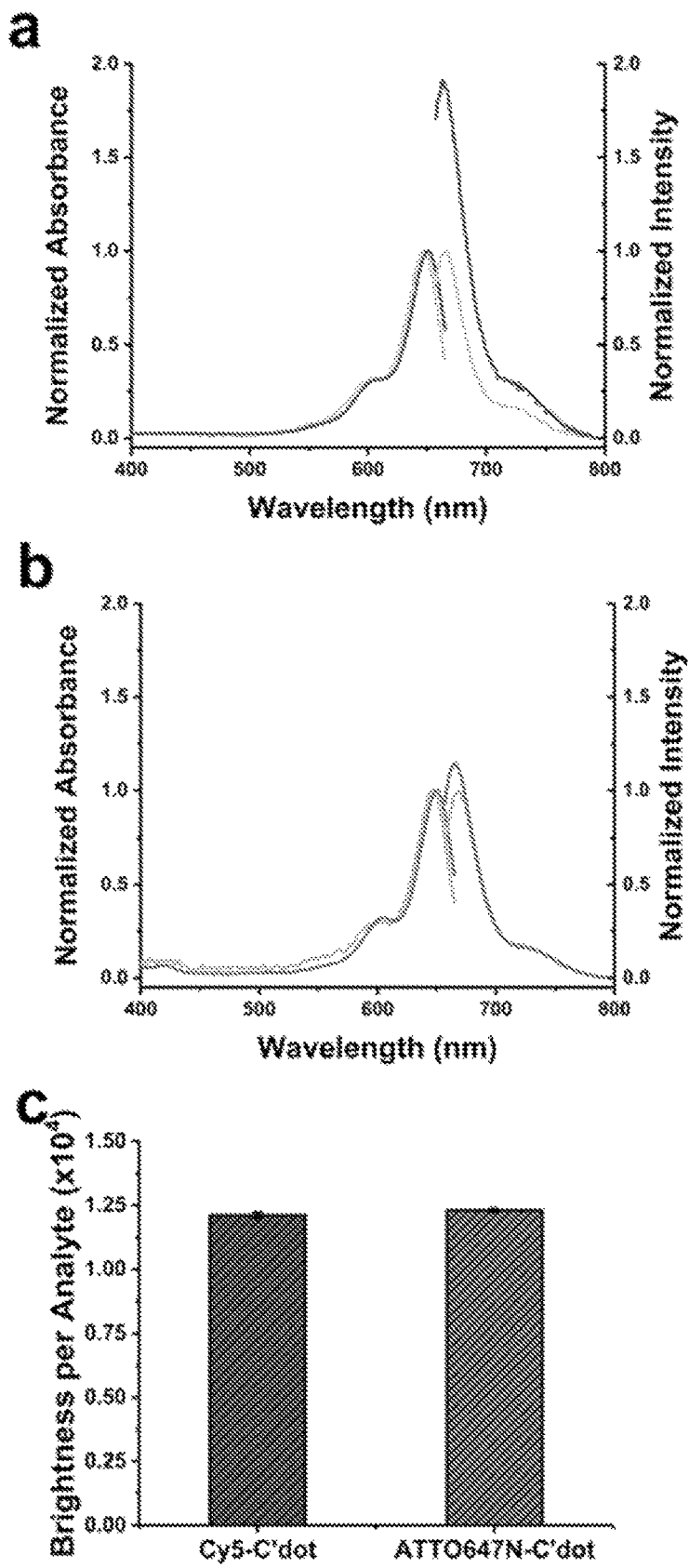
FIG. 17 photo-physical characterization of Cy5- and ATTO647N-based C' dots. a) Comparison of absorption matched absorbance and fluorescence spectra of Cy5 dye (light) and Cy5-based C' dots (dark) in water. b) Comparison of absorption matched absorbance and fluorescence of ATTO647N dye (light) and ATTO647N-based C' dots (dark). c) Comparison of FCS derived brightness of Cy5-based and ATTO647N-based C' dots. d) Comparison of Cy5-based (dark) and ATTO647N-based (light) C' dot photobleaching. e) Comparison of quantum yield measurements for Cy5-based (2) and ATTO647N-based (1) C' dots as compared to free Cy5 dye (3). f) Photon lifetime measurements for Cy5-based (dark) and ATTO647N-based (light) C' dots.
Figure 17:
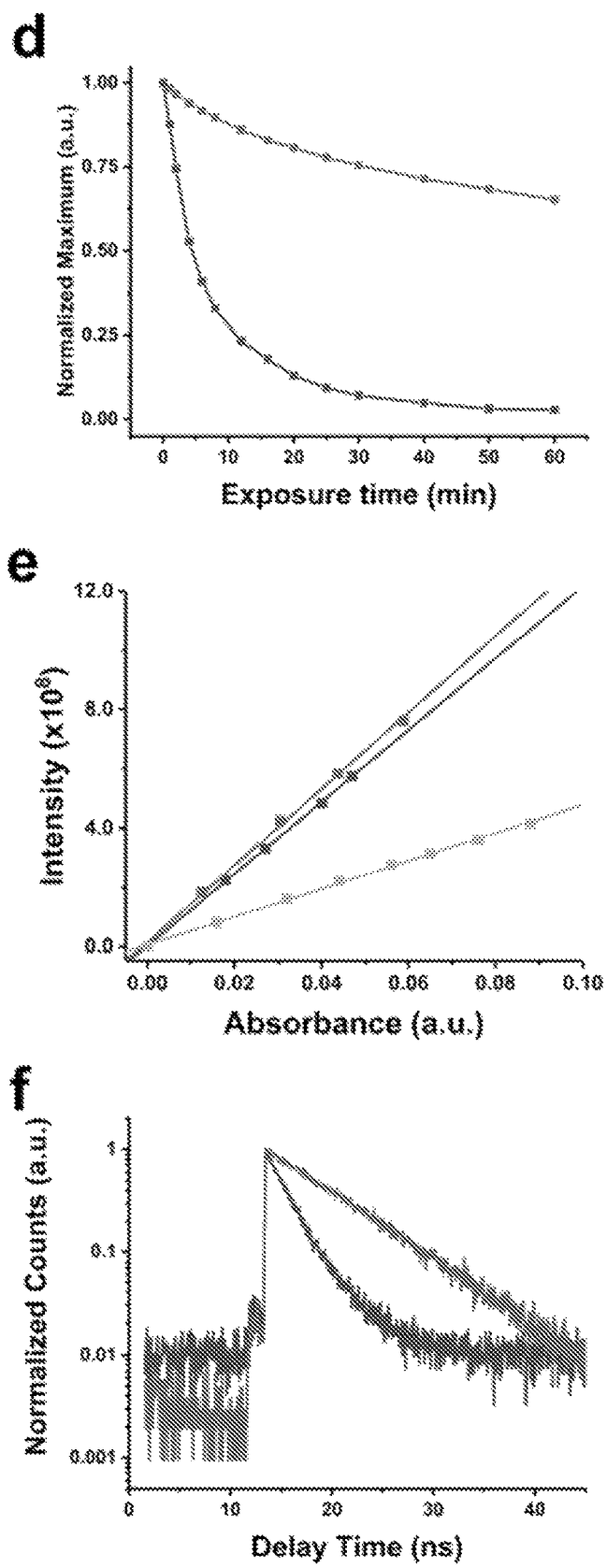
Figure 18:
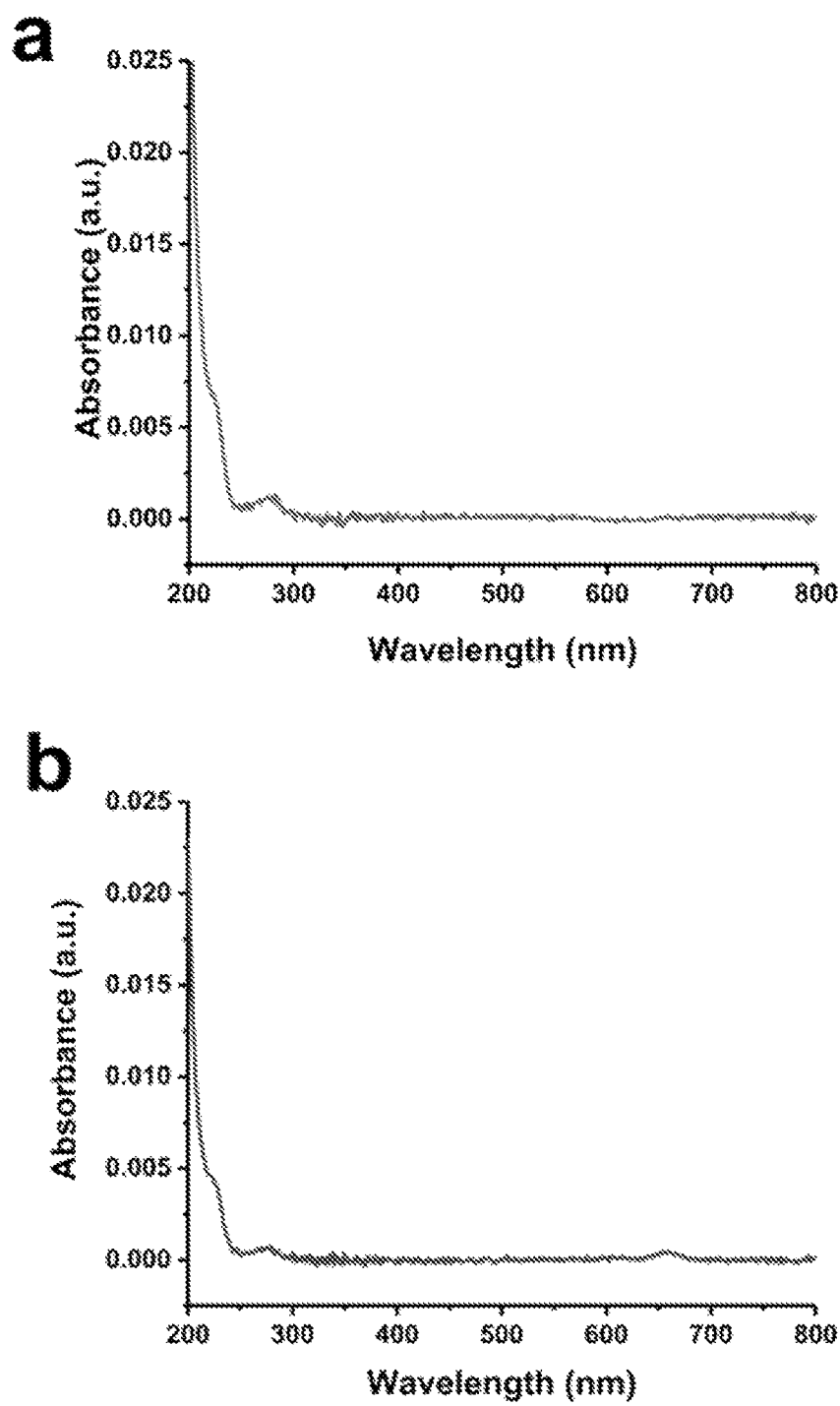
FIG. 18 shows absorbance spectra of RGD. Absorbance spectra of RGD attached to a) ATTO647N-C' dot and b) Cy5-C' dots.
Figure 19:
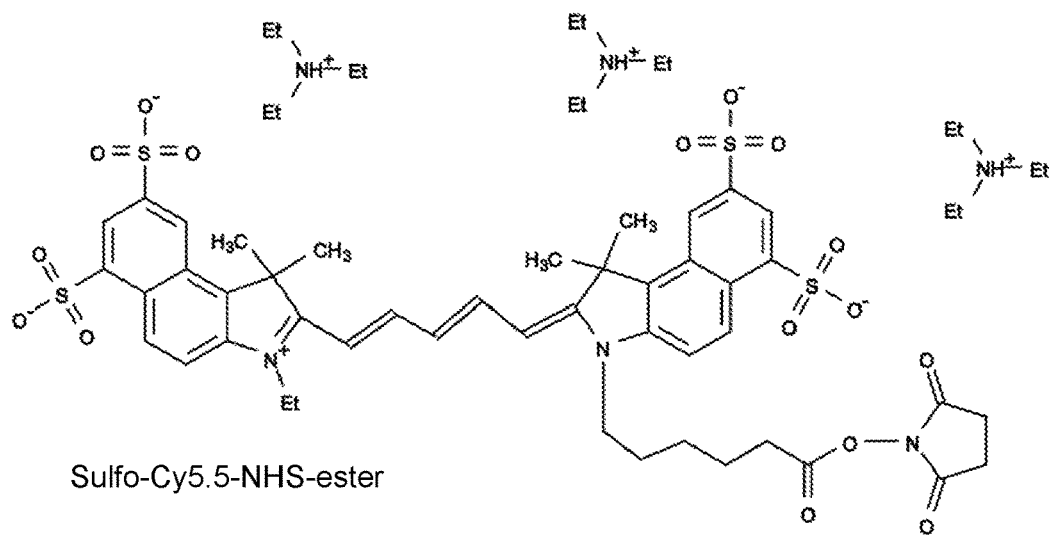
FIG. 19 shows various dyes molecules suitable for conjugation to the inorganic nanoparticles of the present disclosure. Other suitable dyes are known in the art.
Figure 19:
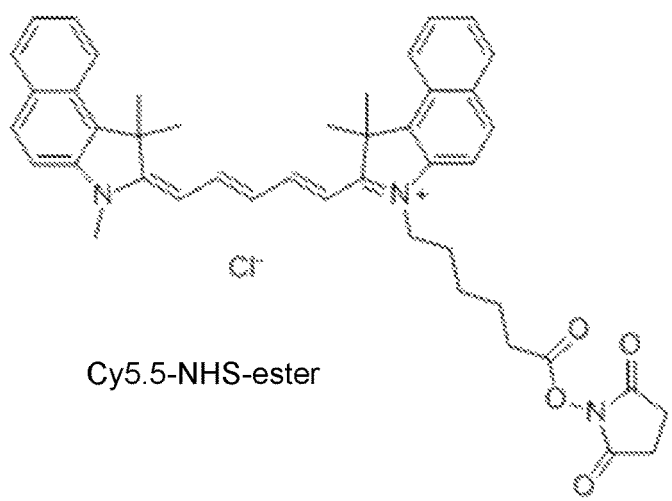
Figure 19:
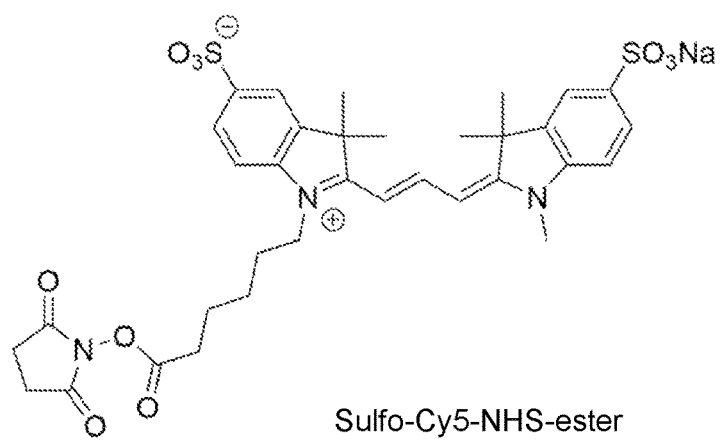
Figure 19:
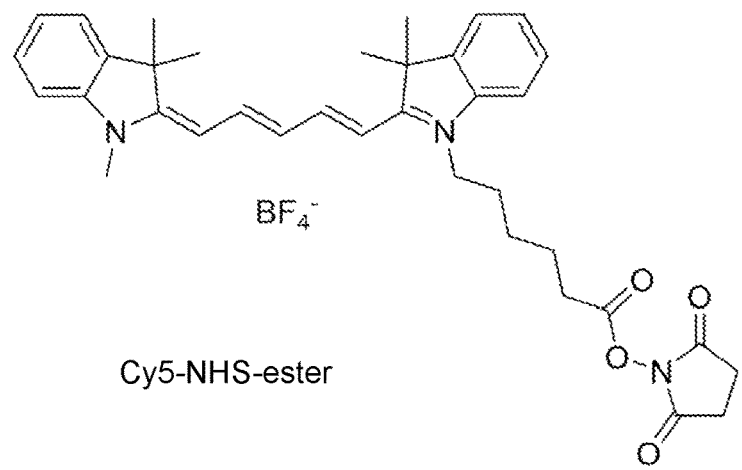
Figure 19:
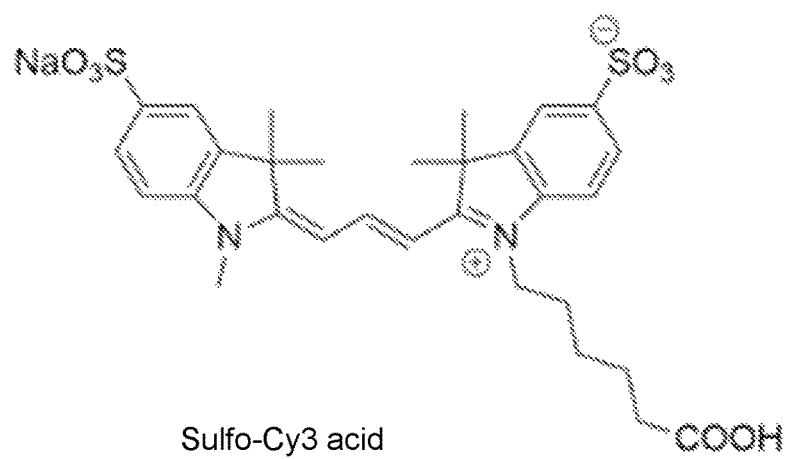
Figure 19:
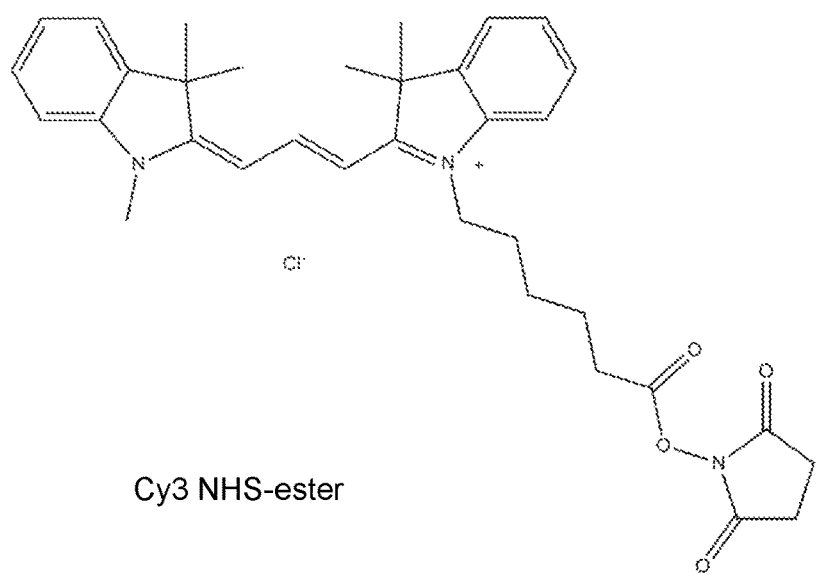
Figure 19:
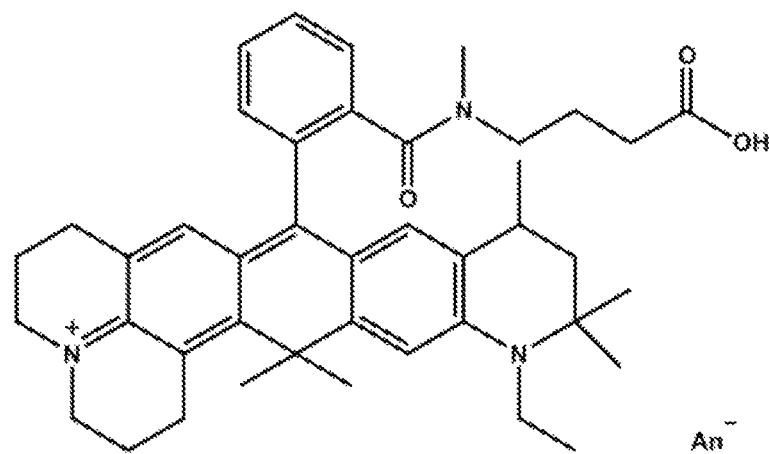
Figure 19:
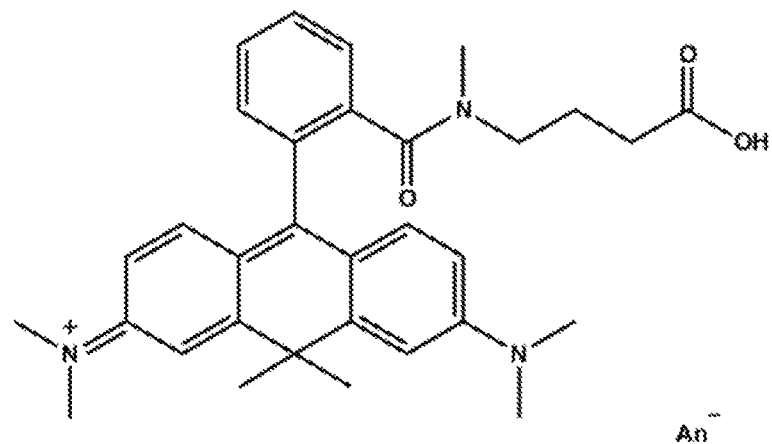
Figure 19:
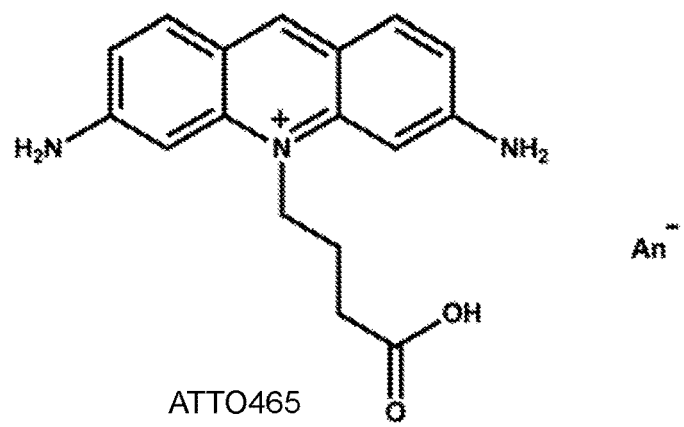
Figure 19:
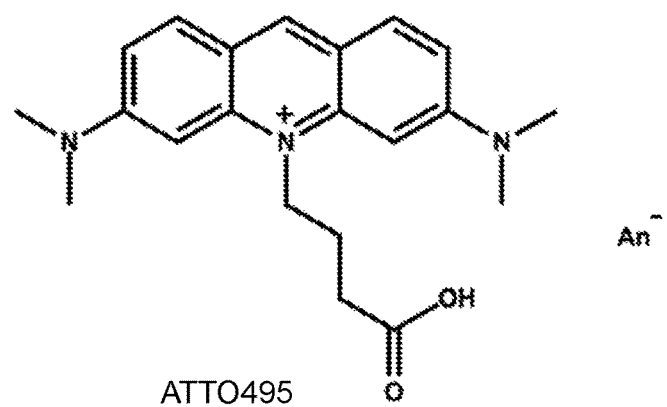
Figure 19:
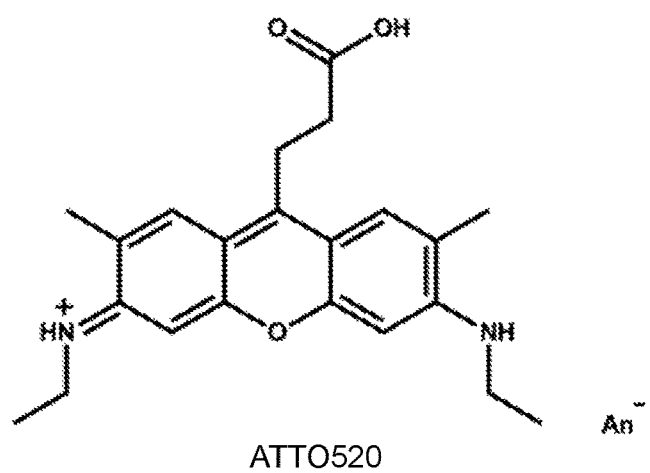
Figure 19:
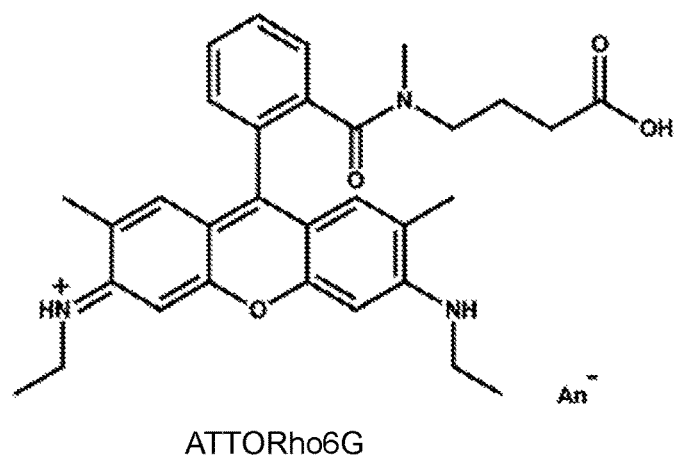
Figure 19:
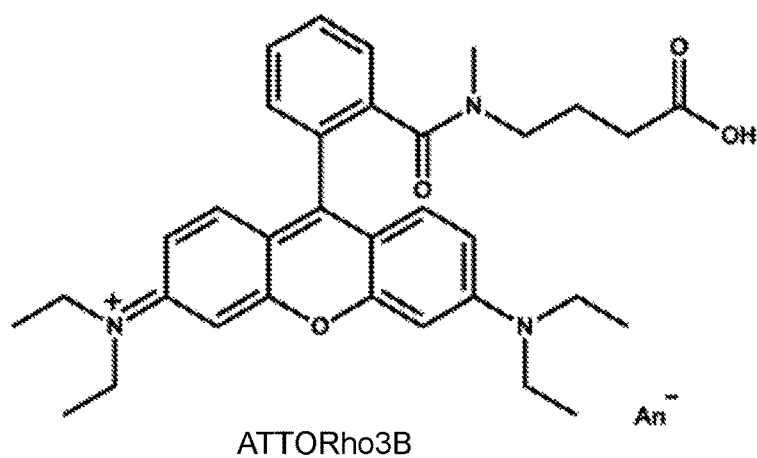
Figure 19:
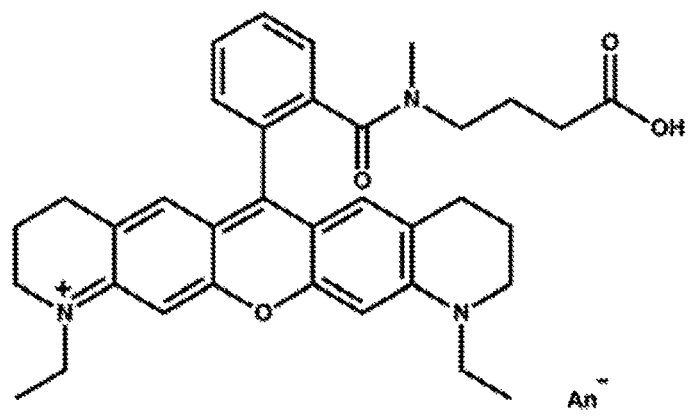
Figure 19:
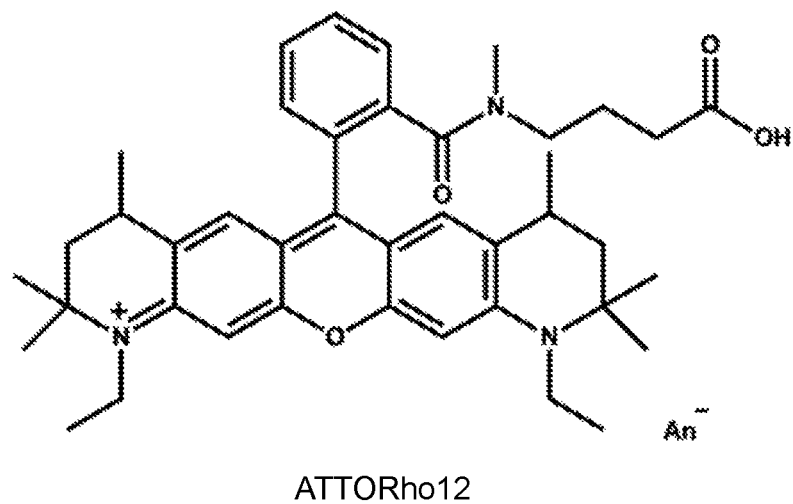
Figure 19:
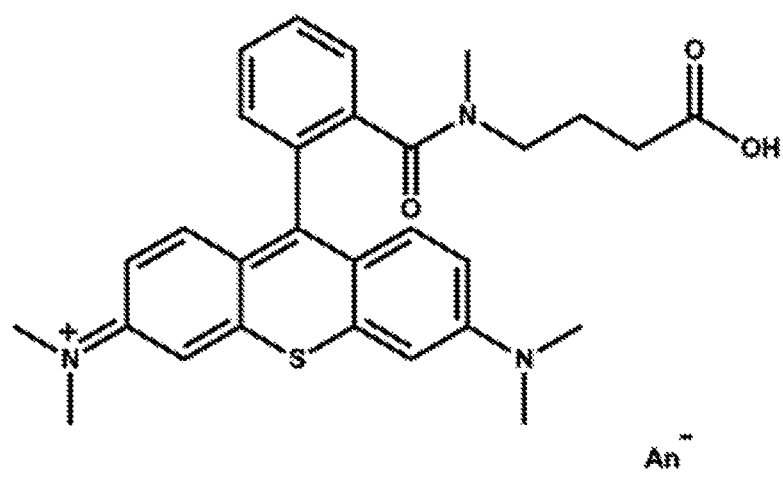
Figure 19:
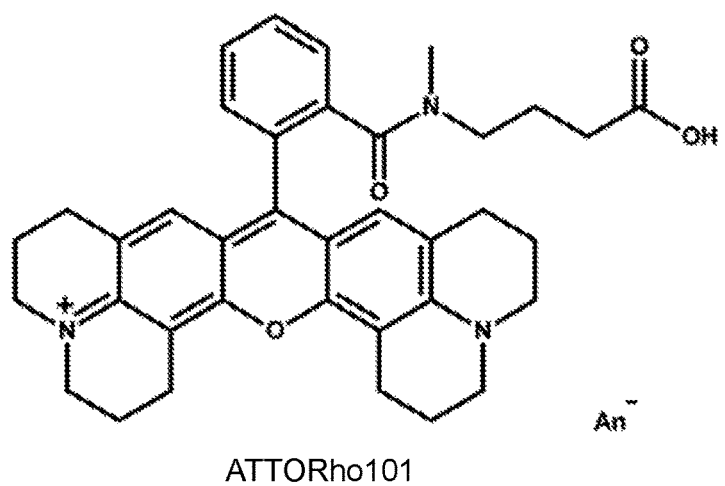
Figure 19:
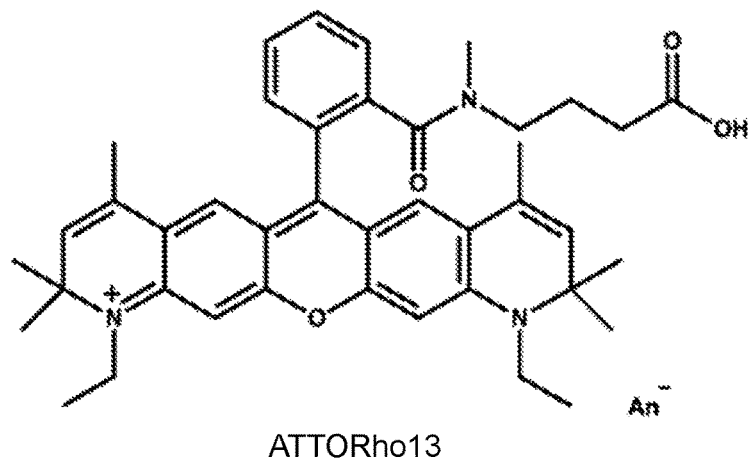
Figure 19:
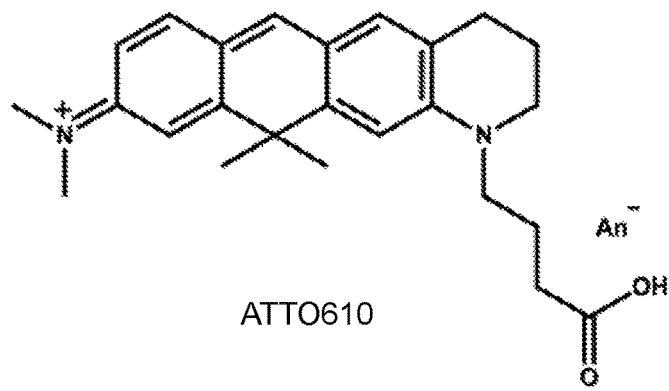
Figure 19:
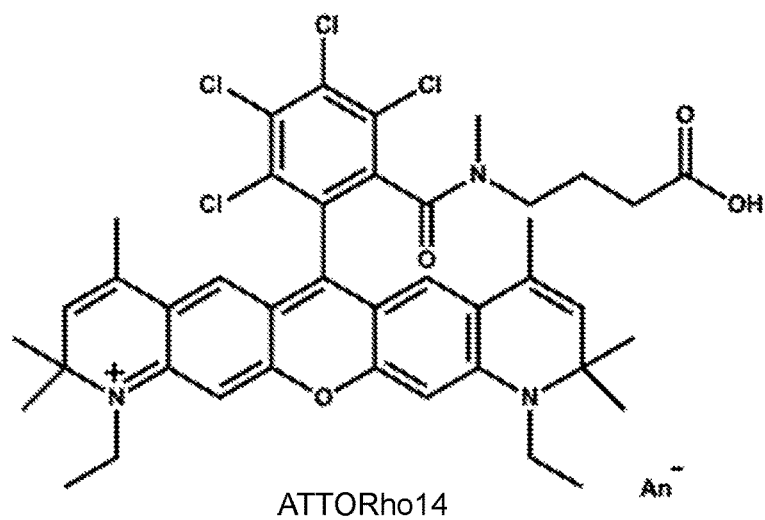
Figure 19:
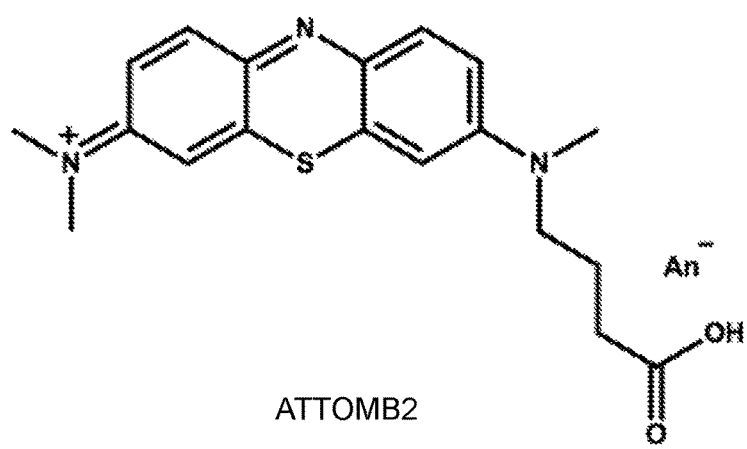
Figure 19:
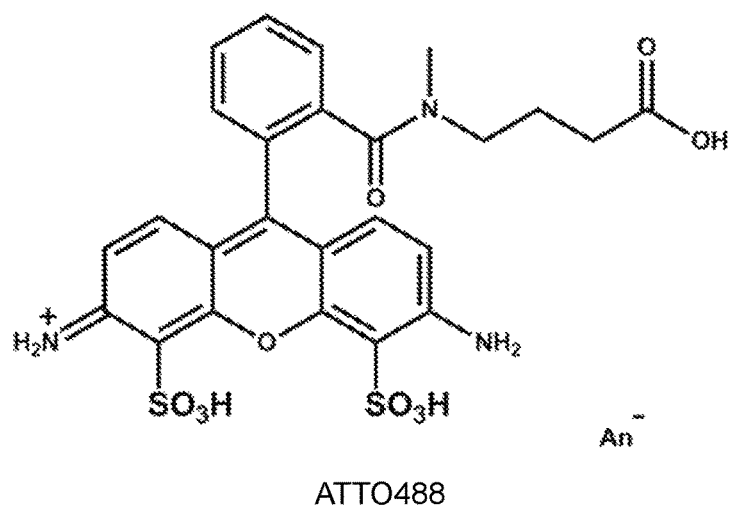
Figure 19:
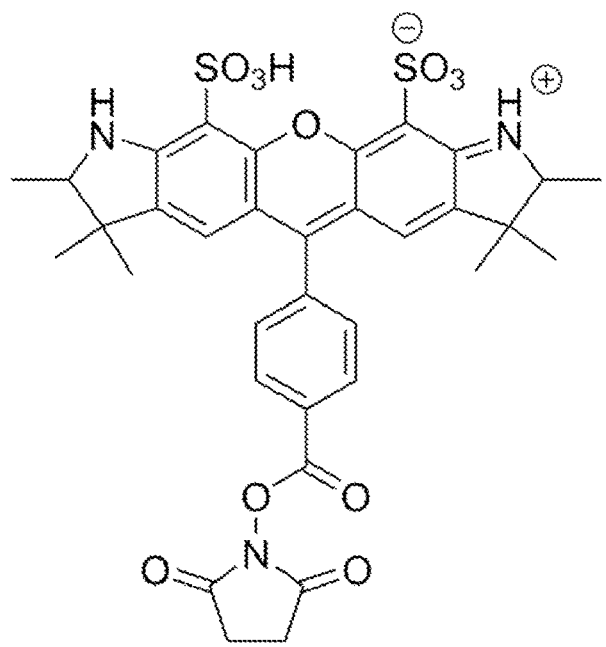
Figure 19:
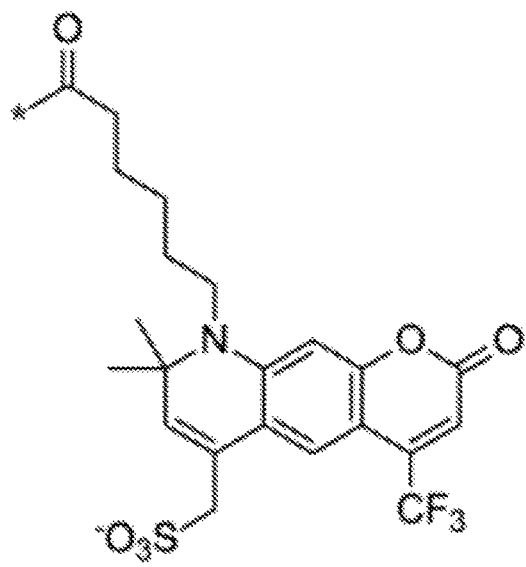
Figure 19:
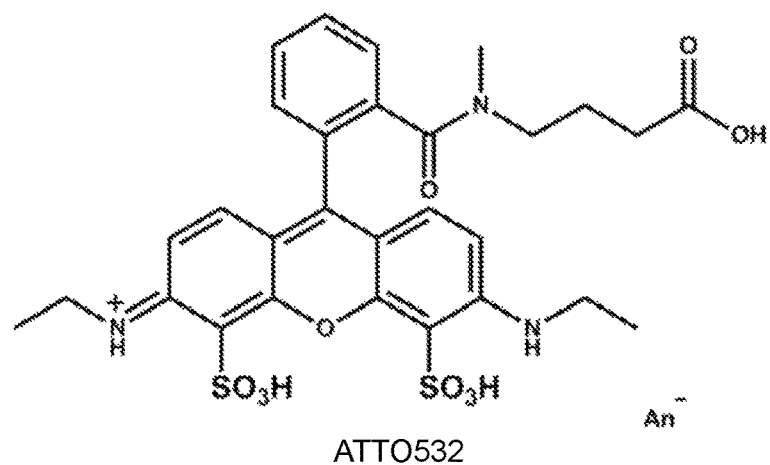
Figure 19:
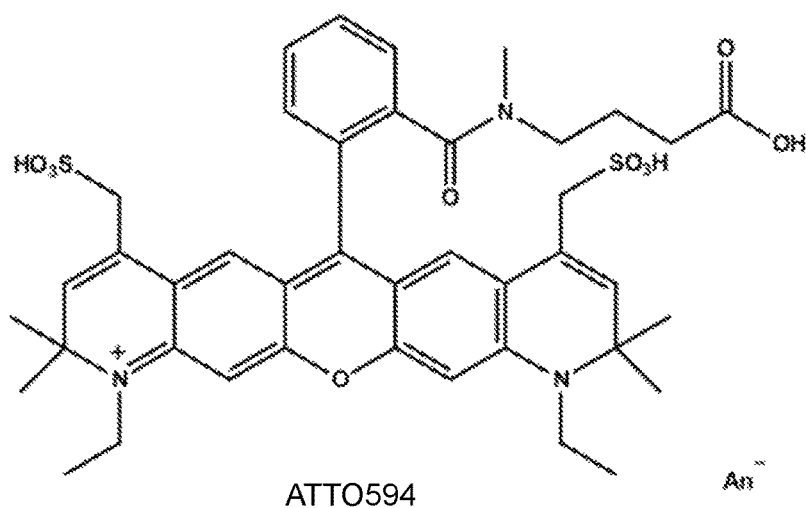
Figure 19:
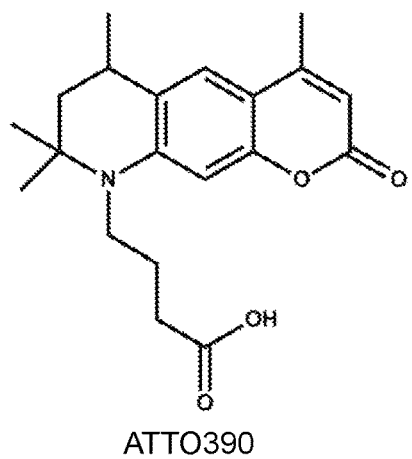
Figure 19:
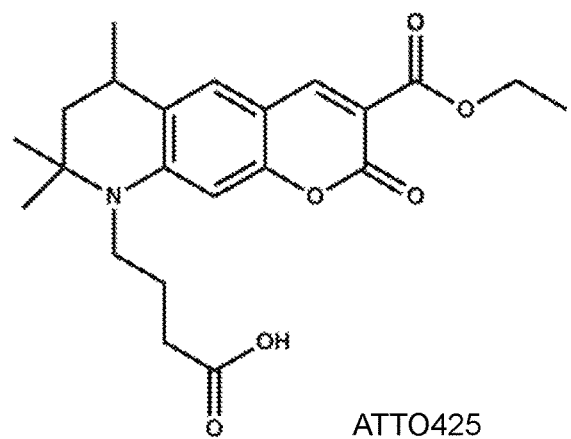
Figure 19:
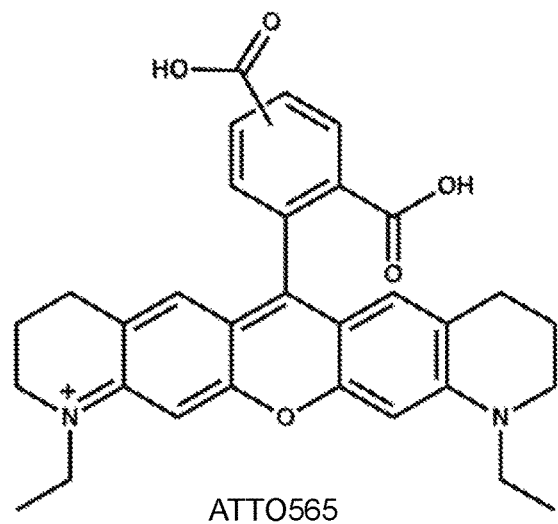
Figure 19:
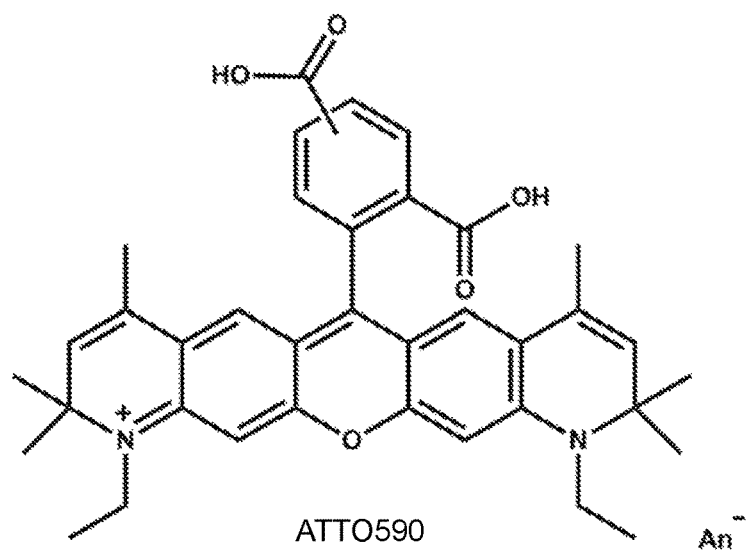
Figure 19:
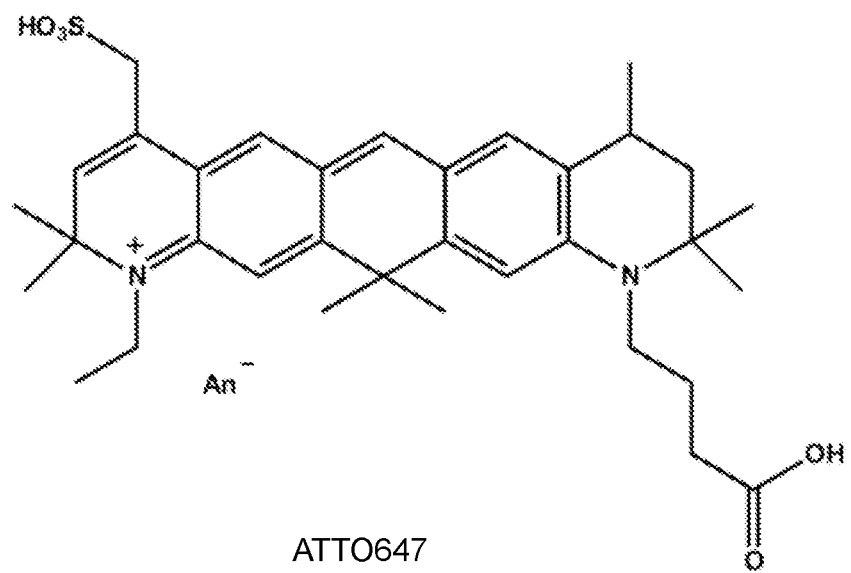
Figure 19:
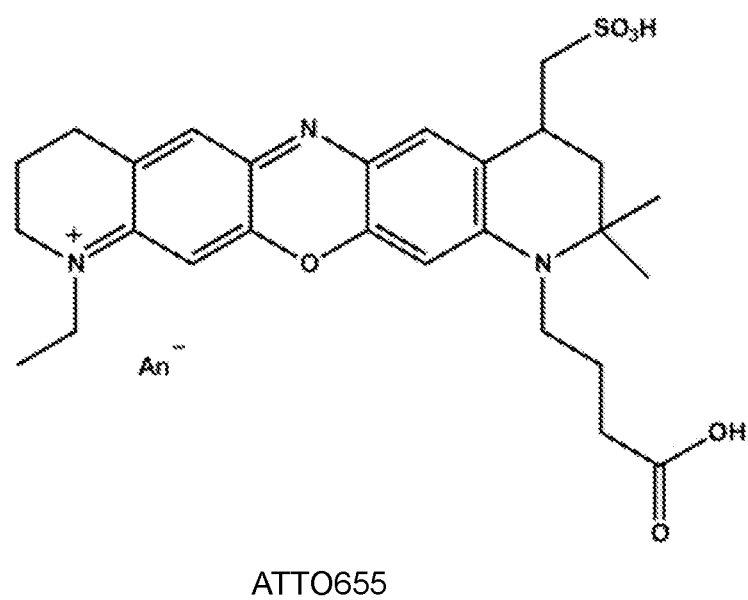
Figure 19:
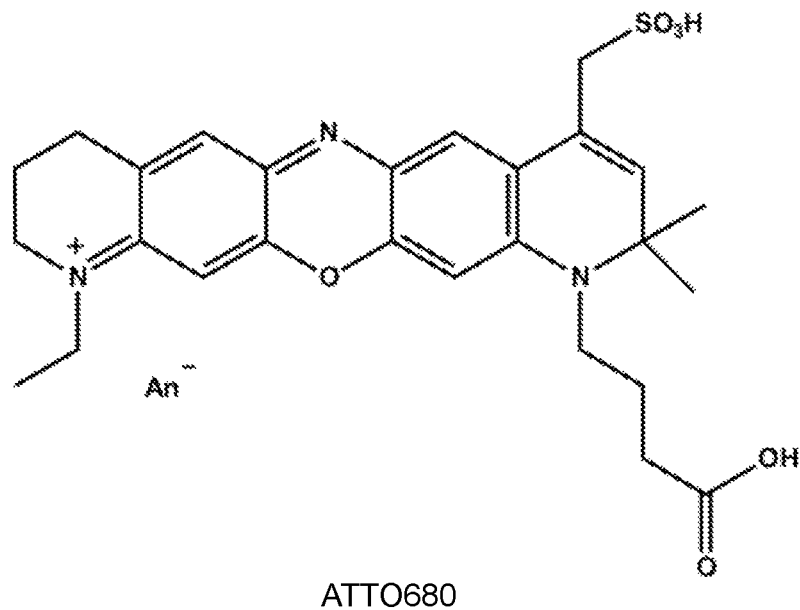
Figure 19:
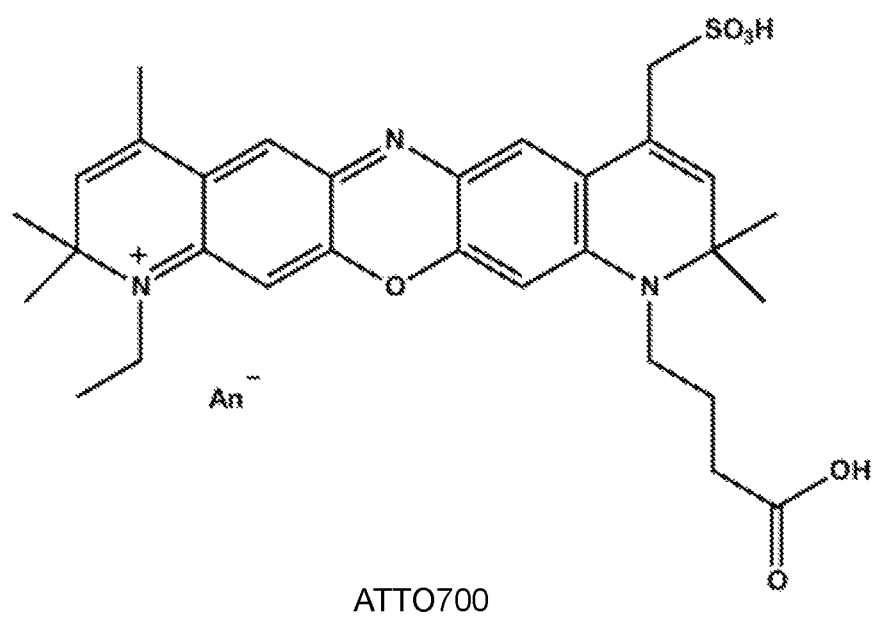

Encapsulation of ATTO647N not only clearly changes the surface-chemical properties of the resulting silica nanoparticles relative to Cy5-based C' dots, but the two sets of particles also show differences in their photo-physical properties. While absorption and emission spectra of absorption-matched samples of dye and particles for Cy5 and ATTO647N in FIGS. 17a and b suggest a larger increase in the per-dye brightness for Cy5 upon encapsulation, the per particle brightness derived from FCS photon counts of the two particles is almost identical (FIG. 17c). The main benefit working with ATTO647N instead of Cy5 is its enhanced photo-stability. FIG. 17d compares the photobleaching of the two particles demonstrating that ATTO647N is far superior with respect to its photo-stability than Cy5. These data suggest that ATTO647N-based particles can be tracked with fluorescence imaging much longer than the Cy5-C' dots before photobleaching occurs. As shown in FIG. 17e, both particles have a similar quantum yield: 75% versus 77% for Cy5 versus ATTO647N encapsulating dots (using Cy5 as a reference for both). Finally, FIG. 17f compares time-resolved fluorescence measurements of Cy5- and ATTO647N-based particles. Lifetimes extracted from single exponential fits to these decay curves result in 6.2 ns for ATTO647N-C'dot and 2.3 ns for Cy5-C'dots. Particle brightness as derived from the FCS correlation curves as shown in FIG. 17c and are similar. Non-radiative and radiative rate constants ($k_{nr}$ and $k_r$) can be extrapolated from quantum yield and fluorescence lifetime measurements, providing the following results: $k_r$ (Cy5-C'dot)=0.32, $k_{nr}$(Cy5-C'dot)=0.11, $k_r$ (ATTO647N-C' dot)=0.11, and $k_{nr}$ (ATTO647N-C' dot)=0.04. The more compact, rigid ring framework of ATTO647N as compared to the Cy5 structure with long and relatively "floppy" methine bridge between the two condensed ring systems (FIG. 14) is likely responsible for the lower non-radiative rate of ATTO647N as compared to Cy5 as well as its increased photostability.

In conclusion, the encapsulation of ATTO647 rather than Cy5 into ultrasmall core-shell silica nanoparticles was shown to lead to superior surface-chemical homogeneity, stability against chemical degradation, and photobleaching stability, while other desirable characteristics including hydrodynamic size, absorption/emission characteristics in the NIR, particle brightness, and ability to induce ferroptosis in nutrient deprived tumor cells remain similar. These findings render these third generation ATTO647N based C' dots a promising new particle platform for applications including bioimaging and nanomedicine.

Example 4

The present example provides description of characterization of inorganic nanoparticles of the present disclosure.

C' dots were analyzed using high performance liquid chromatography, a technique used in small molecule and macromolecular characterization, but new for nanoparticle characterization. HPLC may be used to separate out particles with different surface chemical characteristics based on the fact that the particles coming out of a synthesis batch are not compositionally homogeneous, but heterogeneous.

In various examples, in analysis of C', there are several peaks in the HPLC chromatograms. These peaks are due to different composition nanoparticles with either 0, 1, 2, or 3 Cy5 dyes on the silica care surface. Since these dyes are relatively hydrophobic, they shift the HPLC peaks to the right: the more dyes are on the surface, the more the HPLC chromatogram is shifted to the right.

Furthermore, these batch compositions are sensitive to the net dye charge. Moving from Cy5 with negative net charge to Atto647N with positive net charge, we change the composition of the particles from heterogeneous, multi-peak, to a single peak in the chromatogram, suggesting full incorporation of the dyes in all particles of the synthesis batch. This can also be extended to other positive net charge dyes.

These heterogeneities have consequences in the particle properties. For example, if the dyes are on the surface, like for Cy5, HPLC chromatograms taken over several months clearly show that these dyes get knocked off the surface. In contrast, when the dyes are fully encapsulated like for Atto647N, they do not leach out of the particles, according to HPLC chromatograms taken over several months.

As a result of this improved characterization methodology, we can elucidate key synthesis parameters, like the charge of the dye, that control compositional heterogeneity. This is an important finding for clinical trial studies where particles are injected into patients. If the particles are heterogeneous, for example, they may shed substantial amounts of dye (vide supra) which may cause side effects.

The techniques disclosed herein provide an aqueous synthesis approach to ultrasmall functional PEGylated fluorescent silica nanoparticles with improved control in multiple aspects, including particle size, particle size distribution, fluorescence wavelength, fluorescence brightness, compositions, particle PEGylation, particle surface functionalization, synthesis yield, product purity and manufacture reliability. The systematic and precise control covering all these aspects in a single organic-inorganic hybrid nanomaterials synthesis system has never been achieved before, preventing the safe translation of organic-inorganic hybrid nanomaterials from the laboratory to the clinic. Therefore, the techniques disclosed herein provide access to well-defined and systematically highly tunable silica-based nanomaterials that show significant potential in nanomedicine applications.

Although the present disclosure has been described with respect to one or more particular embodiments and/or examples, it will be understood that other embodiments and/or examples of the present disclosure may be made without departing from the scope of the present disclosure.

The invention claimed is:

1. A method of determining the location of one or more dye on and/or in an inorganic nanoparticle comprising a polyethylene glycol layer, comprising subjecting the inorganic nanoparticle or core-shell nanoparticle to high performance liquid chromatography (HPLC) analysis, wherein the method comprises the steps of:
   (a) depositing the inorganic nanoparticle in an HPLC column comprising an input in fluid communication with a stationary phase in fluid communication with an output in fluid communication with a detector;
   (b) passing a mobile phase through the HPLC column, such that the inorganic nanoparticle elutes from the column and enters the detector, such that the detector generates a signal, wherein the signal indicates the location of the one or more dye on and/or in the inorganic nanoparticle; and
   (c) analyzing the signal to determine the location of the one or more dye on and/or in the inorganic nanoparticle.

2. The method of claim 1, wherein the signal comprises an elution time and the elution time correlates to the location of the one or more dye on and/or in the inorganic nanoparticle.

3. The method of claim 1, wherein the HPLC column is a reverse phase HPLC (RP-HPLC) column.

4. The method of claim 1, wherein the mobile phase comprises water.

5. The method of claim 4, wherein the mobile phase further comprises acetonitrile, methanol, and/or isopropanol.

6. The method of claim 1, further comprising purifying the inorganic nanoparticle by gel permeation chromatography (GPC).

7. The method of claim 6, wherein the inorganic nanoparticle is purified by GPC before step (a).

8. The method of claim 1, wherein the stationary phase is a C4 to C8 functionalized silica.

9. The method of claim 1, wherein the mobile phase is passed through the column in a step-like gradient.

10. The method of claim 1, wherein the inorganic nanoparticle is a silica nanoparticle.

11. The method of claim 1, wherein the inorganic nanoparticle has an average diameter of 2 nm to 15 nm.

12. The method of claim 1, wherein the dye is disposed or partially disposed on the surface of the inorganic nanoparticle.

13. The method of claim 1, wherein the dye is encapsulated or partially encapsulated by the inorganic nanoparticle.

14. The method of claim 1, wherein the dye is a positively charged dye.

15. The method of claim 14, wherein the positively charged dye is chosen from Cy5.5, Cy5, Cy7, Cy3, ATTO647N, methylene blue, ATTO663, ATTO620, ATTO665, ATTO465, ATTO495, ATTO520, ATTORho6G, ATTORho3B, ATTORho1 1, ATTORho12, ATTOThio12, ATTO580Q, ATTORhoIO1, ATTORho13, ATTO610, ATT0612Q, and ATTO647N.

16. The method of claim 14, wherein the positively charged dye is Cy5.

17. The method of claim 1, further comprising utilizing fluorescence correlation spectroscopy (FCS).

* * * * *